United States Patent
Wang et al.

(10) Patent No.: US 10,562,977 B2
(45) Date of Patent: *Feb. 18, 2020

(54) LIGAND-CYTOTOXIC DRUG CONJUGATE, PREPARATION METHOD THEREOF, AND USES THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Yali Wang, Shanghai (CN); Lianshan Zhang, Shanghai (CN); Jindong Liang, Shanghai (CN); Ang Li, Shanghai (CN); Fanglong Yang, Shanghai (CN)

(73) Assignees: Shanghai Hengrui Pharmaceutical Co., Ltd., Shanghai (CN); Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 489 days.

This patent is subject to a terminal disclaimer.

(21) Appl. No.: 15/113,610

(22) PCT Filed: Jan. 22, 2015

(86) PCT No.: PCT/CN2015/071289
§ 371 (c)(1),
(2) Date: Jul. 22, 2016

(87) PCT Pub. No.: WO2015/113476
PCT Pub. Date: Aug. 6, 2015

(65) Prior Publication Data
US 2017/0002090 A1 Jan. 5, 2017

(30) Foreign Application Priority Data

Jan. 29, 2014 (CN) .......................... 2014 1 0043554
Oct. 29, 2014 (CN) .......................... 2014 1 0593726

(51) Int. Cl.
*C07K 16/32* (2006.01)
*C07K 16/18* (2006.01)
*C07K 16/28* (2006.01)

(52) U.S. Cl.
CPC ............. *C07K 16/32* (2013.01); *C07K 16/18* (2013.01); *C07K 16/2851* (2013.01); *C07K 16/2863* (2013.01); *C07K 16/2875* (2013.01); *C07K 16/2884* (2013.01); *C07K 16/2896* (2013.01)

(58) Field of Classification Search
CPC ............ A61K 47/6851; A61K 47/6849; A61K 47/6811; A61K 47/6803; A61K 47/6801; A61K 47/68
See application file for complete search history.

(56) References Cited

U.S. PATENT DOCUMENTS

| | | |
|---|---|---|
| 4,970,198 A | 11/1990 | Lee et al. |
| 5,079,233 A | 1/1992 | Lee |
| 5,585,089 A | 12/1996 | Queen et al. |
| 5,606,040 A | 2/1997 | McGahren et al. |
| 5,693,762 A | 12/1997 | Queen et al. |
| 5,739,116 A | 4/1998 | Hamann et al. |
| 5,767,285 A | 6/1998 | Hamann et al. |
| 5,773,001 A | 6/1998 | Hamann et al. |
| 7,090,843 B1 | 8/2006 | Francisco et al. |
| 7,659,241 B2 | 2/2010 | Senter et al. |
| 8,088,387 B2 | 1/2012 | Steeves et al. |
| 8,652,479 B2 | 2/2014 | Ebens, Jr. et al. |
| 8,703,714 B2 | 4/2014 | Doronina et al. |
| 2004/0146934 A1* | 7/2004 | Meares ............ C07K 16/1282 435/7.1 |
| 2005/0169933 A1 | 8/2005 | Steeves et al. |
| 2005/0238649 A1* | 10/2005 | Doronina ................ C07K 7/02 424/178.1 |

FOREIGN PATENT DOCUMENTS

| | | | |
|---|---|---|---|
| CN | 1938046 A | 3/2007 | |
| CN | 102973947 A | 3/2013 | |
| WO | 2004010957 A2 | 2/2004 | |
| WO | 2005001038 A2 | 1/2005 | |
| WO | 2005037992 A2 | 4/2005 | |
| WO | 2008025020 A2 | 2/2008 | |
| WO | WO-2009079911 A1 * | 7/2009 | ........... C07K 14/505 |

OTHER PUBLICATIONS

March, Advanced Organic Chemistry, 1977, McGraw-Hill, New York, pp. 817-818 (Year: 1977).*
Hutchins and Natale , Organic Preparations and Procedures International, 1979, vol. 11, pp. 201-246 (Year: 1979).*
Doronina et al (Bioconjugate Chemistry, 2006, vol. 17, pp. 114-124) (Year: 2006).*
International Search Report dated May 4, 2015 in International Application No. PCT/CN2015/071289.
Agus et al., "Targeting ligand-activated ErbB2 signaling inhibits breast and prostate tumor growth," Cancer Cell, vol. 2, pp. 127-137 (2002).
Craft et al., "A mechanism for hormone-independent prostate cancer through modulation of androgen receptor signaling by the HER-2/neu tyrosine kinase," Nature Medicine, vol. 5, No. 3, pp. 280-285 (Mar. 1999).
Dijoseph et al., "Antibody-targeted chemotherapy with CMC-544: a CD22-targeted immunoconjugate of calicheamicin for the treatment of B-lymphoid malignancies," Blood, vol. 103, No. 5, pp. 1807-1814 (2004).

(Continued)

*Primary Examiner* — Karen A. Canella
(74) *Attorney, Agent, or Firm* — Panitech Schwarze Belisario & Nadel LLP

(57) ABSTRACT

Ligand-cytotoxic drug conjugates, pharmaceutical compositions, preparation methods, and pharmaceutical uses thereof are provided. More specifically, a ligand-cytotoxic drug conjugate of general formula Pc-(X-Y-D)$_n$ is provided. The ligand-cytotoxic drug conjugate can be used to treat cancer via receptor modulation.

28 Claims, 1 Drawing Sheet
Specification includes a Sequence Listing.

(56) References Cited

OTHER PUBLICATIONS

Rabasseda et al., "Gemtuzumab Ozogamicin—Treatment of Acute Myeloid Leukemia," Drugs of the Future, vol. 25, No. 7, pp. 686-692 (2000).
Franklin et al., "Insights into ErbB signaling from the structure of the ErbB2-pertuzumab complex," Cancer Cell, vol. 5, pp. 317-328 (2004).
Jackson et al., "Blockade of Epidermal Growth Factor- or Heregulin-Dependent ErbB2 Activation with the Anti-ErbB2 Monoclonal Antibody 2C4 Has Divergent Downstream Signaling and Growth Effects," Cancer Research, vol. 64, pp. 2601-2609 (2004).
Mendoza et al., "Inhibition of Ligand-mediated HER2 Activation in Androgen-independent Prostate Cancer," Cancer Research, vol. 62, pp. 5485-5488 (2002).
Mullard, "Maturing antibody-drug conjugate pipeline hits 30," Nature Reviews Drug Discovery, vol. 12, pp. 329-332 (2013).
Doronina et al., "Development of potent monoclonal antibody auristatin conjugates for cancer therapy," Nature Biotechnology, vol. 21, No. 7, pp. 778-784 (Jul. 2003).
Oxley et al., "Her-2/neu oncogene amplification in clinically localised prostate cancer," Journal of Clinical Pathology, vol. 55, pp. 118-120 (2002).
Reese et al., "HER2 Protein Expression and Gene Amplification in Androgen-Independent Prostate Cancer," American Journal of Clinical Pathology, vol. 116, pp. 234-239 (2001).
Schaefer et al., "g-Heregulin: a novel heregulin isoform that is an autocrine growth factor for the human breast cancer cell line, MDA-MB-175," Oncogene, vol. 15, pp. 1385-1394 (1997).
Takai et al., "2C4, a Monoclonal Antibody against HER2, Disrupts the HER Kinase Signaling Pathway and Inhibits Ovarian Carcinoma Cell Growth," Cancer, vol. 104, pp. 2701-2708 (2005).

* cited by examiner

SEQUENCE LISTING

<160> NUMBER OF SEQ ID NOS: 14

<210> SEQ ID NO 1
<211> LENGTH: 214
<212> TYPE: PRT
<213> ORGANISM: Artificial sequence
<220> FEATURE:
<223> OTHER INFORMATION: Light Chain of Trastuzumab

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 450
<212> TYPE: PRT
<213> ORGANISM: Artificial sequence
<220> FEATURE:
<223> OTHER INFORMATION: Heavy Chain of Trastuzumab

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 219
<212> TYPE: PRT
<213> ORGANISM: Artificial sequence
<220> FEATURE:
<223> OTHER INFORMATION: Light Chain of Inotuzumab
```

<400> SEQUENCE: 3

Asp Val Gln Val Thr Gln Ser Pro Ser Ser Leu Ser Ala Ser Val Gly
1               5                   10                  15

Asp Arg Val Thr Ile Thr Cys Arg Ser Gln Ser Leu Ala Asn Ser
            20                  25                  30

Tyr Gly Asn Thr Phe Leu Ser Trp Tyr Leu His Lys Pro Gly Lys Ala
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 4
<211> LENGTH: 448
<212> TYPE: PRT
<213> ORGANISM: Artificial sequence
<220> FEATURE:
<223> OTHER INFORMATION: Heavy Chain of Inotuzumab

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 5
<211> LENGTH: 218
<212> TYPE: PRT
<213> ORGANISM: Artificial sequence
<220> FEATURE:
<223> OTHER INFORMATION: Light Chain of Brentuximab

<400> SEQUENCE: 5

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

```
Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 6
<211> LENGTH: 454
<212> TYPE: PRT
<213> ORGANISM: Artificial sequence
<220> FEATURE:
<223> OTHER INFORMATION: Heavy Chain of Brentuximab

<400> SEQUENCE: 6

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Thr Trp Val Lys Gln Lys Pro Gly Gln Gly Leu Glu Trp Ile
            35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ser Ser Thr Ala Phe
 65                  70                  75                  80

Met Gln Leu Ser Ser Leu Thr Ser Glu Asp Thr Ala Val Tyr Phe Cys
                 85                 90                  95

Ala Asn Tyr Gly Asn Tyr Trp Phe Ala Tyr Trp Gly Gln Gly Thr Gln
            100                 105                 110

Val Thr Val Ser Ala Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Ser Leu
        435                 440                 445
Ser Leu Ser Pro Gly Lys
    450

<210> SEQ ID NO 7
<211> LENGTH: 11
<212> TYPE: PRT
<213> ORGANISM: Artificial sequence
<220> FEATURE:
<223> OTHER INFORMATION: Anti-HER2-CDR-L1

<400> SEQUENCE: 7

Lys Ala Ser Gln Asp Val Ser Ile Gly Val Ala
1               5                   10

<210> SEQ ID NO 8
<211> LENGTH: 7
<212> TYPE: PRT
<213> ORGANISM: Artificial sequence
<220> FEATURE:
<223> OTHER INFORMATION: Anti-HER2-CDR-L2

<400> SEQUENCE: 8

Ser Ala Ser Tyr Arg Tyr Thr
1               5

<210> SEQ ID NO 9
```

```
<211> LENGTH: 9
<212> TYPE: PRT
<213> ORGANISM: Artificial sequence
<220> FEATURE:
<223> OTHER INFORMATION: Anti-HER2-CDR-L3

<400> SEQUENCE: 9

Gln Gln Tyr Tyr Ile Tyr Pro Tyr Thr
1               5

<210> SEQ ID NO 10
<211> LENGTH: 5
<212> TYPE: PRT
<213> ORGANISM: Artificial sequence
<220> FEATURE:
<223> OTHER INFORMATION: Anti-HER2-CDR-H1

<400> SEQUENCE: 10

Asp Tyr Thr Met Asp
1               5

<210> SEQ ID NO 11
<211> LENGTH: 17
<212> TYPE: PRT
<213> ORGANISM: Artificial sequence
<220> FEATURE:
<223> OTHER INFORMATION: Anti-HER2-CDR-H2

<400> SEQUENCE: 11

Asp Val Asn Pro Asn Ser Gly Gly Ser Ile Tyr Asn Gln Arg Phe Lys
1               5                   10                  15

Gly

<210> SEQ ID NO 12
<211> LENGTH: 10
<212> TYPE: PRT
<213> ORGANISM: Artificial sequence
<220> FEATURE:
<223> OTHER INFORMATION: Anti-HER2-CDR-H3

<400> SEQUENCE: 12

Asn Leu Gly Pro Ser Phe Tyr Phe Asp Tyr
1               5                   10

<210> SEQ ID NO 13
<211> LENGTH: 214
<212> TYPE: PRT
<213> ORGANISM: Artificial sequence
<220> FEATURE:
<223> OTHER INFORMATION: Anti-HER2-CDR-Light chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 14
<211> LENGTH: 449
<212> TYPE: PRT
<213> ORGANISM: Artificial sequence
<220> FEATURE:
<223> OTHER INFORMATION: Anti-HER2-CDR- Heavy Chain

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

US 10,562,977 B2

LIGAND-CYTOTOXIC DRUG CONJUGATE, PREPARATION METHOD THEREOF, AND USES THEREOF

CROSS-REFERENCE TO RELATED APPLICATION

This application is a Section 371 of International Application No. PCT/CN2015/071289, filed Jan. 22, 2015, which was published in the Chinese language on Aug. 6, 2015, under International Publication No. WO 2015/113476 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688452_31 US_Sequence_Listing," creation date of Jul. 12, 2016, and having a size of 25 kB. The sequence listing submitted via EFS-Web is part of the specification and is herein incorporated by reference in its entirety.

FIELD OF THE INVENTION

The present invention relates to a class of ligand-cytotoxic drug conjugates having a new structure. Specifically, the present invention relates to ligand-cytotoxic drug conjugates, as well as their preparation method, pharmaceutical composition comprising the same, and the use of the conjugate or the pharmaceutical composition.

BACKGROUND

Chemotherapy is still one of the most important anti-tumor strategies, including surgery, radiation therapy, and targeted therapy methods. Although there are many types of highly efficient cytotoxins, the small difference between cancer cells and normal cells limits the extensive use of these anti-tumor compounds in the clinic due to the toxicity and side effects. Besides, the specificity of anti-tumor monoclonal antibodies against tumor cell surface antigens makes antibody drugs the first-line anti-tumor therapy drugs. However, the efficacy is often unsatisfactory when the antibody is used alone as the anti-tumor drug.

Antibody drug conjugate (ADC) means connecting a monoclonal antibody or antibody fragment with a bioactive cytotoxin via a stable chemical linker compound, taking full advantage of the binding specificity of the antibody to normal and tumor cell surface antigens and the high efficacy of cytotoxins, meanwhile avoiding low efficacy of the former and excessive side effects of the latter. This means that, compared with conventional traditional chemotherapy drugs, the antibody drug conjugate is capable of binding precisely to the tumor cells and reducing the impact on the normal cells (Mullard A, (2013) Nature Reviews Drug Discovery, 12:329-332; DiJoseph J F, Armellino D C, (2004) Blood, 103:1807-1814).

Early ADC drugs primarily used murine monoclonal antibodies, some of which had difficulties reaching the target as a result of the human immune response. Secondly, effector molecules, including doxorubicin used in the early stage, exhibited lower biological activity, which limited the efficacy of the first generation of antibody drug conjugates. In addition, the source of antibodies, the linking mode and number of linkers have not yet been optimized.

In 2000, the first antibody drug conjugate Mylotarg® (gemtuzumab ozogamicin, Wyeth Pharmaceuticals) was approved by the US Food and Drug Administration (FDA) for the treatment of acute myeloid leukemia (Drugs of the Future (2000) 25(7):686; U.S. Pat. Nos. 4,970,198; 5,079,233; 5,585,089; 5,606,040; 5,693,762; 5,739,116; 5,767,285; 5,773,001). Mylotarg® is a humanized CD33 antibody-calicheamicin conjugate, which was withdrawn by Pfizer itself in 2010 because of the limited efficacy and high toxicity.

August 2011, Adcetris® (brentuximab vedotin, Seattle Genetics Inc.) was approved through the US FDA Fast Track for the treatment of Hodgkin lymphoma and relapsed anaplastic large cell lymphoma (Nat. Biotechnol. (2003) 21(7): 778-784; WO2004010957; WO2005001038; U.S. Pat. Nos. 7,090,843A; 7,659,241; WO2008025020). Adcetris® is a novel targeting ADC drug, which causes the drug to act directly on the target CD30 of lymphoma cells, trigger endocytosis and consequently induce tumor cell apoptosis.

In February 2013, Kadcyla® (ado-trastuzumab emtansine, T-DM1) gained approval from the FDA for the treatment of advanced or metastatic breast cancer patients who are HER2-positive with trastuzumab- (trade name: Herceptin®) and paclitaxel-resistant (WO2005037992; U.S. Pat. No. 8,088,387). Both Mylotarg® and Adcetris® are target therapies for hematologic tumors, the organizational structure of which is relatively simple compared to that of solid tumors. Kadcyla® is the first ADC drug approved by the FDA for the treatment of solid tumors.

Kadcyla®, which uses ImmunoGen technology, is formed by conjugating a highly active mitosis inhibitor DM1 and Roche's trastuzumab via a stable thioether bond linker (T-DM1), wherein the average drug load of one trastuzumab is about 3.5 per DM1. Trastuzumab specifically binds to breast cancer cells in a patient, and is cleaved to release the DM1 intracellularly after endocytosis. The intracellular aggregation concentration of DM1 is sufficient to cause cell death due to mitotic disturbance, followed by regression of tumor focus (unlike Herceptin® mAb monotherapy, which often results in retardation of tumor growth). T-DM1 not only retains antibody-dependent inhibition of cell proliferation like Herceptin®, but it also increases the potential effect of cytotoxic drug. Also, because its toxins are released in the target tumor cells, the side effects thereof are not simultaneously increased with its increasing curative effect.

Pertuzumab (also known as 2C4, trade name of Perjeta) is a recombinant humanized monoclonal antibody, which was first called "HER dimerization inhibitor". Pertuzumab blocks the dimerization of HER2 and other HER receptors by binding to HER2 (Agus D B, (2002) Cancer Cell (2):127-137; Schaefer G, (1997) Oncogene (15): 1385-1394; Mendoza N, (2002) Cancer Res (62): 5485-5488; Takai N, (2005) Cancer (104): 2701-2708; Jackson J G, (2004) Cancer Res (64): 2601-2609). It has been verified that pertuzumab has an inhibitory effect on tumor growth in both HER2-high-expression and low-expression prostate cancer models (Craft N, (1999) Nat Med (5):280-285; Oxley J D, (2002) J Clin Pathol (55): 118-120; Reese D M, (2001) Am J Clin Pathol (116): 234-239; Agus D B, (2002) Cancer Cell (2): 127-137).

Being different from Trastuzumab (trade name Herceptin), which inhibits the downstream signaling pathways via the binding site located on the juxtamembrane region IV sub-domain of the HER2 extracellular domain, pertuzumab effectively inhibits the heterologous dimerization of HER2 via binding to domain II (dimerization domain). Therefore, trastuzumab only has some effect on patients with HER2 over-expressed cancer, especially on breast cancer patients. Although sharing the same target and endocytosis with trastuzumab, due to its different mechanism of action, pertuzumab can block the signaling pathway mediated by ErbB family receptor after inhibiting dimerization, and may have a more extensive application than the one only blocking the HER2 signaling pathway (Franklin M C, (2001) *Cancer Cell* (5): 317-328).

Currently, there are mainly two techniques for conjugation of ADC drug: for T-DM1, random conjugation of cytotoxic drug and free amino groups in the antibody is used (WO2005037992); while for Adcetris®, conjugation of cytotoxic drug and free thiol groups in the antibody after hinge region reduction (WO2004010957) is used. Both conjugation methods produce a mixture with an inconsistent Drug to Antibody Ratio. For example, the average Drug to Antibody Ratio of T-DM1 is 3.5, however, the drug loading distribution is from 0 to 8. A Low Drug to Antibody Ratio affects ADC efficacy, while a high Drug to Antibody Ratio more easily leads to excessive antibody modification, resulting in ADC drug recognition and destruction by the tissue macrophage system. This not only shortens the half-life of the ADC, but also increases the toxic side effects on account of accumulation of toxins in non-target tissues; and for Adcetris®, the disulfide bond of the antibody hinge region is reduced with a reducing agent, which would have a certain impact on the stability of the antibody itself.

SUMMARY OF THE INVENTION

In order to improve the conjugation effect of a ligand, especially an antibody, and a drug, the present invention provides an improved connecting unit for coupling a ligand and a drug.

The present invention discloses a ligand-cytotoxic drug conjugate or a pharmaceutically acceptable salt or solvate thereof, wherein the ligand-cytotoxic drug conjugate comprises a connecting unit X having the following structure:

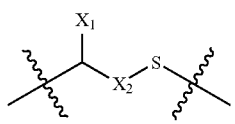

(X)

$X_1$ is selected from the group consisting of H, alkyl, cycloalkyl, heterocyclyl, aryl and heteroaryl, wherein the alkyl, cycloalkyl, heterocyclyl, aryl and heteroaryl are each independently and optionally substituted with one or more groups selected from the group consisting of halogen, hydroxy, cyano, alkyl, alkoxy, cycloalkyl, heterocyclyl, aryl and heteroaryl, $X_2$ is selected from the group consisting of alkyl, cycloalkyl, alkyl-cycloalkyl, cycloalkyl-alkyl, alkyl-cycloalkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, $(CH_2)_p(OCH_2CH_2)_p$, $(CH_2CH_2O)_p(CH_2)_p$, each p is an integer independently selected from 1 to 10, wherein the alkyl, cycloalkyl, heterocyclyl, aryl and heteroaryl are independently and optionally substituted with one or more groups selected from the group consisting of halo, hydroxy, cyano, alkyl, alkoxy, cycloalkyl, heterocyclyl, aryl and heteroaryl;

Or when $X_1$ is not H, $X_1$ and $X_2$ with the carbon atom joining $X_1$ and $X_2$ are taken together to form a cycloalkyl group, wherein the cycloalkyl is independently and optionally substituted with one or more groups selected from the group consisting of halo, hydroxy, cyano, alkyl, alkoxy, cycloalkyl, heterocyclyl, aryl and heteroaryl; and S is a sulfur atom.

In a preferred embodiment of the present invention, provided is a ligand-cytotoxic drug conjugate or a pharmaceutically acceptable salt or solvate thereof as described above, wherein $X_1$ is H or alkyl, preferably H.

In another preferred embodiment of the present invention, provided is a ligand-cytotoxic drug conjugate or a pharmaceutically acceptable salt or solvate thereof as described above, wherein $X_2$ is alkyl or cycloalkyl, preferably alkyl, more preferably linear alkyl.

In another preferred embodiment of the present invention, provided is a ligand-cytotoxic drug conjugate or a pharmaceutically acceptable salt or solvate thereof as described above, comprising a structure of formula (I):

Wherein:

Pc is a ligand;

X is as defined in claim 1;

Y is an interval unit;

D is a cytotoxic drug; and n is a Drug to Antibody Ratio, n is selected from 1 to 8.

In another preferred embodiment of the present invention, provided is a ligand-cytotoxic drug conjugate or a pharmaceutically acceptable salt or solvate thereof as described above, wherein the connecting unit X is linked with an N-terminal amino group of a Pc polypeptide chain or ε-amino group of a lysine residue, and n is selected from 1 to 4.

In another preferred embodiment of the present invention, provided is a ligand-cytotoxic drug conjugate or a pharmaceutically acceptable salt or solvate thereof as described above, wherein the ligand is an antibody.

In another preferred embodiment of the present invention, provided is a ligand-cytotoxic drug conjugate or a pharmaceutically acceptable salt or solvate thereof as described above, wherein the antigen of said antibody is a cell surface antigen expressed on a target cell and/or tissue of a proliferative disease; the proliferative disease is preferably cancer; and the cell surface antigen is preferably a cell surface receptor.

In another preferred embodiment of the present invention, provided is a ligand-cytotoxic drug conjugate or a pharmaceutically acceptable salt or solvate thereof as described above, wherein the cell surface receptor is selected from the group consisting of:

1) HER2 (ErbB2),
2) HER3 (ErbB3),
3) HER4 (ErbB4),
4) CD20,
5) CD22,
6) CD30,
7) CD33,
8) CD44,
9) Lewis Y,
10) CD56,
11) CD105,
12) VEGFR, and
13) GPNMB.

In another preferred embodiment of the present invention, provided is a ligand-cytotoxic drug conjugate or a pharmaceutically acceptable salt or solvate thereof as described above, wherein the cell surface receptor is selected from the group consisting of:
1) HER2 (ErbB2),
2) CD 22,
3) CD30
4) CD33,
5) CD44
6) CD56,
7) Lewis Y, and
8) GPNMB.

In another preferred embodiment of the present invention, provided is a ligand-cytotoxic drug conjugate or a pharmaceutically acceptable salt or solvate thereof as described above, wherein the antibody is selected from the group consisting of:
1) Trastuzumab (HER2),
2) Inotuzumab (CD22),
3) Pinatuzumab (CD22),
4) Brentuximab (CD30),
5) Gemtuzumab (CD33),
6) Bivatuzumab (CD44),
7) Lorvotuzumab (CD56),
8) cBR96 (Lewis Y),
9) Glematumamab (GPNMB) and
10) Pertuzumab.

In another preferred embodiment of the present invention, provided is a ligand-cytotoxic drug conjugate or a pharmaceutically acceptable salt or solvate thereof as described above, wherein the antibody is capable of binding to HER2 protein, the antibody comprises:
1) a light chain comprising at least one CDR selected from the three of CDR-L1, CDR-L2 and CDR-L3 defined according to the Kabat numbering system, wherein
  i) CDR-L1 is a CDR of SEQ ID NO: 1, or of at least one sequence having at least 80% identity to SEQ ID NO: 1 after optimal alignment;
  ii) CDR-L2 is a CDR of SEQ ID NO: 2, or of at least one sequence having at least 80% identity to SEQ ID NO: 2 after optimal alignment; and
  iii) CDR-L3 is a CDR of SEQ ID No: 3, or of at least one sequence having at least 80% identity to SEQ ID NO: 3 after optimal alignment; and
2) a heavy chain comprising at least one CDR selected from the three of CDR-H1, CDR-H2 and CDR-H3 defined according to the Kabat numbering system, wherein
  iv) CDR-H1 is a CDR of SEQ ID NO: 4, or of at least one sequence having at least 80% identity to SEQ ID NO: 4 after optimal alignment;
  v) CDR-H2 is a CDR of SEQ ID NO: 5, or of at least one sequence having at least 80% identity to SEQ ID NO: 5 after optimal alignment; and
  vi) CDR-H3 is a CDR of SEQ ID NO: 6, or of at least one sequence having at least 80% identity to SEQ ID NO: 6 after optimal alignment.

In another preferred embodiment of the present invention, provided is a ligand-cytotoxic drug conjugate or a pharmaceutically acceptable salt or solvate thereof as described above, wherein the antibody capable of binding to HER2 protein comprises a light chain and/or heavy chain, the light chain comprises an amino acid sequence of SEQ ID NO: 7, and the heavy chain comprises an amino acid sequence of SEQ ID NO: 8.

In another preferred embodiment of the present invention, provided is a ligand-cytotoxic drug conjugate or a pharmaceutically acceptable salt or solvate thereof as described above, wherein the cytotoxic drug is selected from the group consisting of tubulin inhibitors, DNA alkylating agents, tyrosine kinase inhibitors, topoisomerase inhibitors and DNA synthesis inhibitors, preferably tubulin inhibitors.

In another preferred embodiment of the present invention, provided is a ligand-cytotoxic drug conjugate or a pharmaceutically acceptable salt or solvate thereof as described above, wherein the topoisomerase inhibitor is selected from the group consisting of camptothecin, irinotecan, actinomycin, adriamycin, doxorubicin, daunorubicin, and epirubicin; the DNA synthesis inhibitor is selected from the group consisting of fluorouracil, cytarabine, azacitidine, ancitabine, gemcitabine, capecitabine, methotrexate, bleomycin, and platinum complexes; the DNA alkylating agent is selected from the group consisting of nitrogen mustards (cyclophosphamide), ethylidenehydrazono amines (thiotepa, mitomycin), methanesulfonic acid esters (busulfan), polyols (dibromo mannitol), nitrosoureas (carmustine), triazene imidazole (dacarbazine) and hydrazines (procarbazine); and the tyrosine kinase inhibitor is selected from the group consisting of imatinib, gefitinib, erlotinib, sunitinib, sorafenib, lapatinib, dasatinib, and nilotinib.

In another preferred embodiment of the present invention, provided is a ligand-cytotoxic drug conjugate or a pharmaceutically acceptable salt or solvate thereof as described above, wherein the cytotoxic drug tubulin inhibitor is selected from the group consisting of maytansinoids, calicheamicin, taxanes, vincristine, colchicine, and Dolastatins/Auristatins, preferably maytansinoid and Dolastatins/Auristatins.

In a further preferred embodiment of the present invention, provided is a ligand-cytotoxic drug conjugate or a pharmaceutically acceptable salt or solvate thereof as described above, wherein D is selected from the Dolastatins/Auristatins, with a structure of formula $(D_1)$:

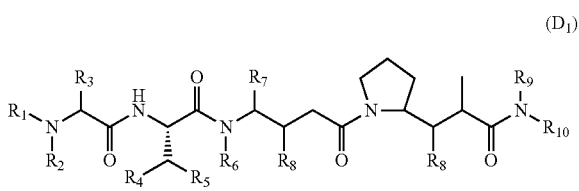

wherein:
$R_1$ is a bond, H, alkyl or cycloalkyl, preferably a bond; when $R_1$ is H, alkyl or cycloalkyl, D is linked with Y through $R_{10}$ in the formula (I); when $R_1$ is preferably a bond, D is linked with Y through $R_{10}$ in the formula (I);

$R_2$ is H or alkyl;

Or $R_1$ and $R_2$ with the joined N atom are taken together to form a heterocyclyl, wherein the heterocyclyl is independently and optionally substituted with one or more groups selected from the group consisting of halo, hydroxy, cyano, alkyl, alkoxy, cycloalkyl, heterocyclyl, aryl, and heteroaryl; or to form a structure of $-(CR_aR_b)_e-$, wherein $R_a$ and $R_b$ are independently selected from the group consisting of H, alkyl, and heterocyclyl, and e is an integer selected from 2 to 6;

$R_3$ is selected from the group consisting of H, alkyl, cycloalkyl, aryl, alkyl-aryl, alkyl-cycloalkyl, heterocyclyl and alkyl-heterocyclyl;

$R_4$ is selected from the group consisting of H, alkyl, cycloalkyl, aryl, alkyl-aryl, alkyl-cycloalkyl, heterocyclyl and alkyl-heterocyclyl;

$R_5$ is H or methyl;

$R_6$ is H or alkyl;

$R_7$ is selected from the group consisting of H, alkyl, cycloalkyl, aryl, alkyl-aryl, alkyl-cycloalkyl, heterocyclyl and alkyl-heterocyclyl;

$R_8$ is selected from the group consisting of H, hydroxy, alkyl, cycloalkyl, and alkoxy;

$R_9$ is H or alkyl;

When $R_1$ is alkyl or cycloalkyl, or $R_1$ and $R_2$ with the joined N atom are taken together to form a heterocyclyl, wherein the heterocyclyl is independently and optionally substituted with one or more groups selected from the group consisting of halo, hydroxy, cyano, alkyl, alkoxy, cycloalkyl, heterocyclyl, aryl, and heteroaryl, $R_{10}$ is selected from the following structures:

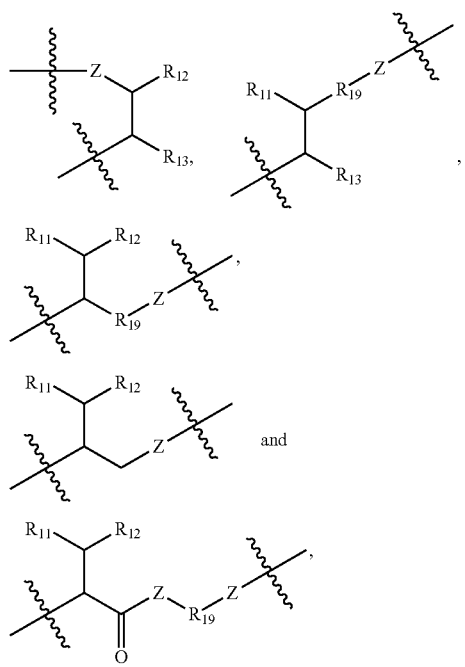

When $R_1$ is H, $R_{10}$ is selected from the following structures:

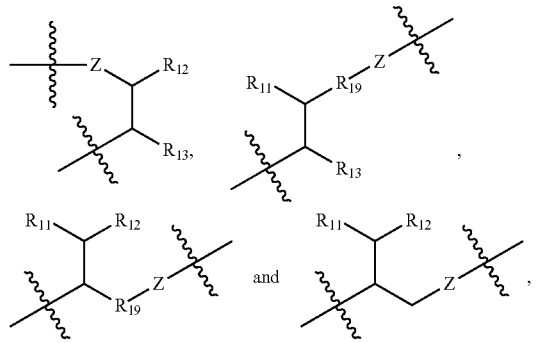

When $R_1$ is a bond, it is connected with the interval unit Y, wherein $R_{10}$ is selected from the following structures:

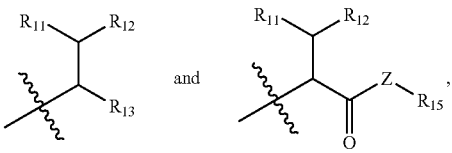

$Z$ is selected from the group consisting of O, S, NH and $N(R_{14})$;

$R_{11}$ is selected from the group consisting of H, hydroxy, amino, —NHR$_{14}$, —N(R$_{14}$)$_2$ alkoxy, alkyl, cycloalkyl, aryl, heterocyclyl, alkyl-aryl, alkyl-cycloalkyl, and alkyl-heterocyclyl; or when $R_{11}$ is O, it can replace a H attached on the joined carbon atom, and form a carbonyl group (C=O) with this carbon atom;

$R_{12}$ is selected from the group consisting of aryl and heterocyclyl, the aryl and heterocyclyl is each optionally substituted by one or more groups selected from the group consisting of hydroxy, alkoxy, alkyl, and halogen;

$R_{13}$ is selected from the group consisting of H, hydroxy, amino, NHR$_{14}$, N(R$_{14}$)$_2$, COOR$_{14}$, alkoxy, alkyl, cycloalkyl, aryl, heterocyclyl, alkyl-aryl, alkyl-cycloalkyl, alkyl-heterocyclyl and alkoxy-alkoxy-alkoxy;

$R_{14}$ is H or alkyl;

$R_{15}$ is selected from the group consisting of H, alkyl, aryl, heterocyclyl, (R$_{16}$O)$_m$—R$_{14}$ and (R$_{16}$O)$_m$—CH(R$_{17}$)$_2$;

m is an integer selected from 1 to 1,000;

$R_{16}$ is C$_2$-C$_8$ alkyl;

$R_{17}$ is selected from the group consisting of H, carboxyl, —(CH$_2$)$_t$—N(R-$_{18}$)$_2$ and —(CH$_2$)$_t$—SO$_3$R$_{14}$;

$R_{18}$ is selected from the group consisting of H, alkyl, and —(CH$_2$)$_t$—COOH;

t is an integer selected from 0 to 6;

$R_{19}$ is selected from the group consisting of aryl, cycloalkyl and heterocyclyl.

In a further preferred embodiment of the present invention, provided is a ligand-cytotoxic drug conjugate or a pharmaceutically acceptable salt or solvate thereof having formula (D1), wherein:

$R_1$ is a bond or alkyl;

$R_2$ is H or alkyl;

$R_3$ is H, alkyl or cycloalkyl;

$R_4$, $R_5$, $R_6$, and $R_7$ are each independently H, alkyl, cycloalkyl or heterocyclyl;

$R_8$ is H, alkyl, cycloalkyl or alkoxy;

$R_9$ is H or alkyl;

When $R_1$ is -alkyl, $R_{10}$ is selected from the following structure:

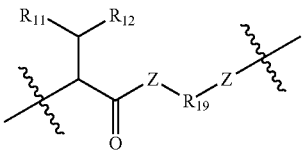

When $R_1$ is a bond, it is linked with an interval unit Y, wherein $R_{10}$ is selected from the following structure:

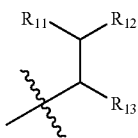

Z is NH;

R$_{11}$ is H, hydroxy or alkyl;

R$_{12}$ is aryl, the aryl is optionally substituted with one or more groups selected from the group consisting of hydroxy, alkoxy, alkyl, and halogen;

R$_{13}$ is H, alkyl or COOR$_{14}$;

R$_{14}$ is H or alkyl, the alkyl is optionally substituted with alkoxy or alkoxy-alkoxy-alkoxy; and R$_{19}$ is aryl.

In a further preferred embodiment of the present invention, R$_3$ in formula (D$_1$) is H or isopropyl.

In another preferred embodiment of the present invention, provided is a ligand-cytotoxic drug conjugate or a pharmaceutically acceptable salt or solvate thereof as mentioned above, wherein D is selected from maytansine, with a structure of formula (D$_M$):

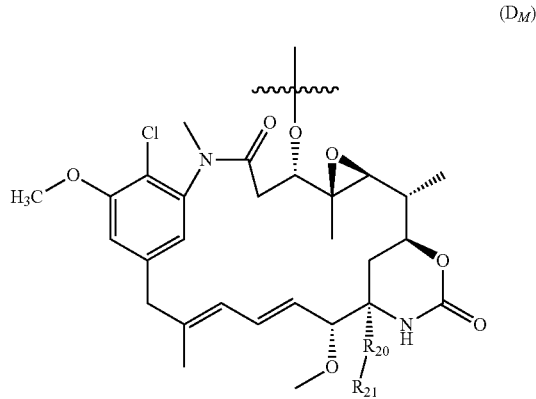

wherein:

R$_{20}$ is O or S;

R$_{21}$ is selected from the group consisting of H, alkyl, cycloalkyl, heterocyclyl, aryl, and heteroaryl, wherein the alkyl, cycloalkyl, heterocyclyl, aryl and heteroaryl are independently and optionally substituted by one or more groups selected from the group consisting of halogen, hydroxy, cyano, nitro, alkyl, alkoxy, cycloalkyl, heterocyclyl, aryl and heteroaryl.

In another preferred embodiment of the present invention, provided is a ligand-cytotoxic drug conjugate or a pharmaceutically acceptable salt or solvate thereof, wherein D is D$_1$, wherein the interval unit Y has a structure of the following formula:

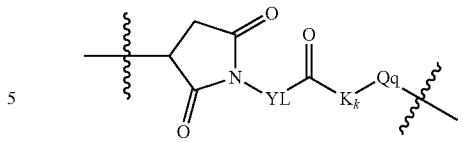

wherein:

YL is selected from the group consisting of alkyl, cycloalkyl, O-alkyl, O-alkoxy, aryl, alkyl-cycloalkyl, cycloalkyl-alkyl, alkyl-aryl, alkyl-cycloalkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, CH$_2$(OCH$_2$CH$_2$)$_t$, (CH$_2$CH$_2$O)$_t$CH$_2$, and (CH$_2$CH$_2$O)$_t$, t is an integer selected from 1 to 10, preferably an alkyl group, more preferably C$_2$-C$_8$ linear alkyl;

K$_k$ is an amino acid unit, wherein K is an amino acid, k is an integer selected from 0 to 10, preferably 2, K$_k$ is preferably valine-citrulline;

Q$_q$ is an extended unit, wherein q is 0, 1 or 2.

The present invention also relates to a compound of formula (II):

$$Pc\text{-}(\text{-}X\text{-}T)_n \quad (II)$$

which is used for preparing an intermediate compound of formula (III), wherein:

Pc is as defined in formula (I);

X is defined as connecting unit X;

T is selected from the group consisting of H, t-butyl, acetyl, n-propionyl, isopropionyl, triphenylmethyl, methoxymethyl, and 2-(trimethylsilyl)ethoxymethyl, preferably H or acetyl;

n is selected from 1 to 4.

In another preferred embodiment of the present invention, provided is a ligand-cytotoxic drug conjugate or a pharmaceutically acceptable salt or solvate thereof as described above, comprising a structure of formula (III):

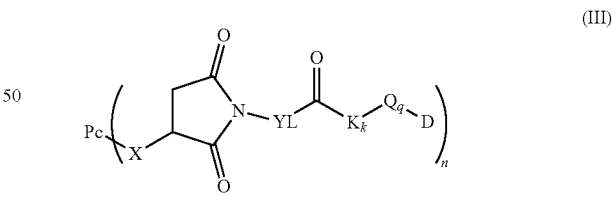

(III)

Wherein:

Pc is an antibody;

X is defined as a connecting unit X;

YL, K$_k$, and Q$_q$ are as defined in formula (Y);

n is selected from 1 to 4; and

D is a cytotoxic drug.

In another preferred embodiment of the present invention, provided is a ligand-cytotoxic drug conjugate or a pharmaceutically acceptable salt or solvate thereof as described above, comprising any one of the following structures:

11  12
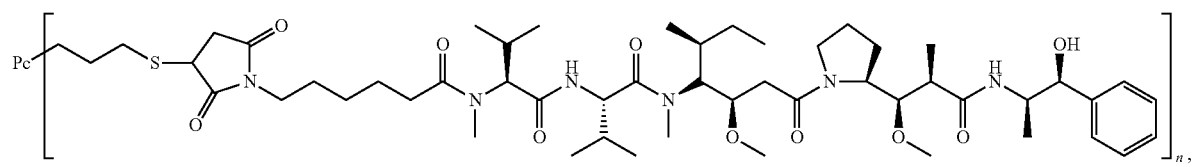
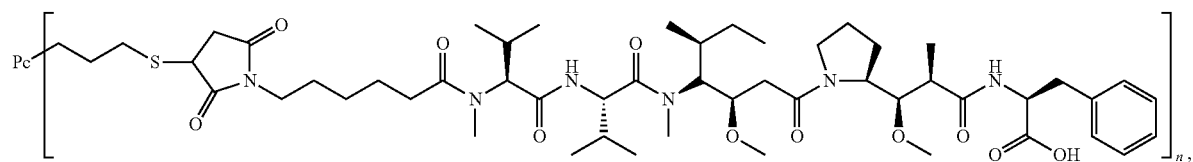
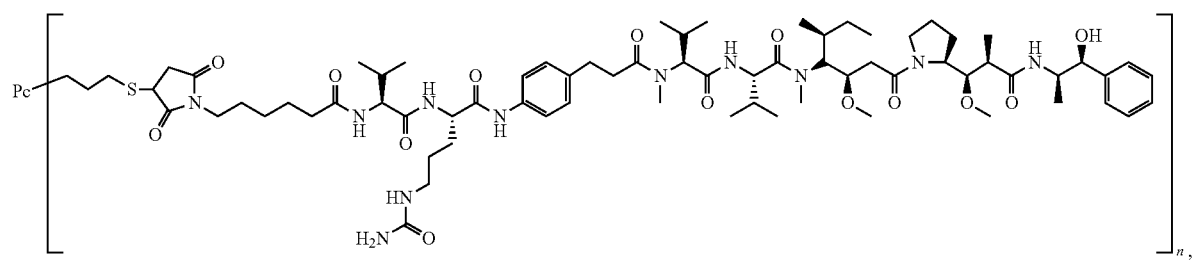
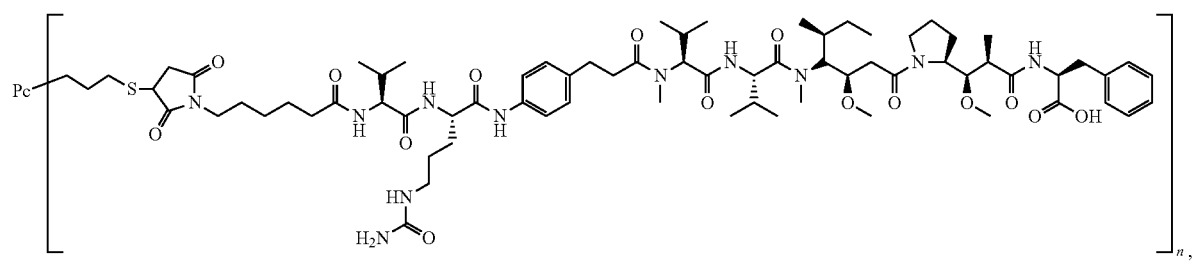
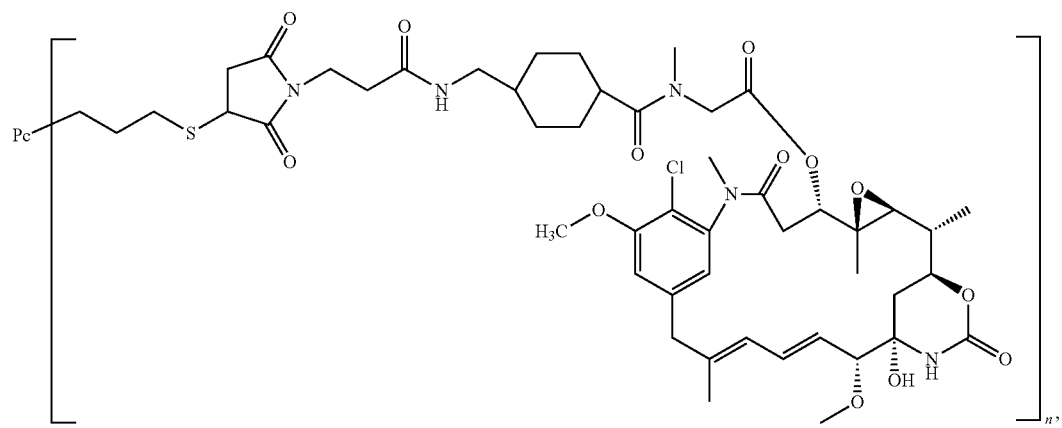
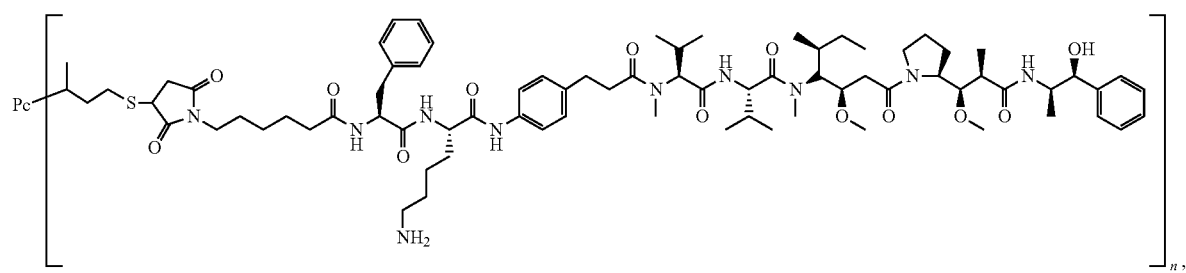

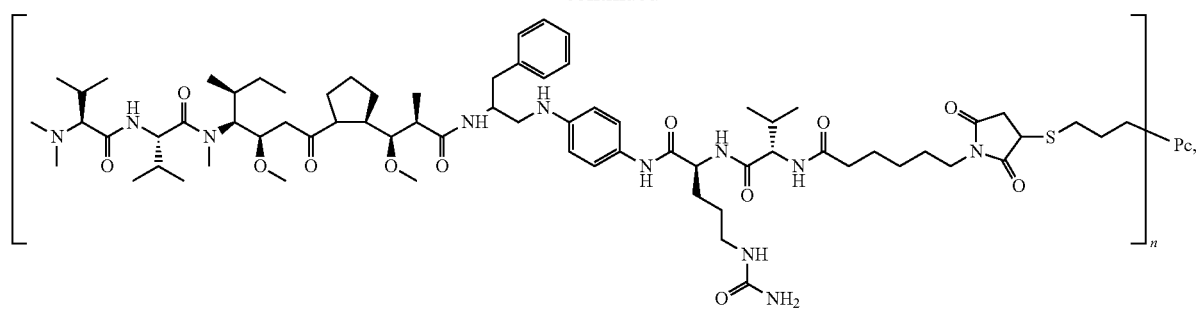
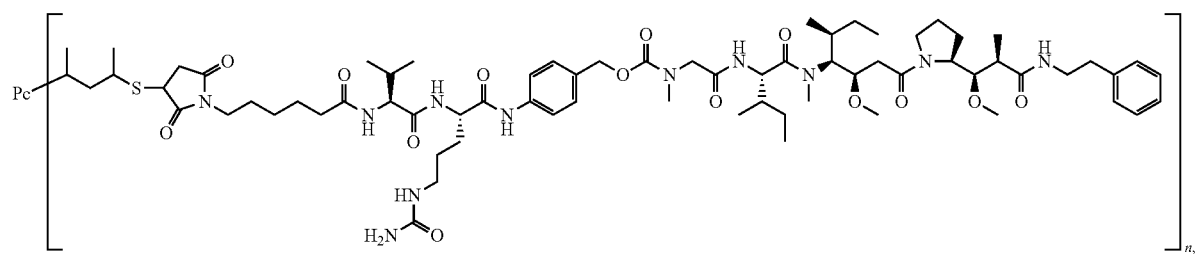
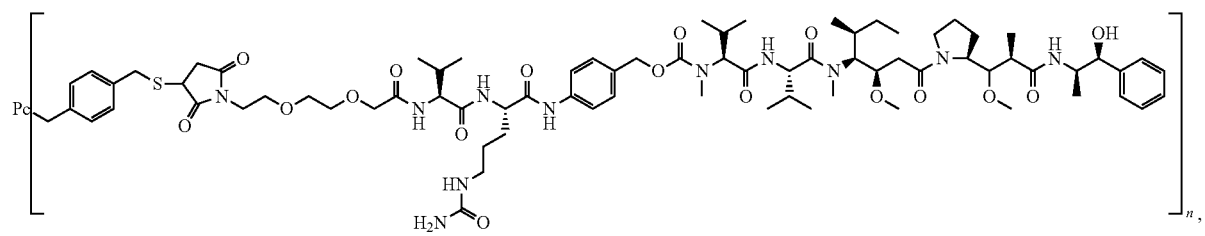
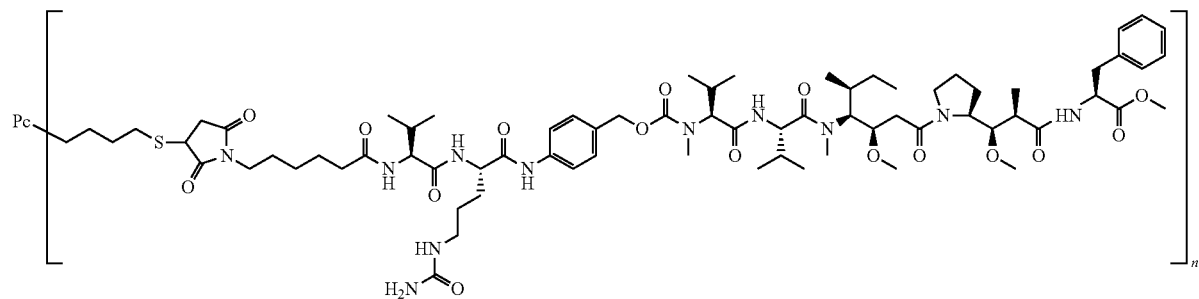
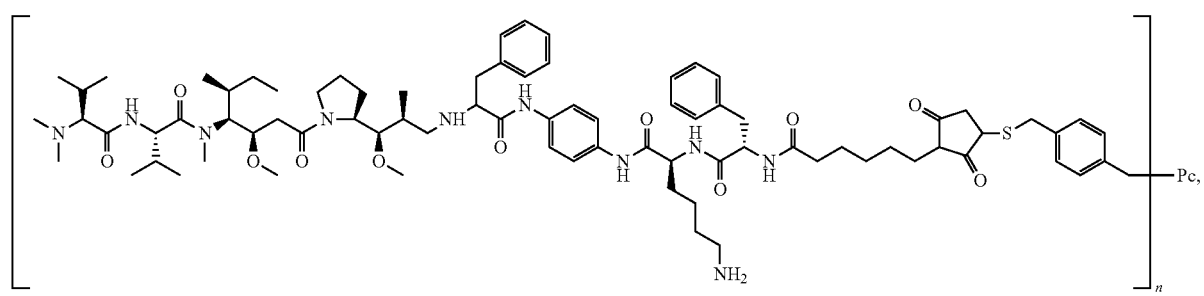
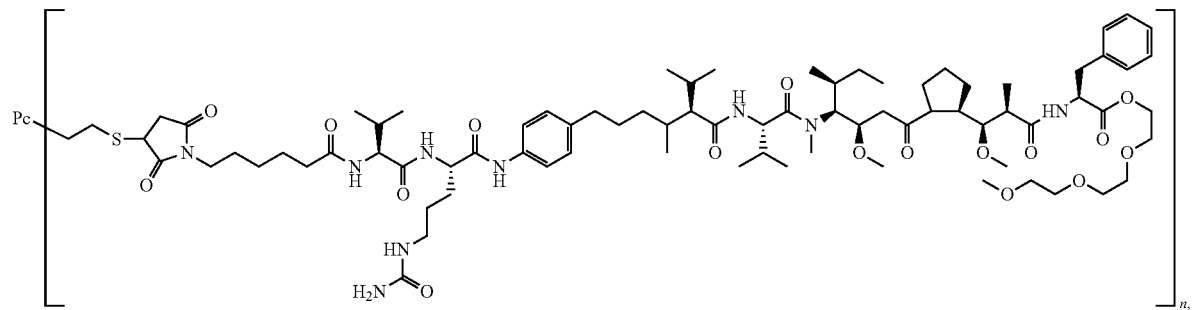

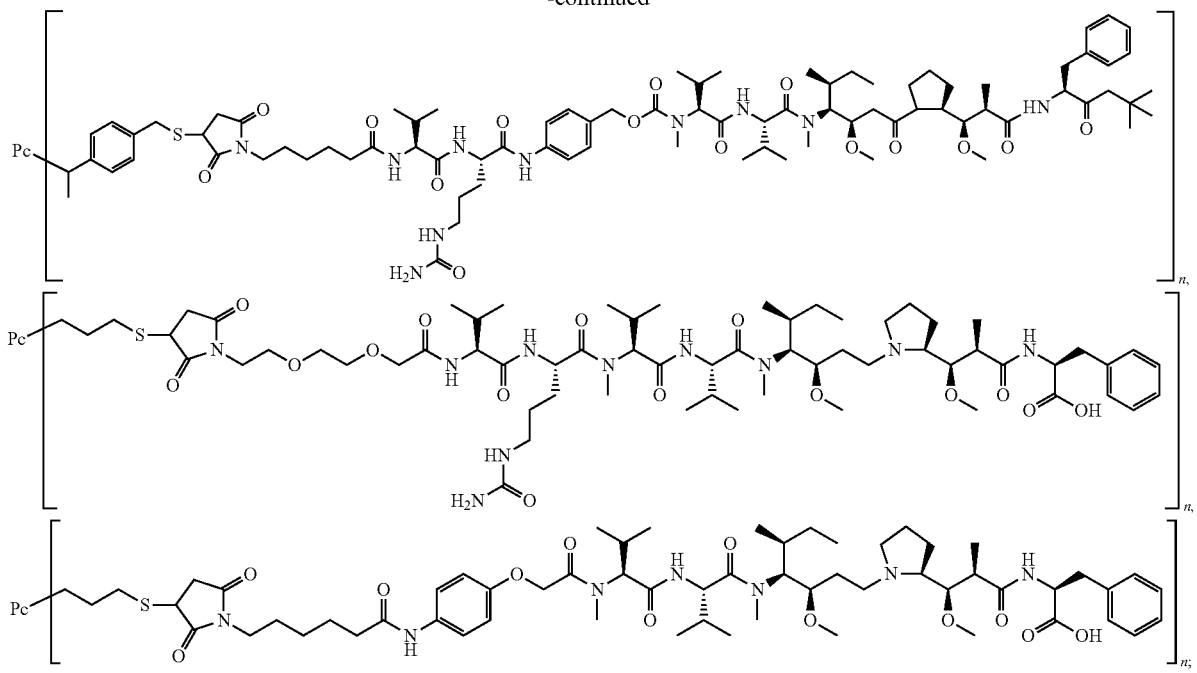

wherein Pc is ligand, n is Drug to Antibody Ratio, and n is selected from 1 to 8.

In another specific embodiment of the present invention, provided is a ligand-cytotoxic drug conjugate or a pharmaceutically acceptable salt or solvate thereof as described above, wherein Pc is selected from the group consisting of Trastuzumab, Inotuzumab and Brentuximab, preferably Trastuzumab or Pertuzumab, more preferably Pertuzumab.

In another specific embodiment of the present invention, provided is a ligand-cytotoxic drug conjugate or a pharmaceutically acceptable salt or solvate thereof as described above, selected from the group consisting of:

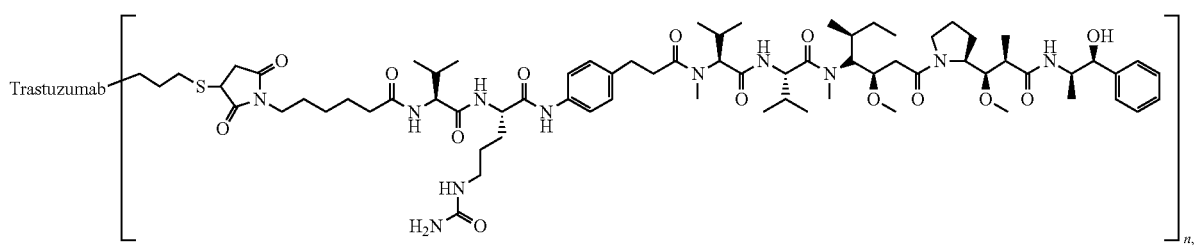

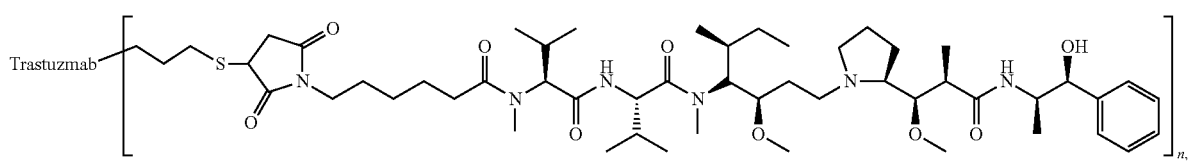

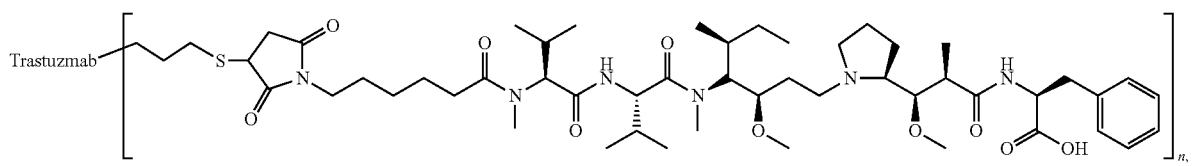

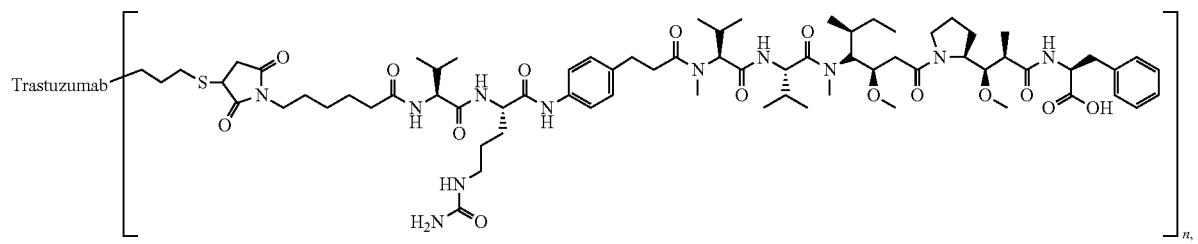
19
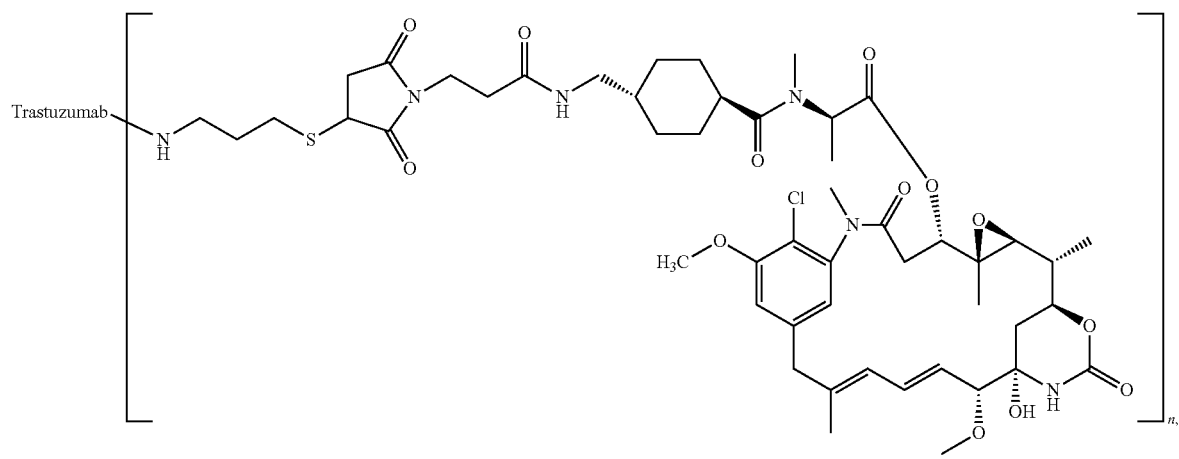
20
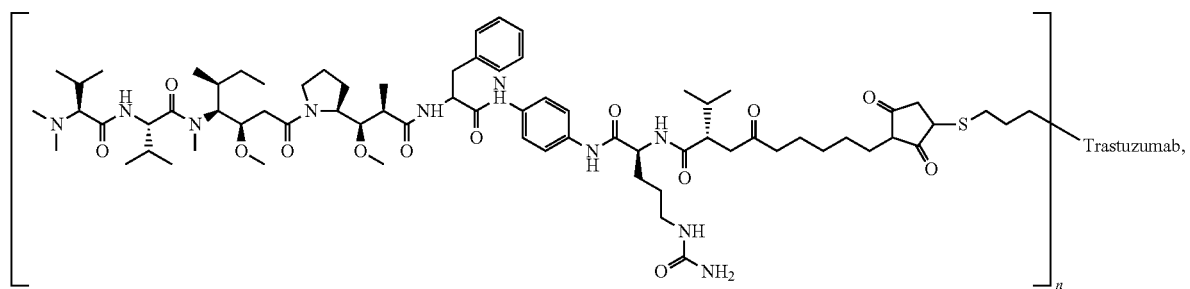
21
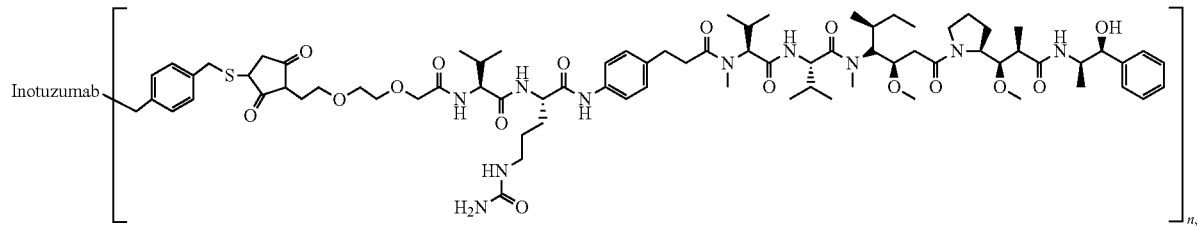
24
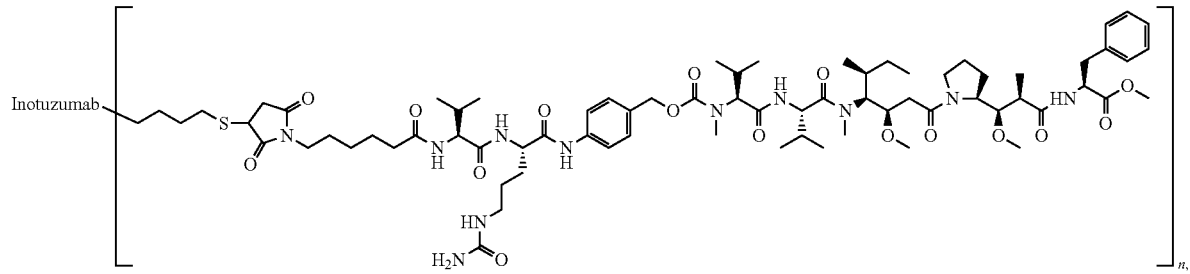
25

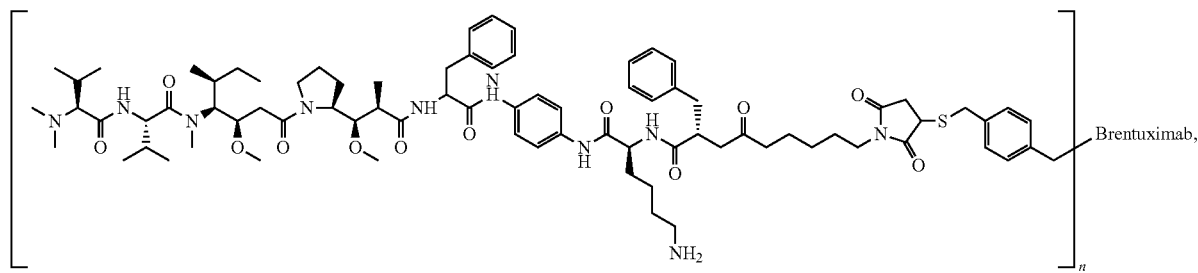
26
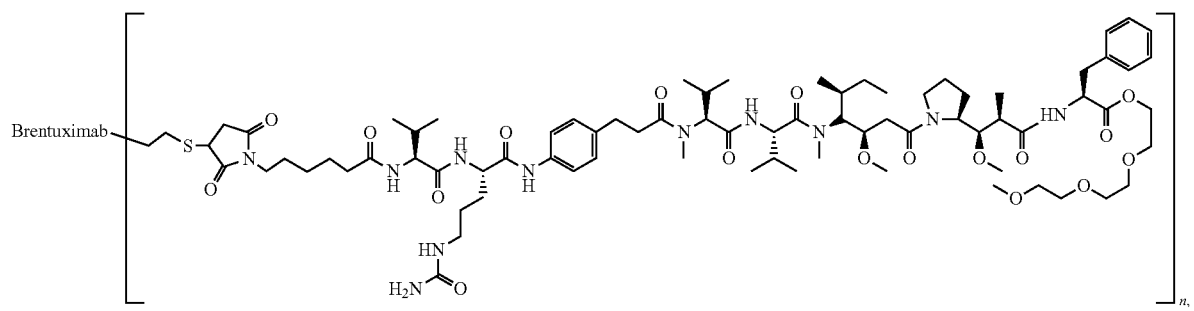
27
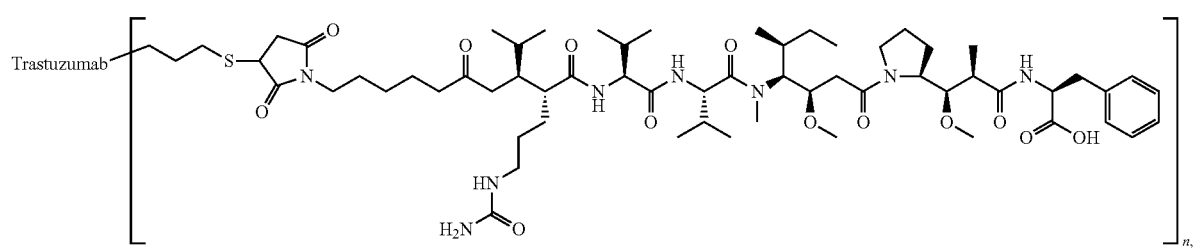
29
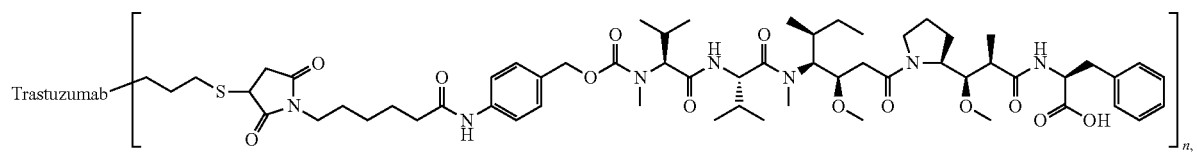
30
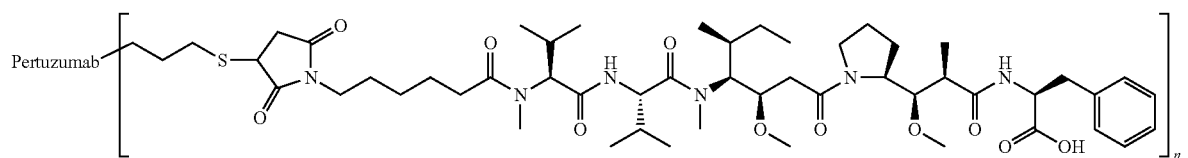
31
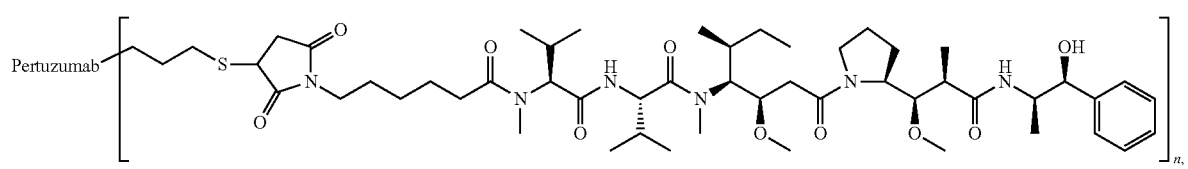
32

-continued
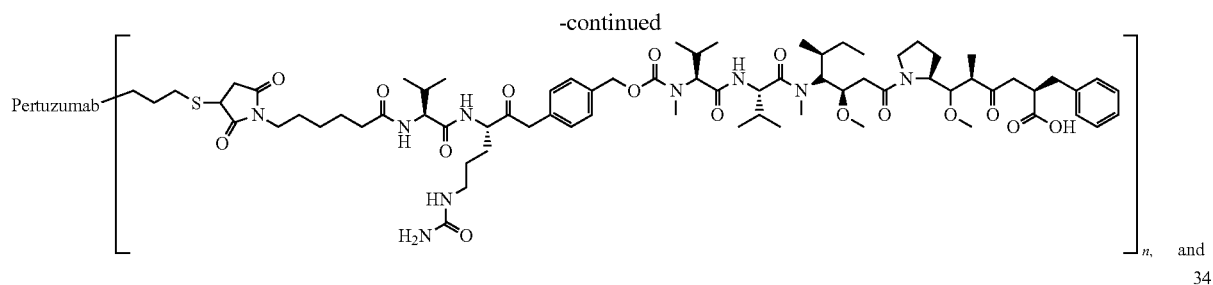
21
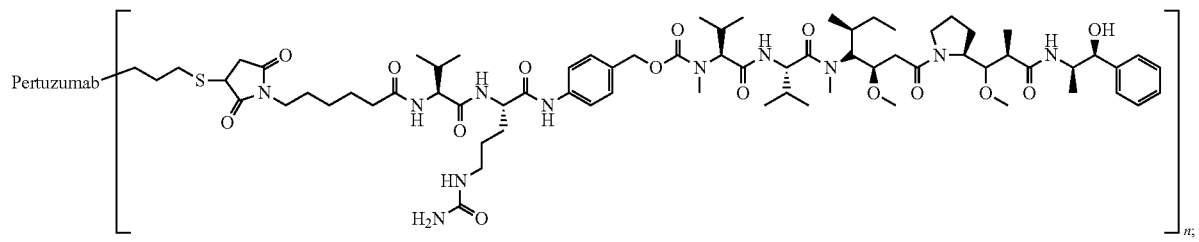
n is selected from 1 to 8, preferably 1 to 4.
In another specific embodiment of the present invention, provided is a ligand-cytotoxic drug conjugate or a pharmaceutically acceptable salt or solvate thereof as described above, selected from the group consisting of:
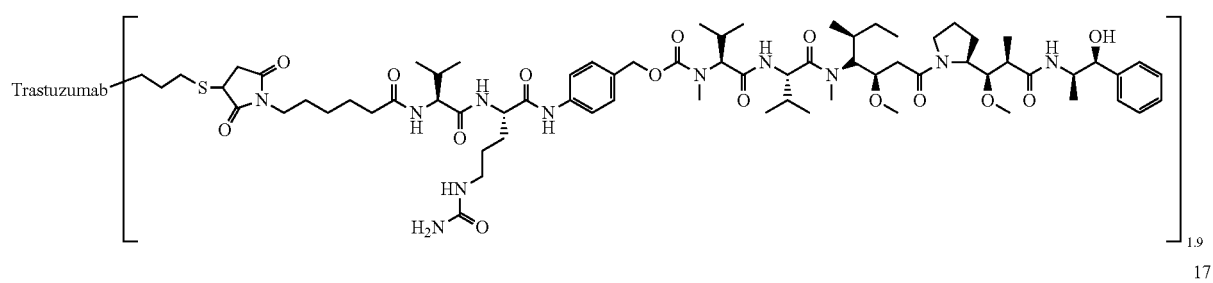
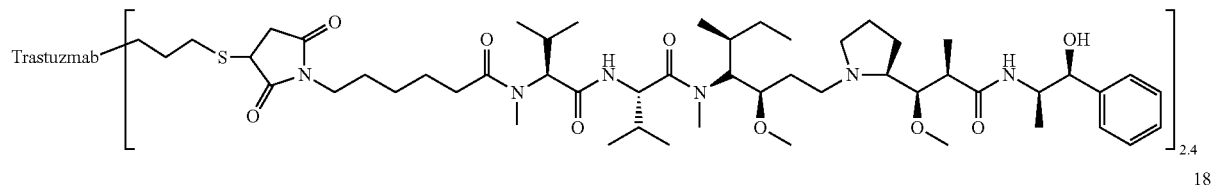
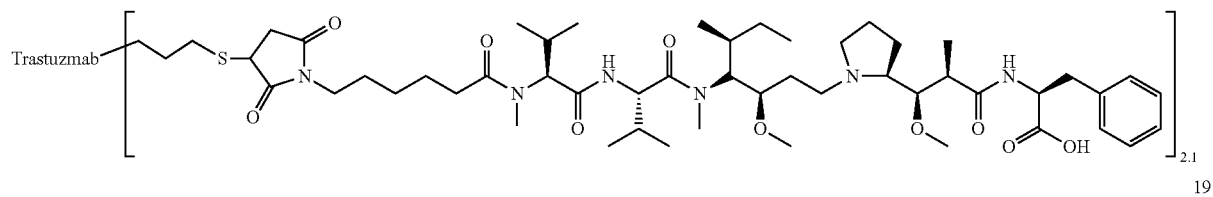
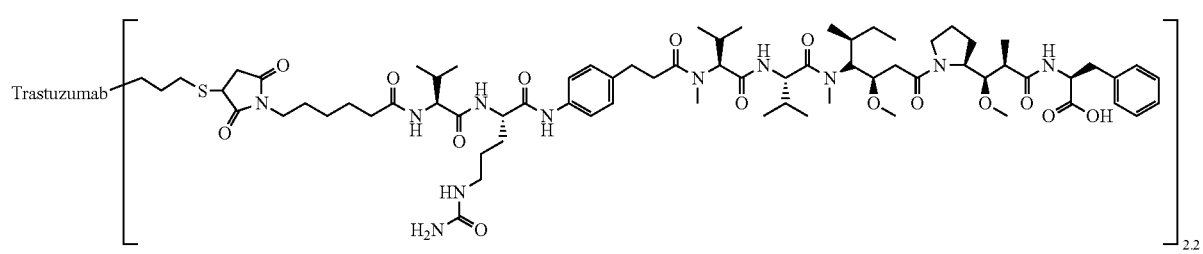

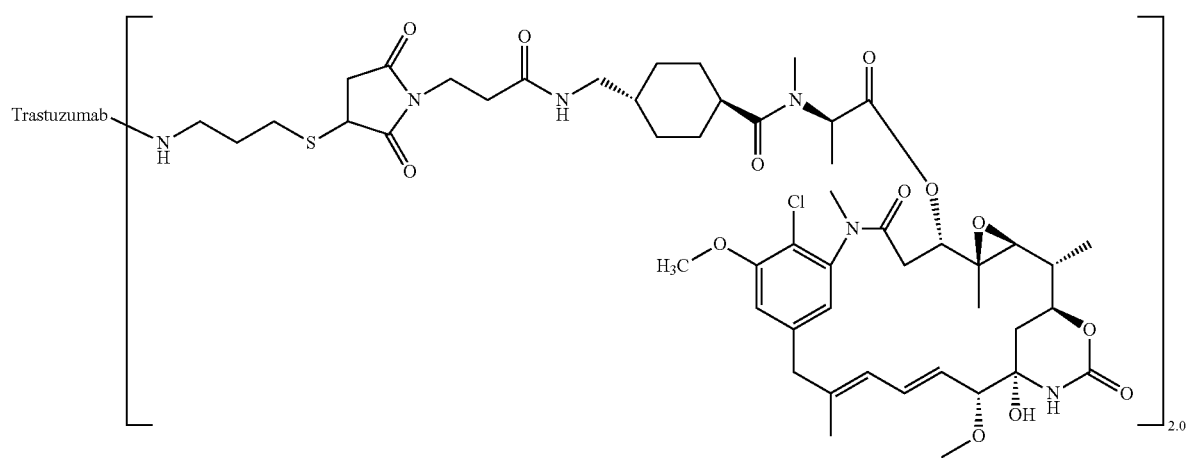
20
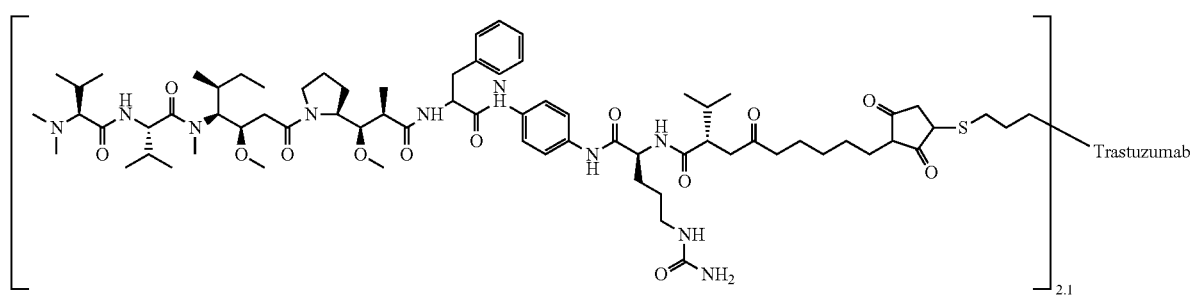
21
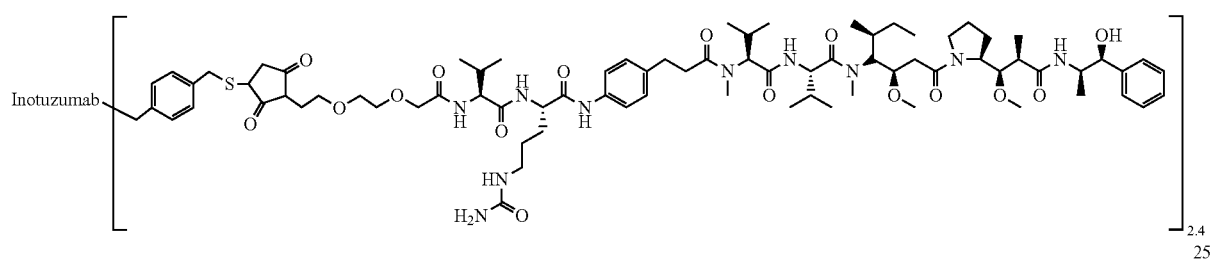
24
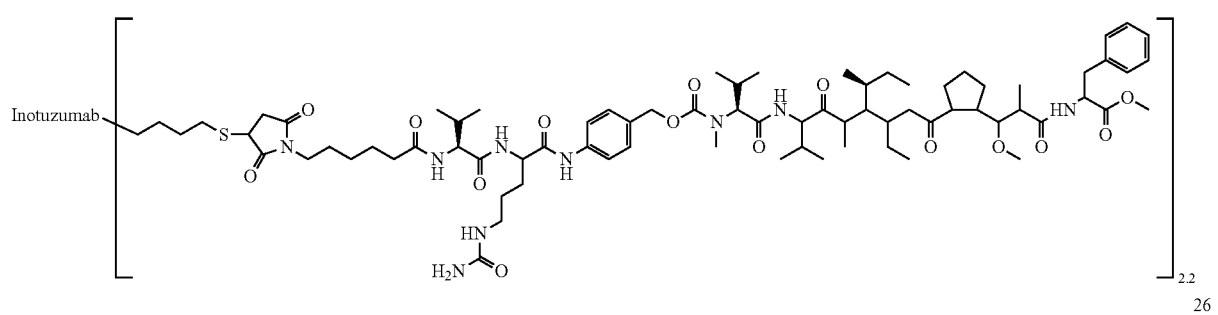
25
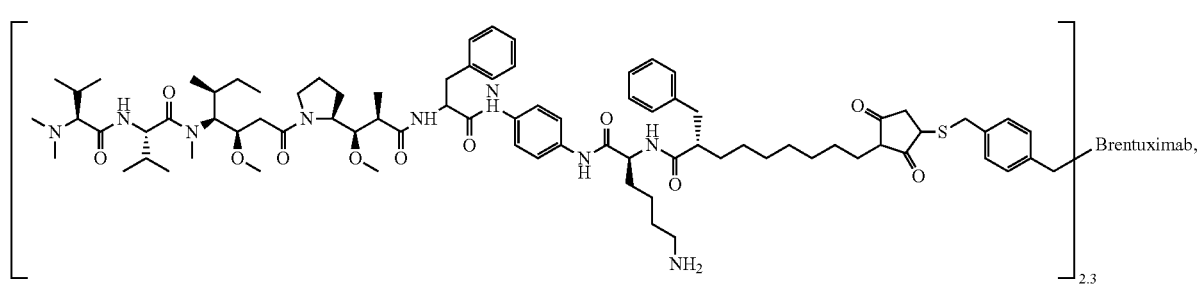
26

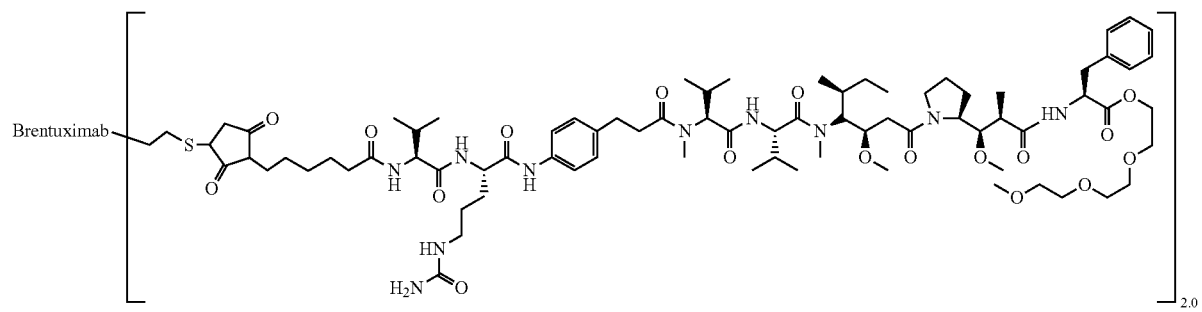
27
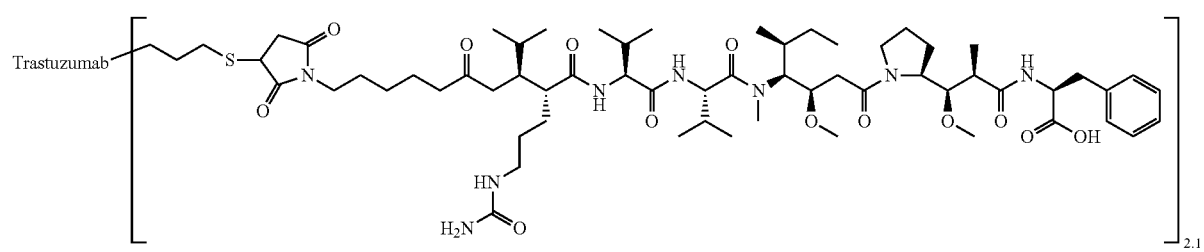
29
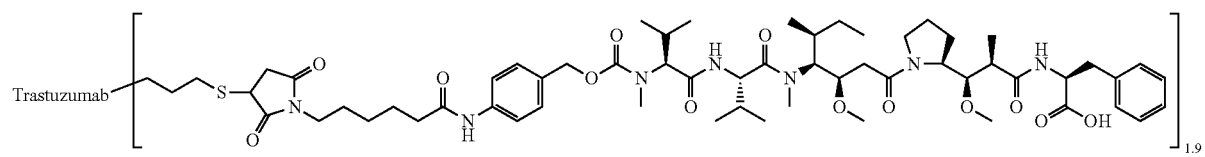
30
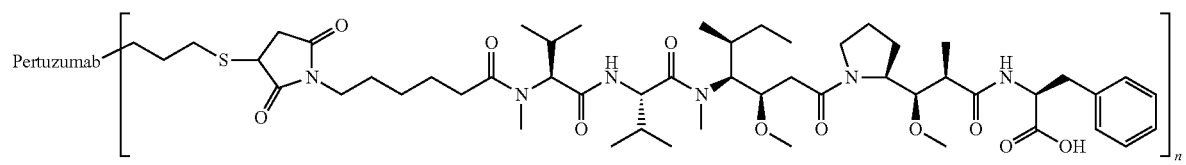
31
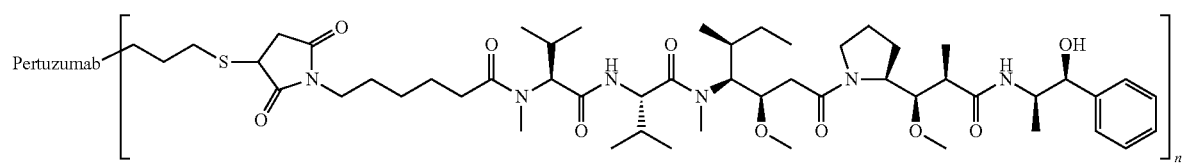
32
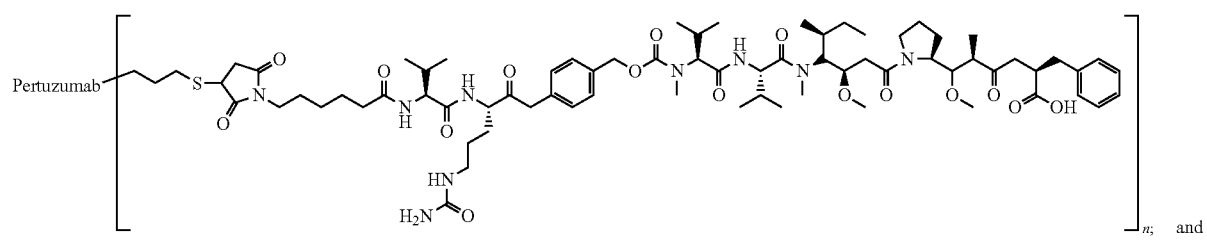
33; and

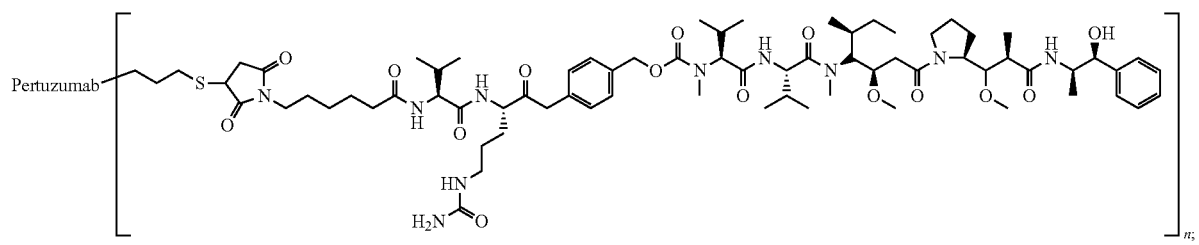

n is selected from 1 to 8, preferably 1 to 4.

The present invention further relates to a process of preparing an antibody-cytotoxic drug conjugate of formula (III),

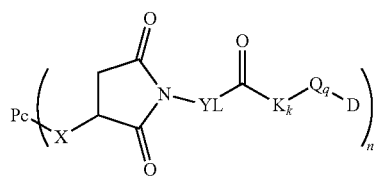

the process comprises the steps of:

1) adding a reducing agent RA to a compound of formula IA and a compound of formula IB, performing the reaction under a condition of reaction system pH of 3-6 and reaction temperature of 0-40° C., and obtaining a compound of formula IC,

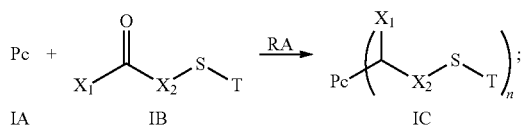

wherein T is selected from the group consisting of tertiary butyl, acetyl, n-propionyl, isopropionyl, triphenylmethyl, methoxymethyl and 2-(trimethylsilyl) ethoxymethyl, preferably acetyl;

2) under the condition of reaction temperature of 0-40° C., adding a deprotecting agent to a compound of formula IC to remove the protective group T of the thiol group and obtaining a compound of formula ID,

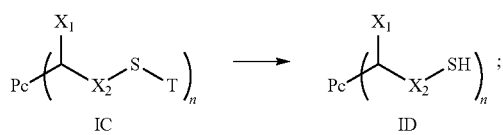

3) under the condition of reaction temperature of 0-40° C., performing a Michael addition reaction between a compound of formula ID and a compound of formula IE, and obtaining a compound of formula (III),

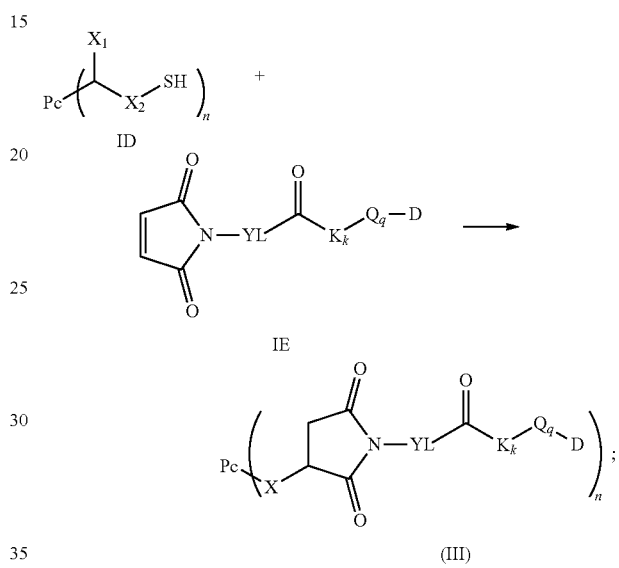

wherein the reaction temperature is preferably 15-30° C., most preferably 20-25° C.; the deprotecting agent is preferably hydroxylamine hydrochloride; the reducing agent RA is preferably sodium cyanoborohydride or sodium triacetoxyborohydride;

wherein $X_1$ and $X_2$ are as defined in formula X; Pc is a ligand; T and n are as defined in formula (II); YL, $K_k$, and $Q_q$ are as defined in formula (Y), and D is a cytotoxic drug.

The present invention further relates to a pharmaceutical composition, wherein the pharmaceutical composition comprises a therapeutically effective amount of the ligand-cytotoxic drug conjugate or pharmaceutically acceptable salt or solvate thereof as described above, and one or more pharmaceutically acceptable carriers, diluents or excipients.

The present invention further relates to the use of the ligand-cytotoxic drug conjugate or pharmaceutically acceptable salt or solvate thereof, or the pharmaceutical composition described above, in the preparation of a medicament for the treatment of cancer, wherein the cancer is a tumor-associated receptor overexpressing cancer, wherein the tumor-associated receptor is one or more selected from the group consisting of (1)-(8):

1) HER2(ErbB2),
2) CD22,
3) CD30,
4) CD33,
5) CD44,
6) CD56,
7) Lewis Y, and
8) GPNMB.

The present invention further relates to a method for modulating a receptor in vitro, the method comprises administering to a subject to be tested an effective amount of the ligand-cytotoxic drug conjugate or pharmaceutically acceptable salt or solvate thereof, or the pharmaceutical composition described above, the receptor is selected from the group consisting of:
1) HER2(ErbB2),
2) CD22,
3) CD30,
4) CD33,
5) CD44,
6) CD56,
7) Lewis Y, and
8) GPNMB.

The present invention further relates to a method for treating cancer in mammals, the method comprises administering to the mammal a therapeutically effective amount of the ligand-cytotoxic drug conjugate or pharmaceutically acceptable salt or solvate thereof, or the pharmaceutical composition described above, wherein the mammal is human, the cancer is selected from the group consisting of breast cancer, ovarian cancer, stomach cancer, endometrial cancer, salivary gland cancer, lung cancer, colon cancer, renal cancer, colorectal cancer, thyroid cancer, pancreatic cancer, prostate cancer, bladder cancer, acute lymphocytic leukemia, acute myeloid leukemia, acute promyelocytic leukemia, chronic myelogenous leukemia, chronic lymphocytic leukemia, Hodgkin's lymphoma, non-Hodgkin's lymphoma and relapsed anaplastic large cell lymphoma, preferably breast cancer, Hodgkin's lymphoma or relapsed anaplastic large cell lymphoma; more preferably HER2 over-expressing breast cancer of 2+ level or higher level, most preferably breast cancer associated with HER2 expression.

The present invention further relates to the use of a compound of formula (IV), a tautomer, mesomer, racemate, enantiomer, diastereomer, or mixture thereof, or a pharmaceutically acceptable salt thereof, in the preparation of a medicament for the treatment of cancer:

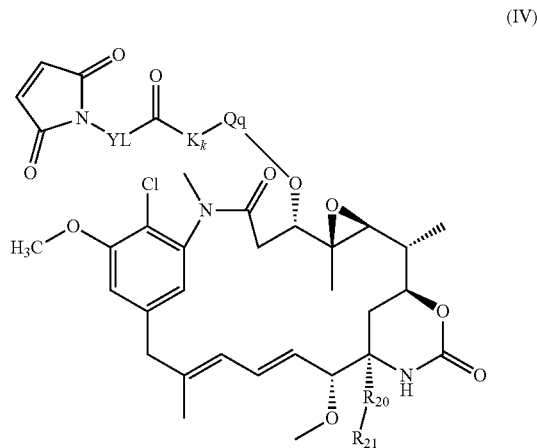

(IV)

wherein:
YL is selected from the group consisting of alkyl, cycloalkyl, O-alkyl, O-alkoxy, aryl, alkyl-cycloalkyl, cycloalkyl-alkyl, alkyl-aryl, alkyl-cyclo alkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, $CH_2(OCH_2CH_2)_t$, $(CH_2CH_2O)_tCH_2$, and $(CH_2CH_2O)_t$, t is an integer selected from 1 to 10, preferably an alkyl group, more preferably $C_2$-$C_8$ linear alkyl;

$K_k$ is an amino acid unit, wherein K is an amino acid, k is an integer selected from 0 to 10, preferably k is 2, $K_k$ is preferably valine-citrulline;

Qq is an extended unit, wherein q is 0, 1 or 2;

$R_{20}$ is O or S;

$R_{21}$ is selected from the group consisting of H, alkyl, cycloalkyl, heterocyclyl, aryl, and heteroaryl, wherein the alkyl, cycloalkyl, heterocyclyl, aryl and heteroaryl are independently and optionally substituted with one or more groups selected from the group consisting of halogen, hydroxy, cyano, nitro, alkyl, alkoxy, cycloalkyl, heterocyclyl, aryl, and heteroaryl.

After linking an N-terminal amino group and/or the amino group of a lysine residue of the antibody according to the present invention to the connecting unit X having a free thiol group, a reduction reaction is avoided in the antibody hinge region, thereby decreasing the impact on the structure of the antibody itself. In addition, the introduced carbon-nitrogen bond structure is stable, not easily broken down during circulation in the body, and the Drug to Antibody Ratio can be controlled within the normal distribution of 0-5 by further controlling the reaction condition.

DETAILED DESCRIPTION OF THE INVENTION

Unless otherwise defined, all technical and scientific terms used herein are in accordance with those commonly understood by one of ordinary skill in the art. Although similar or equivalent methods and materials may also be used to implement or test the present invention, the present disclosure describes the preferred methods and materials. The following terms are used to describe and claim the present invention according to the following definitions.

When trade names are used in this invention, it is intended to include the preparations, the generic drug products and active drug moieties under the trade names.

Unless specified otherwise, the terms used in the specification and claims have the following meanings.

The term "alkyl" refers to a saturated aliphatic hydrocarbyl group including $C_1$-$C_{20}$ linear or branched groups, preferably an alkyl having 1 to 12 carbon atoms, more preferably an alkyl having 1 to 10 carbon atoms, most preferably an alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. A lower alkyl having 1 to 6 carbon atoms is more preferred. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point, and the substituent group(s) is preferably one or more groups independently selected from the group consisting of alkyl, alkenyl, alkynyl, alkyloxyl, alkylthiol, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocycloalkylthio, and oxo.

The term "Cycloalkyl" refers to a saturated or partially unsaturated monocyclic or polycyclic hydrocarbyl group. Cycloalkyl has 3 to 20 carbon atoms, preferably 3 to 12 carbon atoms, more preferably 3 to 10 carbon atoms, most preferably 3 to 8 carbon atoms. Representative examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes cycloalkyl having a spiro ring, fused ring or bridged ring.

The term "Heterocyclyl" refers to a saturated or partially unsaturated monocyclic or polycyclic hydrocarbon substituent having 3 to 20 cyclic atoms, wherein one or more cyclic atoms are heteroatoms selected from the group consisting of N, O, and $S(O)_m$ (wherein m is an integer between 0 and 2), but excluding —O—O—, —O—S— or —S—S— in the ring, and the remaining cyclic atoms are C atoms. 3 to 12 cyclic atoms are preferred, wherein 1 to 4 atoms are heteroatoms; 3 to 10 cyclic atoms are more preferred. Representative examples of monocyclic heterocyclyl include, but are not limited to, pyrrolidinyl, piperidyl, piperazinyl, morpholinyl, thiomorpholinyl, homopiperazinyl, and the like. Polycyclic heterocyclyl includes the heterocyclyl having a spiro ring, fused ring or bridged ring.

The ring of said heterocyclyl can be fused to the ring of an aryl, heteroaryl or cycloalkyl, wherein the ring bound to the parent structure is heterocyclyl. Representative examples include, but are not limited to the following groups:

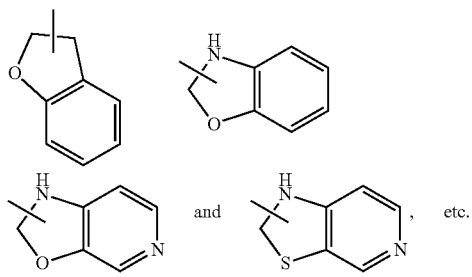

The heterocyclyl can be optionally substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, and oxo group.

The term "aryl" refers to a 6- to 14-membered all-carbon monocyclic ring or fused polycyclic ring (that is, the rings share the adjacent carbon atom pair), which has a conjugated n-electron system. The aryl is preferably 6- to 10-membered, such as phenyl and naphthyl, preferably phenyl. The aryl ring can be fused to the ring of a heteroaryl, heterocyclyl or cycloalkyl, wherein the ring bound to the parent structure is aryl. Representative examples include, but are not limited to, the following groups:

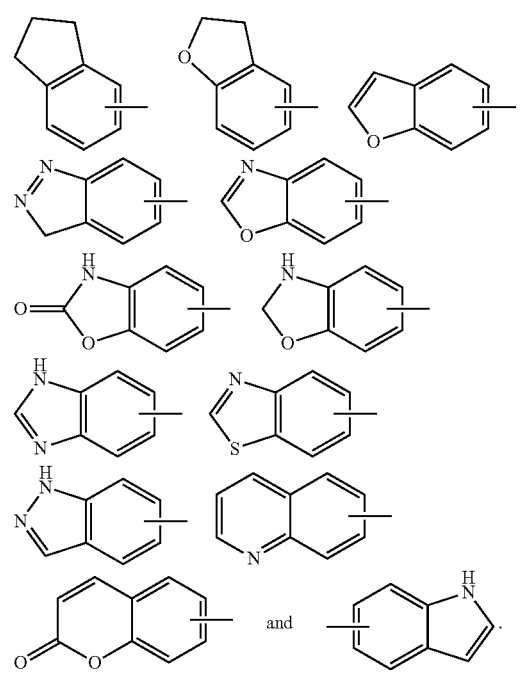

The aryl group can be substituted or unsubstituted. When substituted, the substituent group(s) is preferably one or more groups independently selected from the group consisting of alkyl, alkenyl, alkynyl, alkoxy, alkylthiol, alkylamino, halogen, thiol, hydroxy, nitro, cyano, cycloalkyl, heterocycloalkyl, aryl, heteroaryl, cycloalkoxy, heterocycloalkoxy, cycloalkylthio, and heterocycloalkylthio.

The term "heteroaryl" refers to a heteroaromatic system having 1 to 4 heteroatoms and 5 to 14 cyclic atoms, wherein the heteroatoms are selected from the group consisting of O, S, and N. The heteroaryl is preferably 5- to 10-membered, more preferably 5- or 6-membered, such as furyl, thienyl, pyridinyl, pyrrolyl, N-alkyl pyrrolyl, pyrimidinyl, pyrazinyl, imidazolyl, tetrazolyl, and the like. The heteroaryl can be fused with the ring of an aryl, heterocyclyl or cycloalkyl, wherein the ring bound to the parent structure is heteroaryl. Representative examples include, but are not limited to, the following groups:

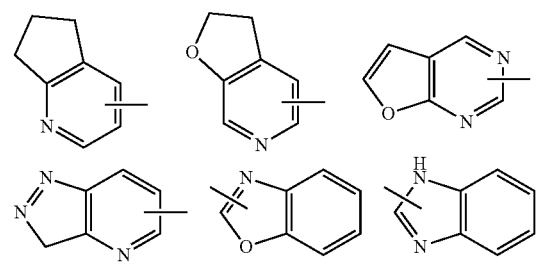

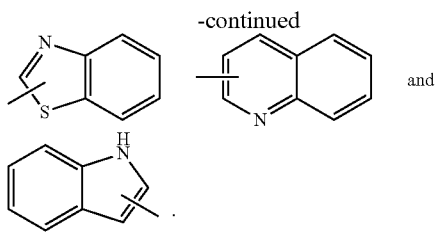

The heteroaryl group can be optionally substituted or unsubstituted. When substituted, the substituent group(s) is preferably one or more groups independently selected from the group consisting of alkyl, alkenyl, alkynyl, alkoxy, alkylthiol, alkylamino, halogen, thiol, hydroxy, nitro, cyano, cycloalkyl, heterocycloalkyl, aryl, heteroaryl, cycloalkoxy, heterocycloalkoxy, cycloalkylthio, and heterocycloalkylthio.

The term "alkoxy" refers to both an —O-(alkyl) and an —O-(unsubstituted cycloalkyl) group, wherein the alkyl is as defined above. Representative examples of alkoxy include, but are not limited to, methoxy, ethoxy, propoxy, butoxy, cyclopropyloxy, cyclobutyloxy, cyclopentyloxy, and cyclohexyloxy. The alkoxy can be optionally substituted or unsubstituted. When substituted, the substituent is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocycloalkyl, aryl, heteroaryl, cycloalkoxy, heterocyclic alkoxy, cycloalkylthio, and heterocyclic alkylthio.

The term "bond" refers to a covalent bond presented as "—".

The term "Hydroxy" refers to an —OH group.

The term "Halogen" refers to fluoro, chloro, bromo or iodo atoms.

The term "Amino" refers to an —NH$_2$ group.

The term "Cyano" refers to a —CN group.

The term "Nitro" refers to a —NO$_2$ group.

The term "Oxo group" refers to a =O group.

The term "Carboxyl" refers to a —C(O)OH group.

The term "Alkoxycarbonyl" refers to a —C(O)O(alkyl) or (cycloalkyl) group, wherein the alkyl is as defined above.

The term "benzyl" refers to a methyl benzene group:

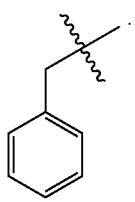

The term "Optional" or "optionally" means that the event or circumstance described subsequently can, but need not occur, and the description includes the instances in which the event or circumstance does or does not occur. For example, "the heterocyclic group optionally substituted with an alkyl" means that an alkyl group can be, but need not be, present, and the description includes the case wherein the heterocyclic group is substituted with an alkyl and the case wherein the heterocyclic group is not substituted with an alkyl.

"Substituted" refers to one or more hydrogen atoms in the group, preferably up to 5, more preferably 1 to 3 hydrogen atoms, each independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxy group having free hydrogen and carbon atoms having unsaturated bonds (such as olefinic) may be unstable.

The term "pharmaceutical composition" refers to a mixture of one or more of the compounds described in the present invention or physiologically/pharmaceutically acceptable salts or prodrugs thereof, and other chemical components such as physiologically/pharmaceutically acceptable carriers and excipients. The purpose of a pharmaceutical composition is to facilitate administration of a compound to an organism, and to help the absorption of the active ingredient, thus displaying biological activity.

The term "pharmaceutically acceptable salt" refers to a salt form of a ligand-cytotoxic drug conjugate of the present invention, the salt is safe and effective, and has the biological activity required by mammals in vivo. The antibody-drug conjugate compound of the present invention comprises at least one amino group, which can form a salt with acid. Non-limiting examples of pharmaceutically acceptable salts include: hydrochloride, hydrobromide, hydroiodide, sulfate, bisulfate, citrate, acetate, succinate, ascorbate, oxalate, nitrate, pears salts, hydrogen phosphate, dihydrogen phosphate, salicylate, hydrogen citrate, tartrate, maleate, fumarate, formate, benzoate, methanesulfonate, ethanesulfonate, benzenesulfonate, and p-toluenesulfonate.

The term "solvate" refers to a pharmaceutically acceptable solvent formed by a ligand-drug conjugate compound of the present invention with one or more solvate molecule(s). Non-limiting examples of solvate molecules include: water, ethanol, acetonitrile, isopropyl alcohol, DMSO, and ethyl acetate.

The term "ligand" is a macromolecular compound able to recognize and bind to the target cell-associated antigens or receptors. The role of the ligand is to deliver the drug to the target cell population bound to the ligand. The ligand includes, but is not limited to, proteinaceous hormones, lectins, growth factors, antibodies and other molecules capable of binding to cells. In an embodiment of the present invention, the ligand is expressed as Pc. A connecting bond can be formed between a hetero atom in the ligand and the connecting unit.

The term "antigen or receptor" is used by a ligand to recognize and bind to target cells. In the present invention, ligands against cell surface antigens or receptors expressed on the target cells and/or tissue of proliferative diseases, such as cancer, are preferred. Non-limiting embodiments of cell surface receptors are selected from the cell surface receptors of HER2, HER3, HER4, CD20, CD22, CD30, CD33, CD44, Lewis Y, CD56, CD105, VEGFR and GPNMB. Most preferably are those selected from the group of cell surface receptors of HER2, CD22, CD30, CD33, CD44, CD56, Lewis Y, and GPNMB. Specifically, preferred non-limiting embodiments include: Trastuzumab (HER2), Inotuzumab (CD22), Pinatuzumab (CD22), Brentuximab (CD30), Gemtuzumab (CD33), Bivatuzumab (CD44), Lorvotuzumab (CD56), cBR96 (Lewis Y) and Glematumamab (GPNMB).

As used herein, "antibody" refers to any form of antibody exhibiting the desired biological activity. Therefore, it is used in the broadest sense, in particular, including but not limited to full length antibodies, and antibody binding fragments or derivatives thereof. Sources of antibodies include, but are not limited to, monoclonal antibodies, polyclonal antibodies, and genetically engineered antibodies (e.g., bispecific antibodies).

The term "full-length antibody" refers to an immunoglobulin polymer (such as IgM) comprising 4 polypeptide chains (that is, 2 heavy chains and 2 light chains) crosslinked by disulfide bonds. Each heavy chain comprises a fragment of a heavy chain variable region (abbreviated as VH) and a fragment of a heavy chain constant region. A heavy chain constant region comprises three domains: CH1, CH2 and CH3. Each light chain comprises a fragment of a light chain variable region (referred as VL) and a fragment of light chain constant region. The light chain constant region comprises one domain (CL1). VH and VL regions can be further divided into hypervariable regions, which are termed as complementarity determining regions (CDRs). More conserved domains, referred to as the framework region (FR), are interspersed among the complementarity determining regions.

The term "antibody binding fragment or derivative" includes any naturally occurring, enzymatically obtained, synthesized, or genetically engineered polypeptide or glycoprotein that can bind to an antigen and form a complex. Typically it comprises at least part of the antigen binding region or variable region (e.g., one or more CDRs) of the parent antibody, and retains at least some binding specificity of the parental antibody. "Antibody binding fragment or derivative" can be derived from the antibody, e.g., obtained by reforming the full-length antibody by appropriate standard techniques including proteolytic or recombinant gene engineering techniques (including manipulation and expression of DNA expressing the antibody variable region and part of the constant region). "Antibody binding fragment or derivative" includes, but is not limited to: (i) Fab fragments; (ii) F(ab')$_2$ fragments; (iii) Fd fragments; (iv) Fv fragments; (V) single-chain Fv (scFv); (vi) dAb fragments; and (vii) minimal recognition unit of the mimic amino acid residues of the antibody hypervariable region (e.g. an isolated complementarity determining region (CDR)). Other engineering molecules such as bivalent antibodies, trivalent antibodies, tetravalent antibodies and microantibodies are within the scope of "antibody binding fragment or derivative".

"Fab fragment" consists of a complete light chain and heavy chain VH and CH1 functional domains. The heavy chain of a Fab molecule cannot form a disulfide bond with another heavy chain molecule.

"Fc" region contains two heavy chain fragments comprising the antibody CH1 and CH2 domains. The two heavy chain fragments are held together by two or more disulfide bonds and the hydrophobic effect of the CH3 domain.

"Fab' fragment" contains light chain and heavy chain VH and CH1 functional regions, and further comprises the region between the CH1 domain and CH2 domain, so that a disulfide bond can be formed between the two heavy chains of two Fab' fragments to forma F(ab')$_2$ molecule.

"F(ab')$_2$ fragment" contains two light chains and two heavy chains containing a partial constant region between the CH1 domain and CH2 domain, so that an interchain disulfide bond can be formed between the two heavy chains. Therefore, a F(ab')$_2$ fragment consists of two Fab' fragments held together via the disulfide bond between the two heavy chains.

"Fv fragment" comprises a light chain or/and heavy chain variable region (VH) functional domain.

"Fc region" corresponds to CH2 and CH3 functional domains of IgG, without any antigen-binding activity. It is the part of the antibody molecule that interacts with effector molecules and cells.

"Hinge region" is used to link the antibody Fab fragment with the Fc fragment. In the present invention, a bispecific fusion protein can be connected to the Fc fragment.

The antibody of the present invention is preferably an antibody that specifically binds to the cell surface antigen of target cells. Non-limiting embodiments include the following antibodies:

Antibodies against cell surface antigen HER2 (most existing on the surface of breast cancer cells); antibodies against most CD20 or CD22 antigen over-expressing B cell lymphomas; antibodies against cell surface antigen CD33 (the cell surface antigen is prevalent in some human myeloma, especially in acute myeloid leukemia); antibodies against cell surface antigens CD30, CD44, Lewis Y, CD56, CD105, VEGFR or GPNMB; in addition, other commercially available antibodies such as trastuzumab (trade name Herceptin®) can also be used as a ligand. Trastuzumab is a humanized anti-HER2 antibody used for treatment of breast cancer, and for treatment of HER2 overexpressing metastatic breast cancer.

The term "identity" refers to sequence similarity between two polynucleotide sequences or two polypeptides. When the positions of two aligned sequences are occupied by the same base or amino acid monomeric subunit, e.g., if each position of two DNA molecules is occupied by adenine, then the two molecules are identical at that position. Identical percentage between two sequences is presented as a function: common matched or identical position numbers of the two sequences divided by the compared position numbers ×100. For example, in sequence optimal alignment, if six positions are matched or identical out of 10 positions of two sequences, then the identity of the two sequences is 60%. Generally, the two sequences are compared to obtain the largest identity percentage.

The term "interval unit" (Y) is a bifunctional compound used to connect the ligand of the present invention and the cytotoxic drug to form a ligand-Interval Unit-drug conjugate, or it is used to form an anti-tumor associated antigen immunoconjugate. Such immunoconjugate can selectively deliver cytotoxic drugs to tumor cells.

The term "cytotoxic drug" means a chemical molecule capable of strongly destructing normal growth in tumor cells. In principle, cytotoxic drugs can kill tumor cells in high enough concentrations, but due to the lack of specificity, when killing tumor cells, it also leads to apoptosis in normal cells, leading to serious side effects. In an embodiment of the present invention, the cytotoxic drug is represented as D, and non-limiting examples include tubulin inhibitors, DNA alkylating agents, tyrosine kinase inhibitors, topoisomerase inhibitors, and DNA synthesis inhibitors, preferably tubulin inhibitors.

Auristatins are completely synthetic drugs, with a relatively easily formed chemical structure that facilitates the optimization of physical properties and druggability. Auristatins derivatives used for antibody conjugation include monomethyl auristatin E (MMAE) and monomethyl auristatin F (MMAF), and the former is a synthetic pentapeptide derived from natural tubulin polymerase inhibitor dolastatin-10, synthesized by adding 2-amino-1-ol-phenyl-propyl at the C-terminus MMAE inhibitory activities against a variety of human tumor cell lines are less than one nanomolar. In order to reduce the cytotoxic activity of MMAE itself, for MMAF, a phenylalanine is introduced at the C-terminus of dolastatin-10. Due to the introduction of a carboxyl group in the structure, MMAF has poor capacity in passing through the membrane, and therefore the biological activity against cells is significantly decreased, but the inhibitory activity against cells after conjugation to an antibody is increased substantially (U.S. Pat. No. 7,750, 116).

The term "tubulin inhibitor" refers to a class of compounds that exert an anti-tumor effect by inhibiting or promoting polymerization of tublin, and consequently interfering with the cell mitosis process. Non-limiting examples include maytansinoids, calicheamicins, taxanes, vincristines, colchicines, and Dolastatins/Auristatins, preferably maytansinoids or Dolastatins/Auristatins; more preferably compounds of formula $D_1$ or $D_M$.

The term "DNA alkylating agent" refers to a class of compounds that can form a carbocation or other positive ion or other active electrophilic group in the body and further covalently bind with a group containing abundant electrons in DNA in cells (such as amino, mercapto, hydroxy, carboxyl, phosphoryl etc.), causing DNA structural change or breakage, and consequently lead to tumor cell death. Non-limiting examples include nitrogen mustards (cyclophosphamide), ethylidenehydrazono amines (thiotepa, mitomycin), methanesulfonates (busulfan), polyols (dibromannitol), nitrosoureas (carmustine), triazene imidazoles (dacarbazine) and hydrazines (procarbazine).

The term "tyrosine kinase inhibitor" refers to a class of competitive inhibitors that can bind to a tyrosine kinase, such as adenosine triphosphate (ATP), and also refers to a class of compounds that block tyrosine kinase activity and inhibit cell proliferation as tyrosine analogs. Non-limiting examples include imatinib, gefitinib, erlotinib, sunitinib, sorafenib, lapatinib, dasatinib, nilotinib and so on.

The term "protein synthesis inhibitor" refers to a class of compounds that can affect the protein synthesized by the target cell. Protein synthesis inhibitors may act on each step of protein synthesis, such as DNA replication and RNA transcription, and play a role by inhibiting the initiation factors, elongation factors and ribosomes. Non-limiting examples include aminoglycosides, tetracyclines, macrolides, and chloramphenicols.

The term "Drug to Antibody Ratio" means the average number of cytotoxic drugs loaded on each ligand of the above formula (I), and can also be represented as ratio of drug amount and antibody amount. The range of drug loading for each ligand (Pc) can be 1-8 cytotoxic drugs (D). In the embodiment of the present invention, the Drug to Antibody Ratio is represented as n. The average number of drugs in each ADC molecule after the coupling reaction can be identified by conventional methods, such as UV/visible spectroscopy, mass spectrometry, ELISA test, and HPLC characteristic identification.

In the present invention, n may be restricted by the number of connecting sites. In one embodiment of the present invention, the cytotoxic drug is conjugated at the N-terminal amino group and/or ε-amino of lysine residues via a connecting unit. In general, the number of drug molecules which is conjugated to the antibody in the coupling reaction will be less than the theoretical maximum.

The following non-limiting methods can be used to control the loading amount of the ligand cytotoxic drug conjugate, comprising:

(1) controlling the molar ratio of connecting reagents and MAb,
(2) controlling the reaction time and temperature,
(3) selecting different reaction reagents.

The term "connecting unit" refers to a chemical structure fragment which is covalently linked to the ligand through a carbon atom at one end and is covalently linked to the cytotoxic drugs through a sulfur atom at the other end. In the present invention, the connecting unit is defined as general formula (X). The connecting unit is linked to the amino group of the antibody via reductive amination, preferably to the N-terminus of the antibody and/or to the ε-amino of the lysine residues.

The term "interval unit" is a bifunctional compound fragment, used to couple the connecting unit with the cytotoxic drug and finally form a ligand-cytotoxic drug conjugate. Such coupling manner can selectively deliver the cytotoxic drugs to the connecting unit. In the present invention, an interval unit is preferably shown as the general formula (Y).

The term "amino acid unit" means that when an extended unit exists, the carbonyl group of the following structural formula $Y_R$ can be connected with the extended unit. When no extended unit exists, the $Y_R$ is directly connected to the amino acid on the cytotoxic drug. In embodiments of the present invention, the amino acid unit is represented as —$K_k$—.

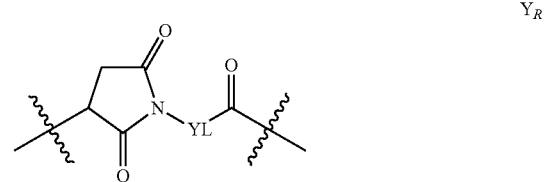

$Y_R$

—$K_k$— is a dipeptide, tripeptide, tetrapeptide, pentapeptide, hexapeptide, heptapeptide, octapeptide, nonapeptide or decapeptide. —K— units each independently comprise the following structural formula $K_a$ or $K_b$, k is an integer from 0-10:

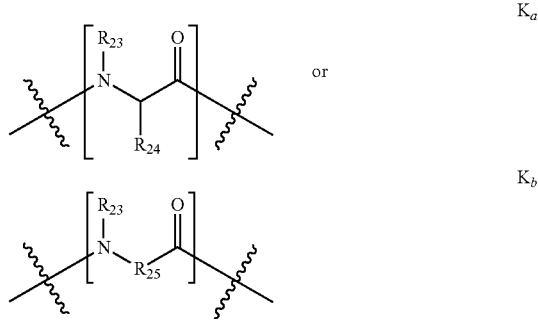

$K_a$ or $K_b$ wherein:
$R_{23}$ is —H or methyl;
$R_{24}$ is H, methyl, isopropyl, isobutyl, sec-butyl, benzyl, p-hydroxy benzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, or cyclohexyl,

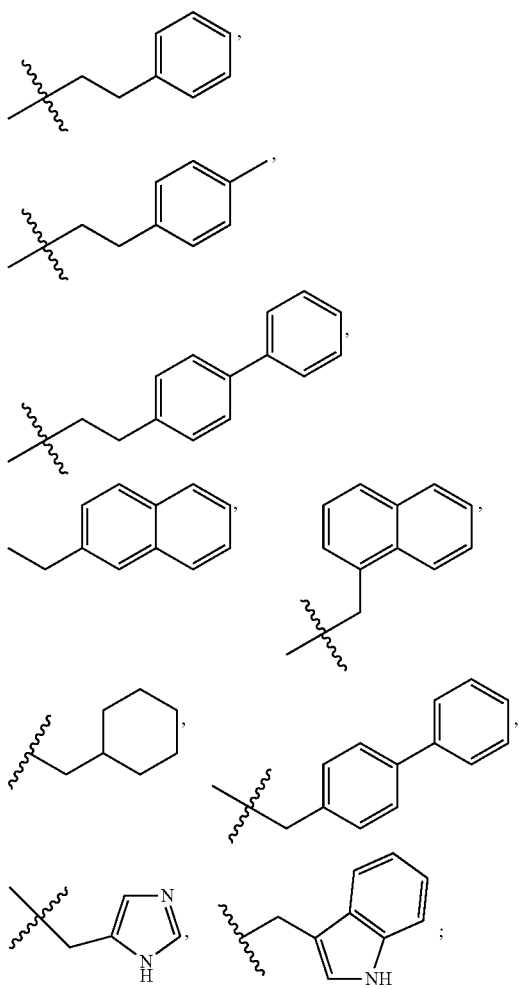

R$_{25}$ is -aryl-, -alkyl-aryl-, -cycloalkyl-, -alkyl-cycloalkyl-, -cycloalkyl-alkyl-, -alkyl-cycloalkyl-alkyl-, -heterocyclyl-, -alkyl-heterocyclyl-, -heterocyclic-alkyl-, -alkyl-heterocyclic-alkyl-, -aryl-, -alkyl-aryl-, -aryl-alkyl-, -alkyl-aryl-alkyl-, -heteroaryl-, -alkyl-heteroaryl-, -heteroaryl-alkyl-, or -alkyl-heteroaryl-alkyl-.

In one embodiment, —K$_k$— is a dipeptide, preferably -valine-citrulline-, -phenylalanine-lysine- or —N-methyl valine-citrulline-, and more preferably -valine-citrulline-.

In another embodiment, —K$_k$— is a dipeptide, preferably

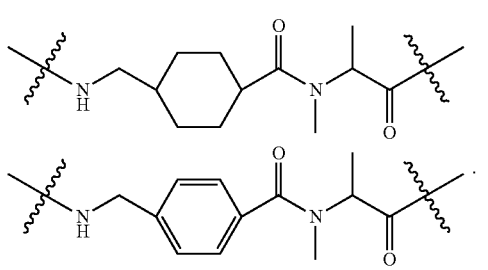

The term "amino acid" refers to an organic compound of which the molecular structure contains amino and carboxyl groups, and amino and carboxyl groups are directly connected to the —CH— structure. The formula is H$_2$NCHRCOOH. According to the linkage position of the amino group to the carbon atom, it can be divided into α, β, γ, δ, ε . . . -amino acids. In the biological field, the amino acids that constitute native protein structures have specific characteristics, that is the amino group is attached directly to the α-carbon atom, namely α-amino acids, including Gly (Glycine), Ala (Alanine), Val (Valine), Leu (leucine), Ile (isoleucine), Phe (phenylalanine), Trp (tryptophan), Tyr (tyrosine), Asp (aspartic acid), His (histidine), Asn (asparagine), Glu (glutamic acid), Lys (lysine), Gln (glutamine), Met (methionine), Arg (arginine), Ser (serine), Thr (threonine), Cys (cysteine), Pro (proline) and the like.

In one embodiment of the present invention, the amino acid is selected from

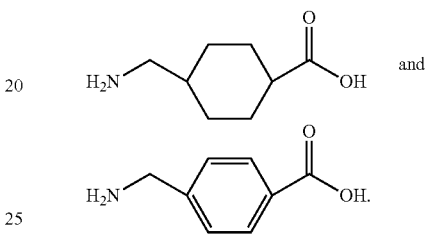

The term "extended unit" refers to the case when the amino acid unit is present, it can couple the amino acid unit with the cytotoxic drug, or when the amino acid unit is absent, the extended unit can be a chemical structure conjugated to the cytotoxic drug by the carbonyl group of Y$_R$. In the embodiment of the present invention, the extended unit is represented as -Qq-, and q is 0, 1, or 2.

In one preferred embodiment, Q is a para-amino benzyl alcohol structure. In this embodiment, the potential mechanism of drug release in vivo is shown in Scheme 1 (Toki B E, Cerveny C G, *J Org. Chem.* 2002 (67) 1866-1872):

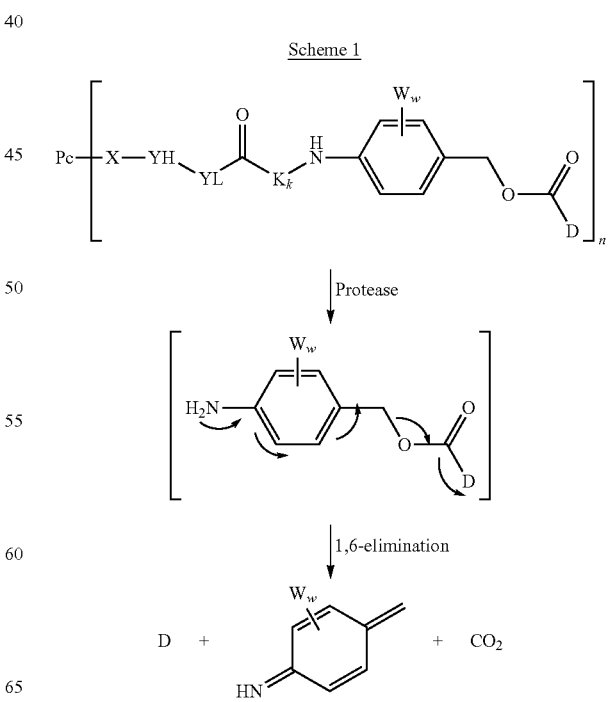

wherein:

W is $C_1$-$C_8$ alkyl, halogen, nitro or cyano; and w is an integer selected from 0-4.

Preparation of conventional pharmaceutical compositions is shown in Chinese pharmacopoeia.

The term "carrier" is applied for the drug of the present invention, and refers to a system that can change the manner in which a drug enters the human body, and change the in vivo distribution, control the release rate of the drug, and delivery of the drug to the target organ. Drug carrier release and targeting systems are capable of reducing drug degradation and loss, decreasing side effects, and improving bioavailability. For example, a macromolecular surfactant used as a carrier can self-assemble to form aggregates in various forms because of its unique amphiphilic structure, and preferred examples include micelles, emulsions, gels, liquid crystals, vesicles, etc. These aggregates not only have the ability to entrap drug molecules, but also display good membrane permeability, and can be used as excellent drug carriers.

The term "excipient" is an appendage other than the main drug in pharmaceutical formulations, also referred to as accessory. For example, binders, fillers, disintegrants, lubricants in tablet; matrix portions in semi-solid formulations such as ointments, and creams; preservatives, antioxidants, flavoring agents, perfuming agents, cosolvents, emulsifiers, solubilizers, tonicity adjusting agents, coloring agents in liquid formulation and the like can be referred to as excipients.

The term "diluent" is also referred to as filler, and its main purpose is to increase the tablet weight and volume. The addition of diluent is not only to ensure a certain volume, but also to reduce the dose deviation of main components and improve the compression moldability of the drug. When pharmaceutical tablets contain an oily component, an absorbent, such as starch, lactose, calcium salts, microcrystalline cellulose and the like must be added to absorb the oil material, and maintain the "dry" state, which facilitates tablet formation.

The pharmaceutical composition can be a sterile injectable aqueous solution form. Practical acceptable vehicles and solvents include water, Ringer's solution and isotonic sodium chloride solution. The sterile injectable preparation can be sterile injectable oil-in-water micro emulsion, wherein the active ingredient is dissolved in the oil phase. For example, the active ingredient is dissolved in a mixture of soybean oil and lecithin. Then, oil solution is added to a mixture of water and glycerol solution and dispersed to form a microemulsion. The injection solution or microemulsion can be injected into a patient's bloodstream by heavy local injection. Or, preferably, the solution and microemulsion are administered in a manner to maintain a constant circulating concentration of the compound of the present invention. In order to maintain such a constant concentration, a continuously intravenous delivery device can be used. An example of such a device is Deltec CADD-PLUS™ 5400 intravenous pump.

The pharmaceutical compositions can be in the form of sterile injectable water or oil suspension for intramuscular and subcutaneous administration. According to known techniques, those suitable dispersing agents or wetting agents described above can be used together with suspending agents to prepare the suspension. The sterile injectable preparation can also be a sterile injectable solution or suspension prepared in a nontoxic parenterally acceptable diluent or solvent, e.g., a solution prepared with 1,3-butanediol. In addition, sterile fixed oils can be conveniently used as a solvent or suspending medium. For this purpose, any fixed blending oil, including synthesized glyceride or diglyceride can be used. In addition, fatty acids, such as oleic acid can be used for the preparation of an injectable solution as well.

The term "reducing agent" is a substance that loses electrons or tends to lose electrons in a redox reaction. Reducing agent itself in a broad sense is also an antioxidant with reducibility, and when being oxidized, its product is referred to as an oxidation product. In an embodiment of the present invention, the reducing agent is represented as RA. Non-limiting examples of reducing agents include $H_2$, carbon (C), carbon monoxide (CO), reduced iron powder (Fe), zinc (Zn), alkali metal (commonly used with Li, Na, K), other active metals (e.g., Mg, Al, Ca, La, etc.), stannous chloride (by $SnCl_2$), oxalic acid, potassium borohydride ($KBH_4$), sodium borohydride ($NaBH_4$), sodium cyanoborohydride ($NaCNBH_3$), sodium triacetoxy borohydride (($CH3COO)_3BHNa$), lithium aluminum hydride ($NaBH_4$), hypophosphorous acid, sodium hypophosphite, and sodium thiosulfate ($Na_2S_2O_3$). The reducing agent of the present invention is preferably sodium cyanoborohydride or sodium triacetoxyborohydride.

The term "mercapto-protecting group" refers to a case in which both a thiol group and other chemical groups are involved in the reaction, in order to ensure that the reaction only occurs at the specific group and prevents the thiol group from being affected, the thiol is protected until the reaction is completed, and then the protective group is removed. In an embodiment of the present invention, the mercapto-protecting group is represented as T. Non-limiting examples of mercapto-protecting groups include -tert-butyl, -acetyl, -n-propionyl, -iso-propionyl, -triphenylmethyl, -methoxymethyl, and -2-(trimethylsilyl) ethoxymethyl, and the mercapto-protecting group of the present invention is preferably acetyl.

The term "cancer", also known as malignant tumor, refers to disorders and diseases caused by an uncontrolled cell growth and proliferation mechanism. According to different occurring locations, pathological features of cancers are different. Non-limiting examples include fibrosarcoma, mucus sarcoma, liposarcoma, chondrosarcoma, osteogenic sarcoma, chordoma, angiosarcoma, endothelial sarcoma, lymphatic sarcoma, lymphatic endothelial sarcoma, synovioma, mesothelioma, leiomyosarcoma, rhabdomyosarcoma, colon carcinoma, colorectal cancer, renal cancer, pancreatic cancer, bone cancer, breast cancer, ovarian cancer, prostate cancer, esophageal cancer, stomach cancer, oral cancer, nasal cancer, laryngeal carcinoma, sweat gland carcinoma, sebaceous gland carcinoma, papillary carcinoma, papillary adenocarcinoma, cystadenocarcinoma, medullary carcinoma, bronchogenic carcinoma, hepatocellular carcinoma, cholangiocarcinoma, choriocarcinoma, cervical cancer, uterine cancer, testicular cancer, small cell lung cancer, non-small cell lung cancer, bladder cancer, epithelial carcinoma, glioma, glioblastoma, astrocytoma, medulloblastoma, craniopharyngioma, ependymoma, pineal tumors, mature blood cells tumor, oligodendroglioma, meningioma cancer, skin cancer, melanoma, neuroblastoma, retinoblastoma, acute lymphoblastic leukemia "ALL", B-cell acute lymphoblastic leukemia, acute lymphocytic T-cell leukemia, acute myelogenous leukemia "AML", acute promyelocytic leukemia "APL", acute monocytic leukemia, acute leukemia, acute primary megakaryocytic leukemia, acute myelomonocytic leukemia, acute non-lymphoid leukemia, acute undifferentiated leukemia, chronic myelogenous leukemia "CML", chronic lymphocytic leukemia "CLL", hairy cell leukemia, multiple myeloma, Hodgkin's lymphoma, and non-Hodgkin's lymphoma.

As used herein, the following abbreviations of the connecting fragments corresponding to the appropriate structure:

MC is a fragment shown as formula (V):

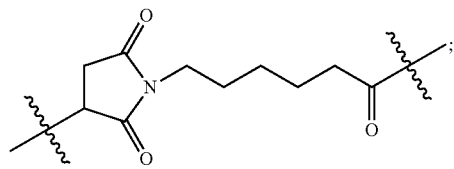

(V)

Val is a valine fragment;
Cit is a citrulline fragment;
PAB is 1,4-aminobenzyl-carbamoyl fragment, which is linked to D, with a structure shown as formula (VI),

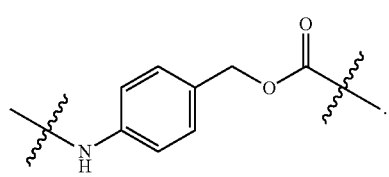

(VI)

As used herein, abbreviations of the following cytotoxic drugs have the definitions shown below:

MMAE is monomethyl-auristatin E (molecular weight: 718), and the structure is shown as formula (VII):

FIG. 2 shows the influence of Compound 16, Compound 17, Compound 18, and the positive control Compound 35 on the weight of tumor-bearing nude mice.

PREFERRED EMBODIMENTS

The invention will be further illustrated with reference to the following specific examples. It is to be understood that these examples are merely intended to demonstrate the invention without limiting the scope of the invention.

Compound structures were identified by Nuclear Magnetic Resonance (NMR) and/or Mass Spectrometry (MS). NMR was determined by a Bruker AVANCE-400 machine. The solvents were deuterated-dimethyl sulfoxide (DMSO-$d_6$), deuterated-chloroform (CDCl$_3$), and deuterated-methanol (CD$_3$OD), with tetramethylsilane (TMS) as an internal standard. NMR chemical shifts ($\delta$) are given in $10^{-6}$ (ppm).

MS was determined by a FINNIGAN LCQAd (ESI) Mass Spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

For thin-layer silica gel chromatography (TLC), Yantai Huanghai HSGF254 or Qingdao GF254 silica gel plates were used. The dimension of the plates used in TLC was 0.15 mm to 0.2 mm, and the dimension of the plates used in product purification was 0.4 mm to 0.5 mm.

For Column chromatography, generally Yantai Huanghai 200 to 300 mesh silica gel was used as carrier.

The known starting materials of the invention can be prepared by conventional synthesis methods in the prior art,

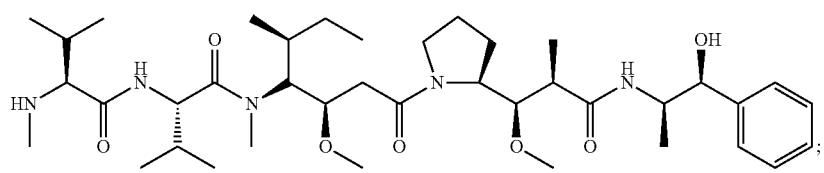

(VII)

MMAF is N-methyl valine-valine-dolaisoleuine (Dil)-dolaproline (Dap)-phenylalanine (MW: 731.5), and the structure is shown as formula (VIII):

or can be purchased from ABCR GmbH & Co. KG, Acros Organics, Aldrich Chemical Company, Accela ChemBio Inc., or Dari Chemical Company, etc.

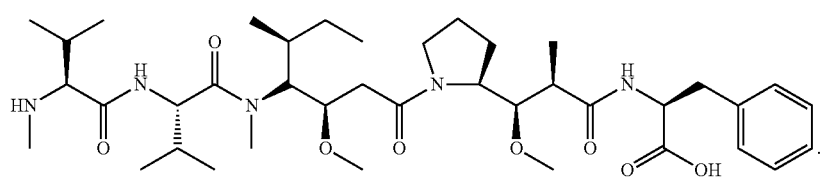

(VIII)

Figure 1:
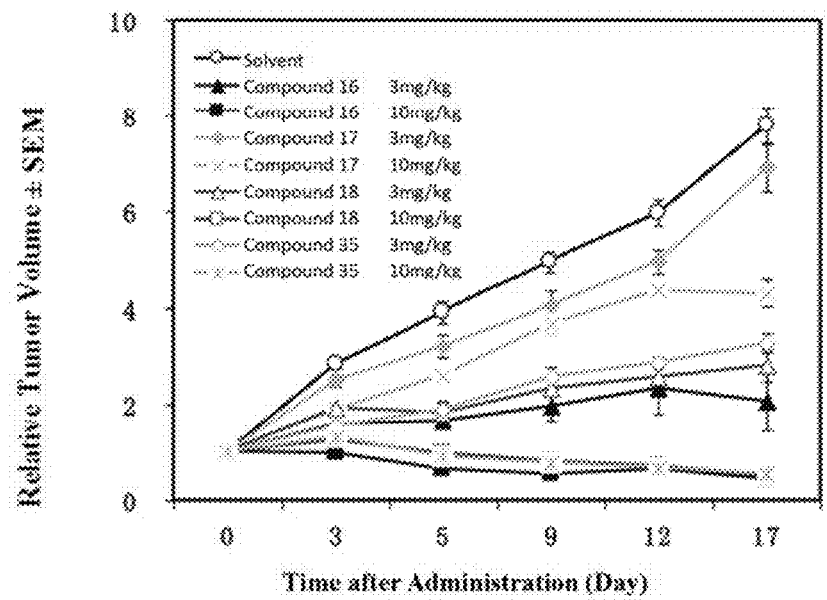
FIG. 1 shows the efficacy of Compound 16, Compound 17, Compound 18, and the positive control Compound 35 on NCI-N87 human gastric cancer xenografts in nude mice; and Unless otherwise stated, the following reactions were performed under nitrogen atmosphere or argon atmosphere.

The term "argon atmosphere" or "nitrogen atmosphere" means that a reaction flask is equipped with a 1 L argon or nitrogen balloon.

Unless otherwise stated, the solution used in the examples refers to an aqueous solution.

Unless otherwise stated, the reaction temperature in the examples was room temperature in the range of 20° C. to 30° C.

The reaction process was monitored by thin layer chromatography (TLC), and the system of developing solvent included A: dichloromethane and methanol system, B: n-hexane and ethyl acetate system, C: petroleum ether and ethyl acetate system, D: acetone. The ratio of the volume of the solvent was adjusted according to the polarity of the compounds.

The elution system for purification of the compounds by column chromatography and the developing solvent by thin layer chromatography included: A: dichloromethane and methanol system, B: n-hexane and ethyl acetate system, C: n-hexane and acetone system, D: n-hexane, E: ethyl acetate. The volume of the solvent was adjusted according to the polarity of the compounds, and sometimes a little triethylamine and acidic or alkaline reagent was also added.

The structures of the compounds of the present invention were determined by Q-TOF LC/MS. For Q-TOF LC/MS, Agilent 6530 Accurate-Mass Quadrupole—Time of Flight Mass Spectrometer and Agilent 1290-Infinity UHPLC (Agilent Poroshell 300SB-C8 5 μm, 2.1×75 mm Column) were used.

Known starting materials of the present invention were synthesized by adopting or using the methods known in the art, and the experimental methods in the following examples for which the specific conditions are not indicated were carried out according to conventional conditions or the conditions recommended by the product manufacturers. The experimental reagents for which the specific sources are not indicated were the conventional reagents generally purchased from market.

Example 1

Preparation of Intermediates

Preparation of Intermediates as Drugs

1. The following intermediate compounds 1-6 were prepared by a method disclosed in PCT Patent Application Publication WO2004010957.

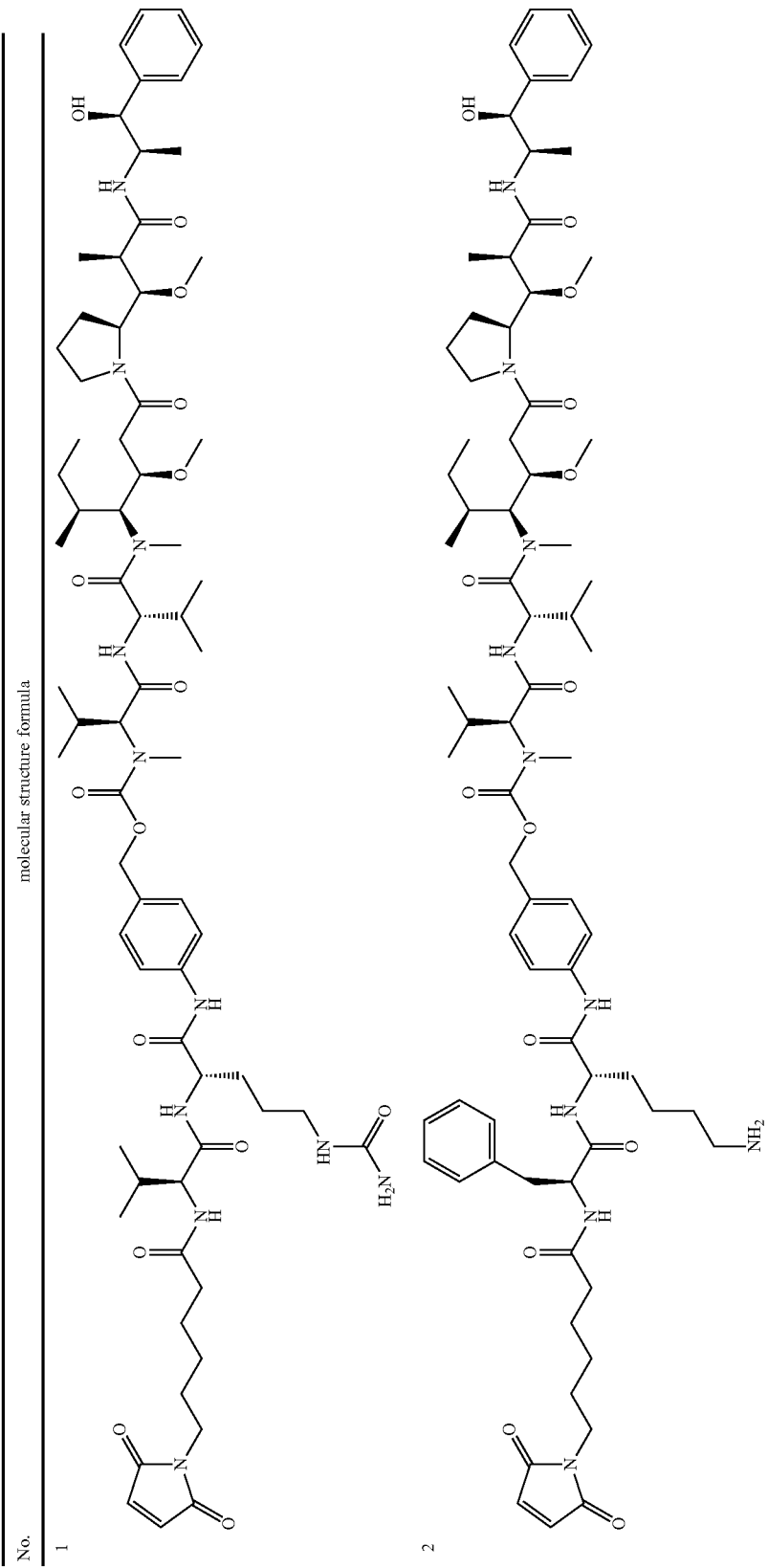

-continued
| No. | molecular structure formula |
|---|---|
| 3 | 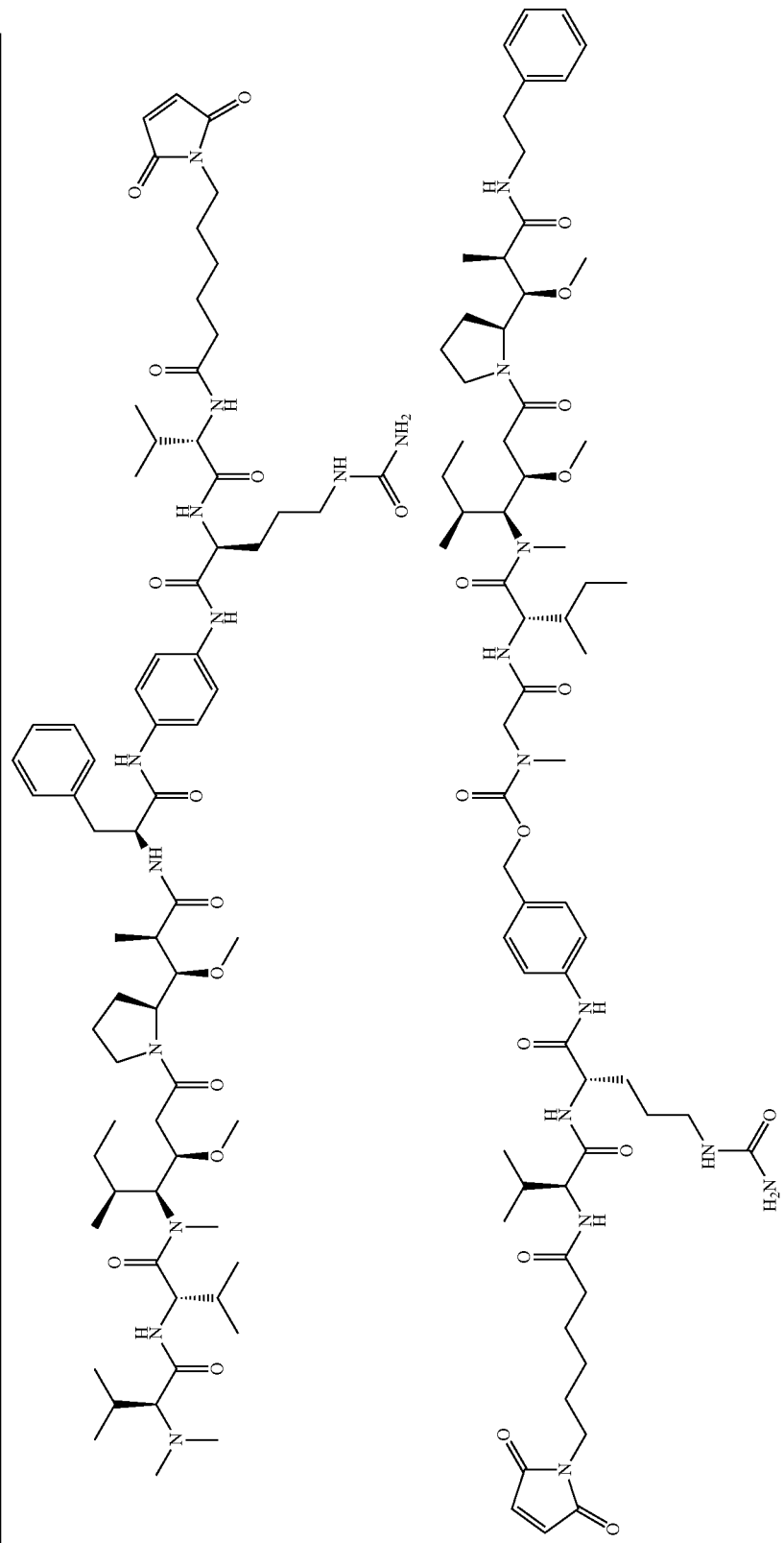 |
| 4 | |

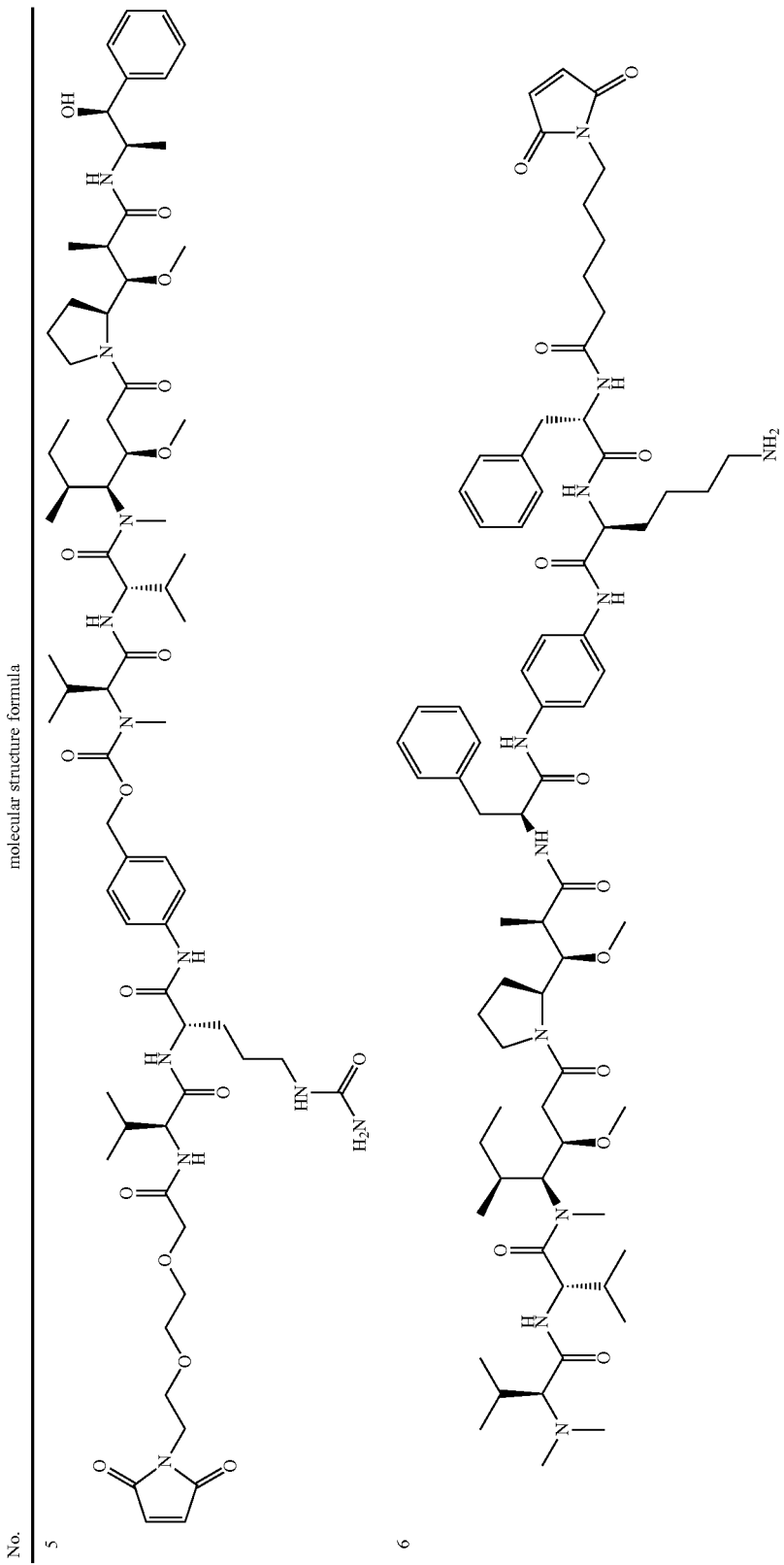

2. The following intermediate compounds 7-11 were prepared by a method disclosed in PCT Patent Application publication WO2005081711.

| No. | molecular structural formula |
|---|---|
| 7 | 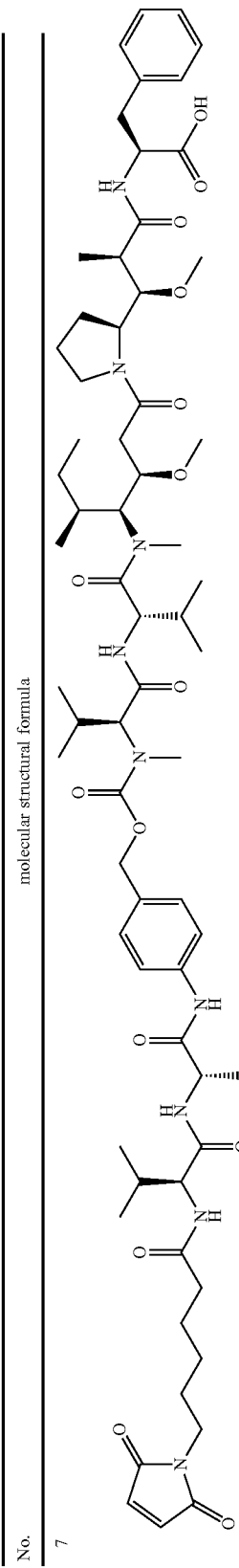 |
| 8 | 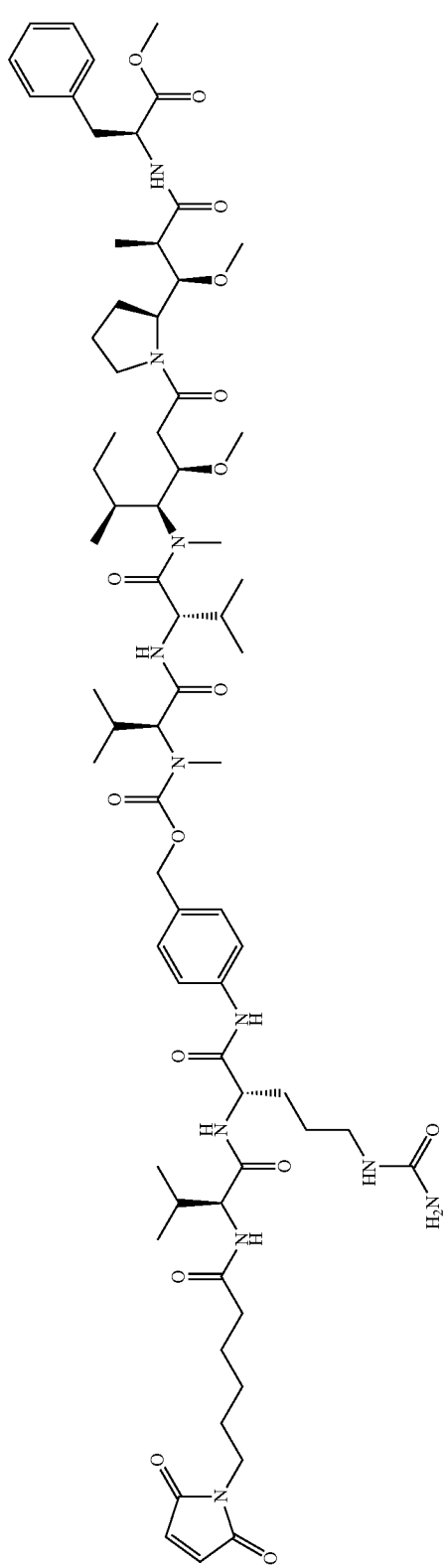 |

| No. | molecular structural formula |
|---|---|
| 9 | 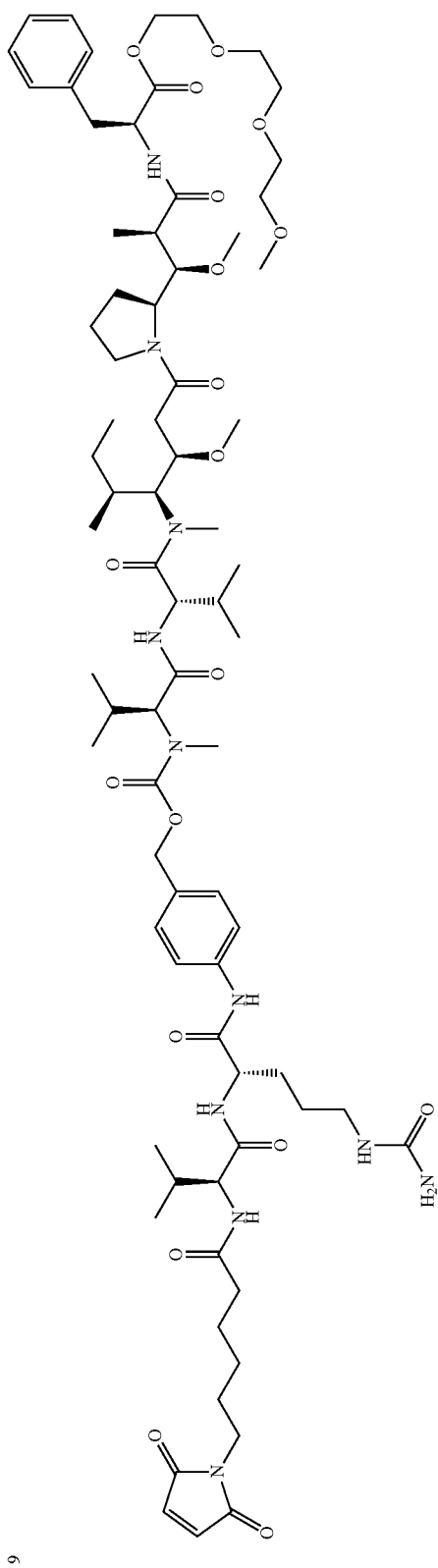 |
| 10 | 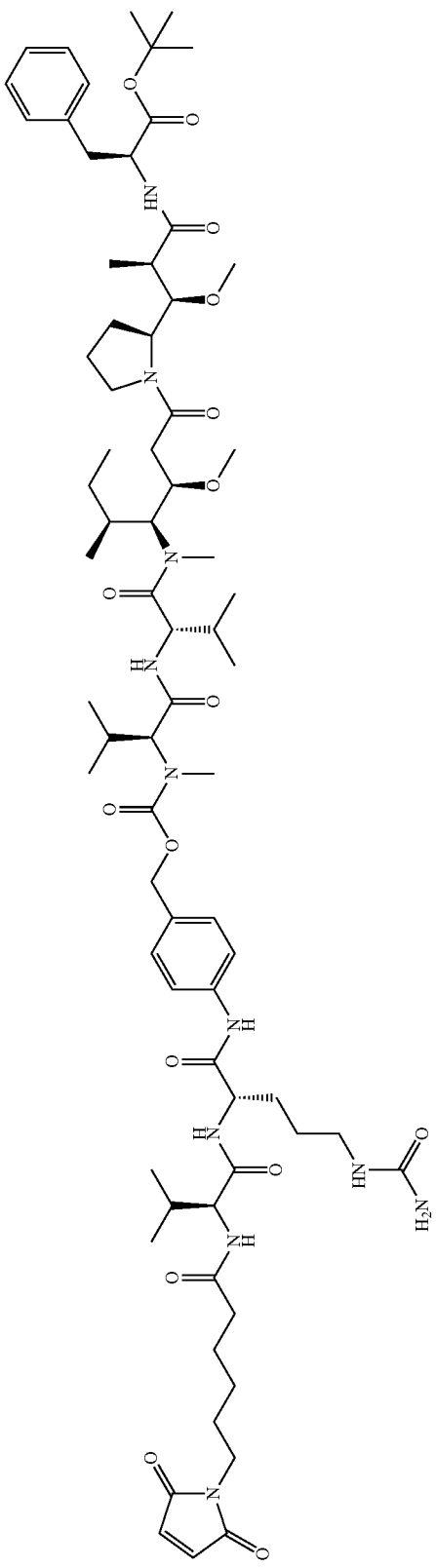 |

-continued
| No. | molecular structural formula |
|---|---|
| 11 | 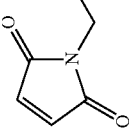 MC-MMAF |

3. The following intermediate compounds 12-14 were prepared by a method disclosed in U.S. Pat. No. 7,750,116.
| No | molecular structural formula |
|---|---|
| 12 | 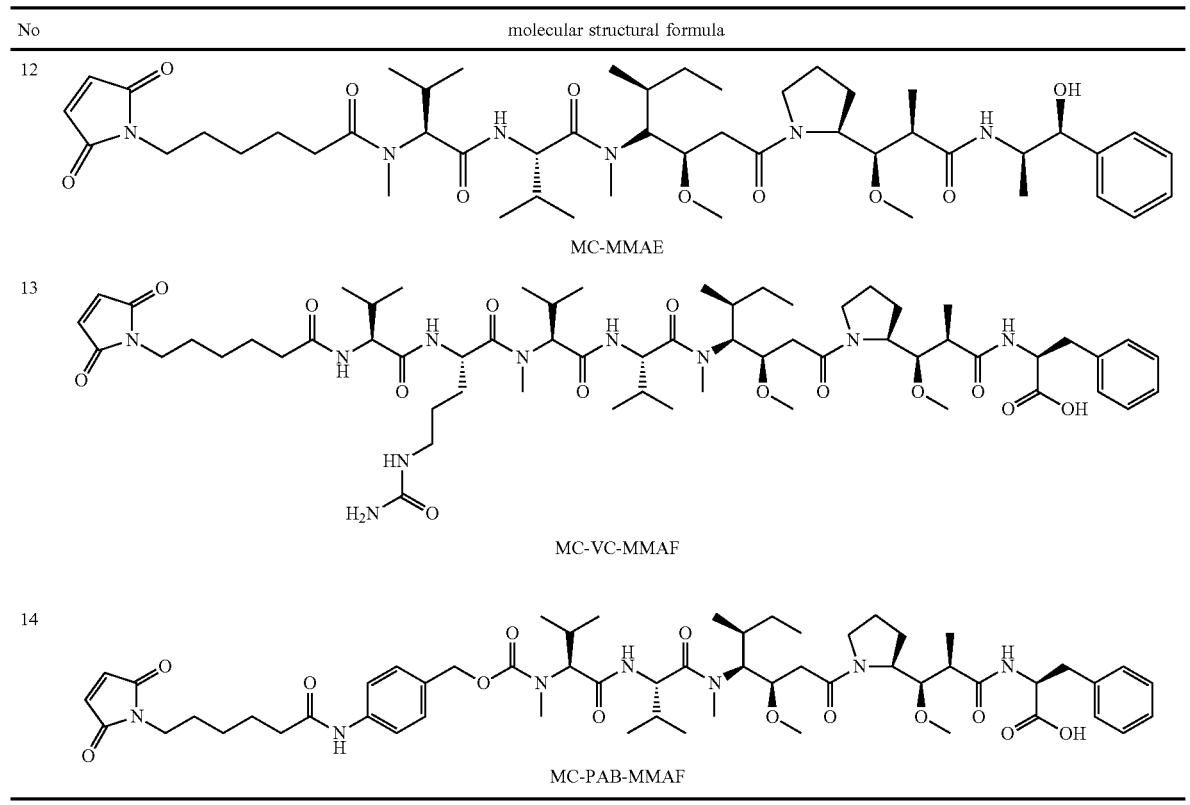 |
| 13 | |
| 14 | |
MC-MMAE
MC-VC-MMAF
MC-PAB-MMAF
4. Preparation of intermediate compound 15
15
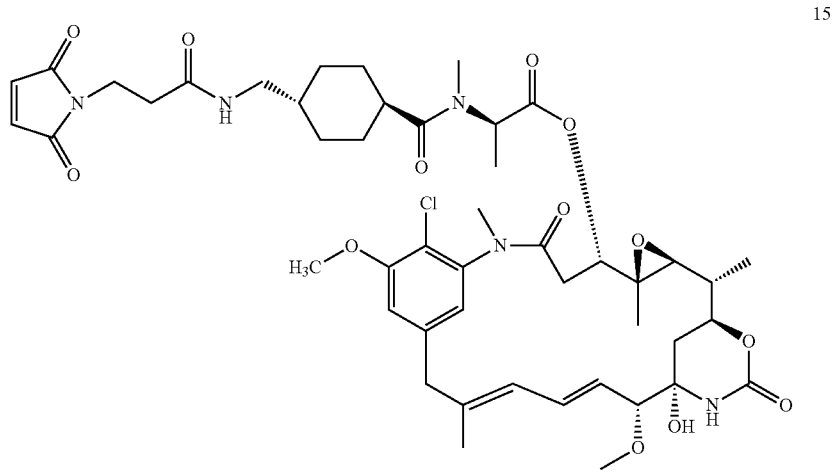 [SMILES: COc1cc2cc(c1Cl)N(C)C(=O)C[C@H](OC(=O)[C@@H](C)N(C)C(=O)[C@H]1CC[C@H](CNC(=O)CCN3C(=O)C=CC3=O)CC1)[C@]1(C)O[C@H]1[C@H](C)[C@@H]1C[C@@](O)(NC(=O)O1)[C@H](OC)/C=C/C=C(\C)C2]
Specific synthetic route was as follows:
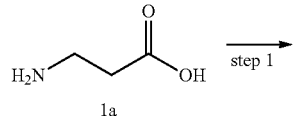
1a
-continued
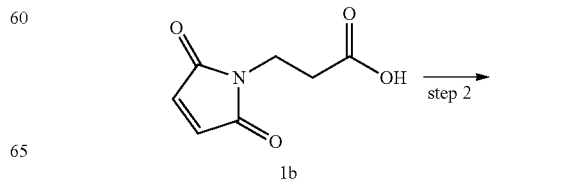
1b

63
-continued
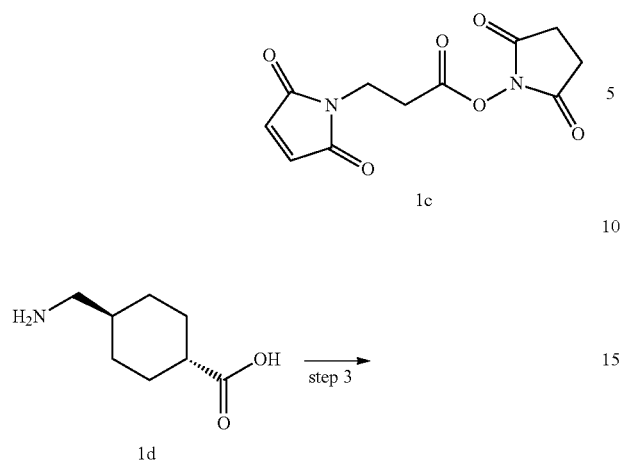
64
-continued
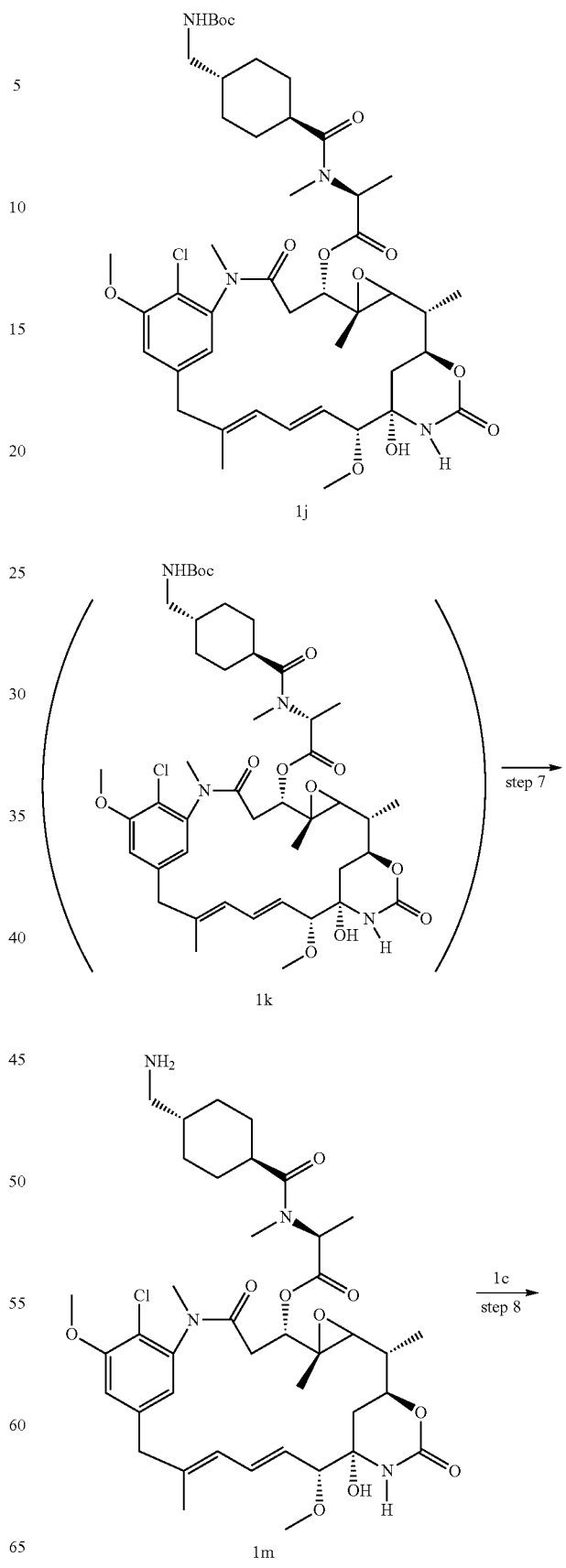

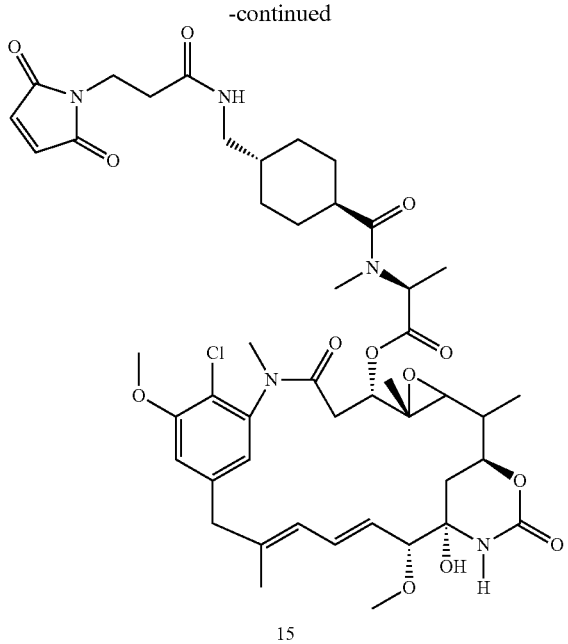

15

Step 1

3-(maleimide) propionic acid

The β-alanine 1a (2.29 g, 25.8 mmol) and maleic anhydride (2.52 g, 25.8 mmol) were dissolved in 20 mL of acetic acid, heated to reflux, and stirred for 2 hours. The reaction solution was concentrated under reduced pressure, the residue was treated with toluene for azeotropic distillation, dried with anhydrous sodium sulfate, and concentrated under reduced pressure. The residue was recrystallized with ethyl acetate, filtered and dried to obtain the entitled product 3-(maleimide) propionic acid 1b (2.80 g, yield 64.3%), as a colorless crystal.

MS m/z (ESI):170.04M+11.

Step 2

3-(maleimide) propionate succinimide ester 3-(maleimide) propionic acid 1b (2.80 g, 16.6 mmol) and N-hydroxysuccinimide (2.25 g, 19.9 mmol) were dissolved in 30 mL of DMF in an ice bath and cooled to 0° C., stirred for 10 minutes with addition of N, N'-dicyclohexyl carbodiimide (6.85 g, 33.2 mmol), and then the reaction was warmed to room temperature and stirred overnight. After filtration, the filtrate was mixed with 80 mL of dichloromethane, washed with water (60 mL×3), 5% sodium bicarbonate aqueous solution (60 mL×3), and saturated saline solution (50 mL×3) respectively. The organic layer was dried with anhydrous sodium sulfate, filtered, and the filtrate was concentrated under reduced pressure to obtain 3-(maleimide) propionate succinimide ester 1c (2.76 g, yield 62.5%) as a white solid.

MS m/z (ESI):267.06 [M+1].

Step 3

(1R, 4R)-4-(t-butoxycarbonyl-aminomethyl) cyclohexyl methanoic acid (1R, 4R)-4-(aminomethyl) cyclohexyl methanoic acid 1d (4.72 g, 30.0 mmol) and sodium hydroxide (1.28 g, 32.0 mmol) were dissolved in a solvent mixture of 20 mL of water and 44 mL of tert-butanol, followed by addition of tert-butyl dicarbonate (6.99 g, 32.0 mmol), and the reaction was stirred for 18 hours at room temperature. The reaction solution was added with 100 mL of water, washed with n-hexane (100 mL×3), the aqueous layer was cooled to 4° C., the pH was adjusted to 3 with saturated citric acid aqueous solution, the acidified solution was extracted with ethyl acetate (50 mL×3), and the organic layers were pooled, dried with anhydrous sodium sulfate, filtered, and the filtrate was concentrated under reduced pressure to obtain (1R, 4R)-4-(t-butoxycarbonyl-aminomethyl) cyclohexyl methanoic acid 1e (7.33 g, yield 95%) as a colorless crystal.

MS m/z (ESI):258.17 [M+1].

Step 4

(1R, 4R)-4-((tert-butoxycarbonylamino) methyl) cyclohexyl methanoic acid succinimide ester (1R, 4R)-4-(t-butoxycarbonyl-aminomethyl) cyclohexyl methanoic acid 1e (7.33 g, 28.5 mmol) and N-hydroxysuccinimide (3.87 g, 34.2 mmol) were dissolved in 35 mL of DMF in an ice bath and cooled to 0° C., stirred for 10 minutes with addition of N, N-dicyclohexyl carbodiimide (11.76 g, 57.0 mmol), and then the reaction was warmed to room temperature and stirred overnight. After filtration, the filtrate was mixed with 90 mL of dichloromethane, washed with water (60 mL×3), 5% NaHCO₃ aqueous solution (60 mL×3), saturated saline solution (50 mL×3), respectively. The organic layer was dried with anhydrous sodium sulfate, filtered, and the filtrate was concentrated under reduced pressure to obtain (1R, 4R)-4-((tert-butoxycarbonyl amino methyl) cyclohexyl methanoic acid succinimide ester if (6.75 g, yield 66.8%) as an almost white solid.

MS m/z (ESI):355.18 [M+1].

Step 5

S-2-((1R, 4S)-4-((tert-butoxycarbonylamino) methyl)-N-methyl-N-cyclohexylformyl) propanoic acid (1R, 4R)-4-((tert-butoxycarbonylaminomethyl) cyclohexyl methanoic acid succinimide ester if (6.75 g, 19.0 mmol) and N-methyl-L-alanine 1g (1.96 g, 19.0 mmol) were dissolved in 90 mL of solvent mixture of ethylene glycol dimethyl ether/water with a volume ratio of 1:1, followed by addition of triethylamine (4.05 g, 40 mmol). The mixture was reacted for 6 hours at room temperature, concentrated under reduced pressure, and the residue was dissolved with 100 mL of ethyl acetate, washed with saturated saline solution (80 mL×3), and the organic layer was dried with anhydrous sodium sulfate, filtered, and the filtrate was concentrated under reduced pressure. The residue was purified by thin-layer chromatography with developing solvent dichloromethane/methanol (50:1) to obtain S-2-((1R, 4R)-4-((tert-butoxycarbonylamino) methyl)-N-methyl-N-cyclohexylformyl) propanoic acid 1h (4.78 g, yield 73.5%) as an almost white solid.

MS m/z (ESI):343.22 [M+1].

Step 6

Maytansinol 1i (565.5 mg, 1.0 mmol, prepared by a well-known synthetic method published by Wayne C W, Sharon D W, Emily E C, et al., *J. Med. Chem*, 2006, 49, 4392-4408) and S-2-((1R, 4S)-4-((tert-butoxycarbonylamino)methyl)-N-methyl-N-cyclohexylformyl) propanoic acid 1h (2.05 g, 6.0 mmol) were dissolved in 20 mL of dichloromethane. N, N'-dicyclohexyl carbodiimide (1.30 g, 6.3 mmol) was dissolved in 5 mL of dichloromethane and added into the above reaction solution, then the mixture was dropwise slowly titrated with 1M zinc chloride in diethyl ether solution (1.2 mL, 1.2 mmol), and stirred at room temperature for 2 hours. After that the reaction solution was dissolved in 30 mL of ethyl acetate, filtered, and the filtrate was washed with saturated sodium bicarbonate (15 mL×2) and saturated saline solution (10 mL×2) respectively, and the organic layer was dried with anhydrous sodium sulfate, filtered, and the filtrate was concentrated under reduced pressure. The residue was purified by thin layer chromatography with developing solvent dichloromethane/methanol (50:1) to obtain the compound 1j (201.8 mg, yield 22.7%) as an almost white solid.

MS m/z (ESI):889.43 [M+1].

Step 7

Compound 1j (88.9 mg, 0.1 mmol) was dissolved in 8 mL of dichloromethane, followed by addition of trifluoroacetic acid (12.6 mg, 0.11 mmol). The reaction mixture was stirred at room temperature for 1 hour, concentrated under reduced pressure, and the residue was dissolved in 20 mL of ethyl acetate, washed with 5% sodium carbonate aqueous solution (6 mL×3), and the organic layer was dried with anhydrous sodium sulfate, filtered, and the filtrate was concentrated under reduced pressure to obtain the compound 1m (76.8 mg, yield 97.3%) as an almost white solid.

MS m/z (ESI): 789.38 [M+1].

Step 8

Compound 1m (76.8 mg, 0.097 mmol) and 3-(maleimide) propionate succinimide ester 1c (29.3 mg, 0.11 mmol) were dissolved in 10.0 ml of N, N'-dimethyl formamide, followed by addition of triethylamine (30.6 mg, 0.3 mmol). The mixture was reacted at room temperature for 8 hours, concentrated under reduced pressure, and the residue was dissolved with 20 mL of ethyl acetate, washed with saturated saline solution (10 mL×3), the organic layer was dried with anhydrous sodium sulfate, filtered, and the filtrate was concentrated under reduced pressure. The residue was purified by thin layer chromatography with developing solvent dichloromethane/methanol (40:1) to obtain the compound 15 (40.6 mg, yield 44.5%) as an almost white solid.

MS m/z (ESI):940.41 [M+1].

Preparation of Intermediates as Antibodies

The following antibodies were prepared according to conventional methods: for instance, vector construction, HEK293 cell transfection (Life Technologies Cat. No. 11625019), purification and expression.

1. Antibody sequences (1) Trastuzumab, capable of specifically binding to target HER2:

```
Sequence of light chain:
                                          (SEQ ID NO: 1)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

```
Sequence of heavy chain:
                                          (SEQ ID NO: 2)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

(2) Inotuzumab, capable of specifically binding to target CD22:

```
Sequence of light chain:
                                          (SEQ ID NO: 3)
DVQVTQSPSSLSASVGDRVTITCRSSQSLANSYGNTFLSWYLHKPGKAPQ

LLIYGISNRFSGVPDRFSGSGSGTDFTLTISSLQPEDFATYYCLQGTHQP

YTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

```
Sequence of heavy chain:
                                          (SEQ ID NO: 4)
EVQLVQSGAEVKKPGASVKVSCKASGYRFTNYWIHWVRQAPGQGLEWIGG

INPGNNYATYRRKFQGRVTMTADTSTSTVYMELSSLRSEDTAVYYCTREG

YGNYGAWFAYWGQGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
```

(3) Brentuximab, capable of specifically binding to target CD30:

```
Sequence of light chain:
                                          (SEQ ID NO: 5)
DIVLTQSPASLAVSLGQRATISCKASQSVDFDGDSYMNWYQQKPGQPPKV

LIYAASNLESGIPARFSGSGSGTDFTLNIHPVEEEDAATYYCQQSNEDPW

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC
```

-continued

Sequence of heavy chain:
(SEQ ID NO: 6)
QIQLQQSGPEVVKPGASVKISCKASGYTFTDYYITWVKQKPGQGLEWIGW
IYPGSGNTKYNEKFKGKATLTVDTSSSTAFMQLSSLTSEDTAVYFCANYG
NYWFAYWGQGTQVTVSAASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGSLSL
SPGK (4) Pertuzumab, capable of specifically binding to target HER2:

Sequence of light chain CDR-L1:
(SEQ ID NO: 7)
KASQDVSIGVA

Sequence of light chain CDR-L2:
(SEQ ID NO: 8)
SASYRYT

Sequence of light chain CDR-L3:
(SEQ ID NO: 9)
QQYYIYPYT

Sequence of heavy chain CDR-H1:
(SEQ ID NO: 10)
DYTMD

Sequence of heavy chain CDR-H2:
(SEQ ID NO: 11)
DVNPNSGGSIYNQRFKG

Sequence of heavy chain CDR-H3:
(SEQ ID NO: 12)
NLGPSFYFDY

Sequence of light chain:
(SEQ ID NO: 13)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Sequence of heavy chain:
(SEQ ID NO: 14)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK Example 2

Preparation of Antibody Drug Conjugate Compound 16

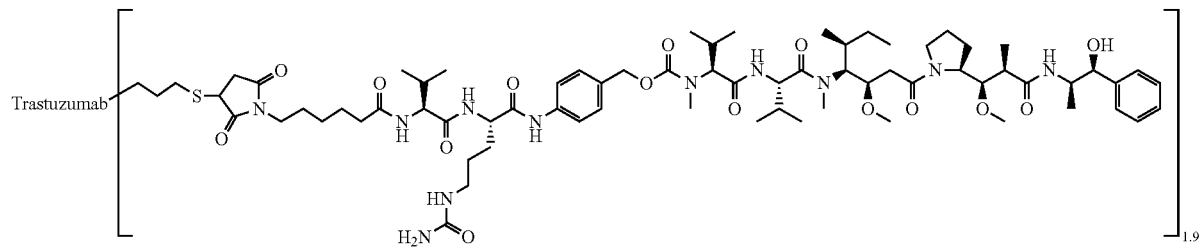

The synthetic route is as follows:

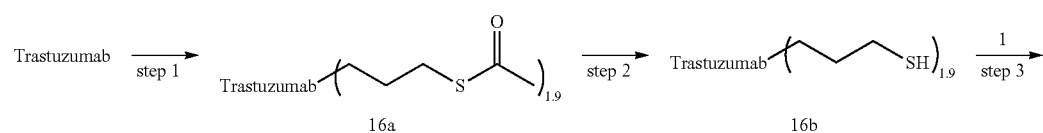

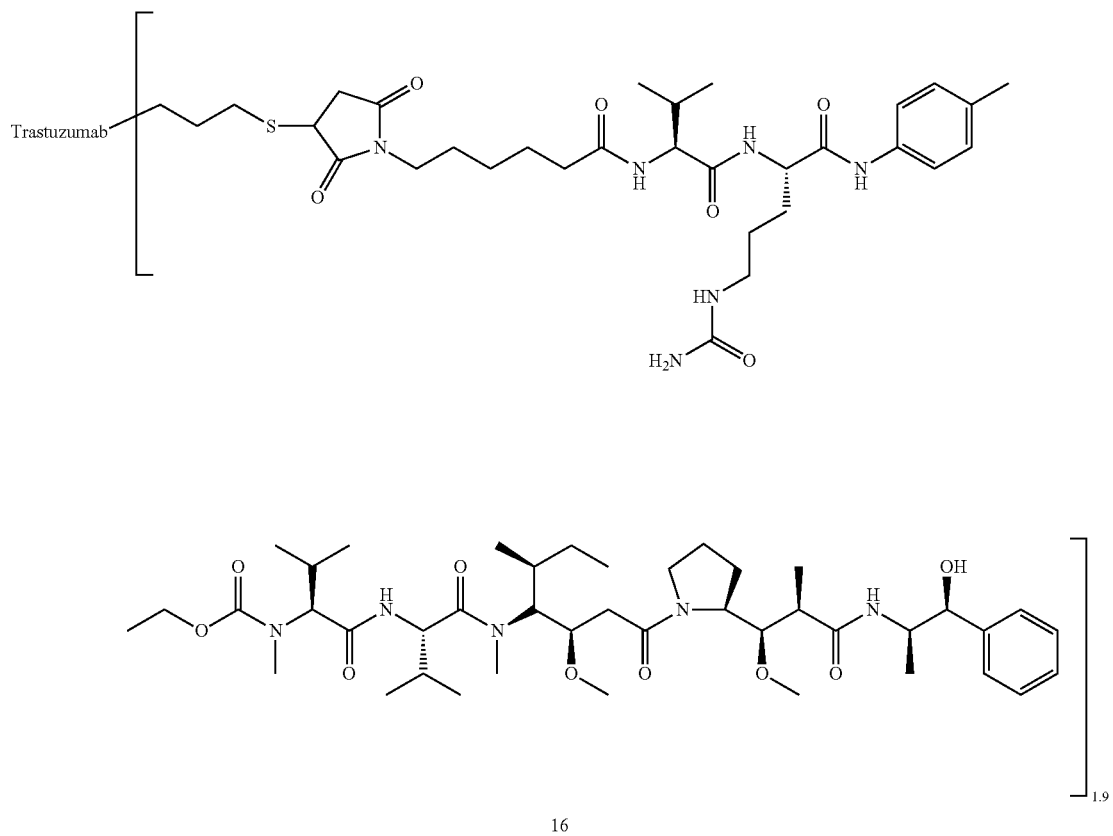

16

Step 1

Trastuzumab-propanethiol ethyl ester 32.0 mL (1.49 μmol) of trastuzumab stock solution (6.9 mg/ml, pH=6.3 in PBS solution) was replaced with an equal volume of 0.1 M acetic acid/sodium acetate buffer with pH 5.0. 3-acetyl-mercapto-propionaldehyde (0.79 mg, 5.98 μmol) was dissolved in 3.0 mL of acetonitrile and then dropwise titrated into the above solution buffer, dropwise added with sodium cyanoborohydride (0.92 mg, 14.6 μmol) dissolved in 1.0 mL water, and stirred for 3 hours at 25° C. After the reaction stopped, desalting and purification was performed by Sephadex G25 gel column (eluting phase: 0.05 M PBS solution containing 2 mM EDTA, pH 6.2) to obtain 45.1 mL of trastuzumab-propanethiol ethyl ester (16a) solution at a concentration of 4.8 mg/mL.

Step 2

Trastuzumab-propanethiol

Trastuzumab-propanethiol ethyl ester (16a) solution (prepared in step 1) was mixed with 73 μL of 2 M hydroxylamine hydrochloride, stirred at 25° C. for 1 hour, and then desalting and purification were performed by Sephadex G25 gel column (eluting phase: 0.05 M PBS solution containing 2 mM EDTA, pH 6.2) to obtain 71.3 mL of trastuzumab-propanethiol (16b) solution at a concentration of 3.0 mg/mL.

Step 3

Trastuzumab-propyl-1-sulfur-MC-Val-Cit-PAB-MMAE (compound 16)

Compound 1 (MC-Val-Cit-PAB-MMAE, 19.1 mg, 14.5 μmol) was dissolved in 7 mL of acetonitrile, followed by addition of trastuzumab-propanethiol (16b) solution (prepared in step 2). The reaction solution was stirred at 25° C. for 4 hours, the reaction was desalted and purified by Sephadex G25 gel column (eluting phase: 0.05 M of PBS solution containing 2 mM EDTA, pH 6.2) and filtrated under a sterile condition through a 0.2 μm filter to obtain 101.0 mL of Trastuzumab-propyl-1-sulfur-MC-Val-Cit-PAB-MMAE (16) solution at a concentration of 2.03 mg/mL. The solution was filtrated under a sterile condition through a 0.2 μm filter and stored at −20° C. frozen storage.

Q-TOF LC/MS: 148381.5 ($M_{Ab}$+OD), 149613.2 ($M_{Ab}$+1D), 151169.8 ($M_{Ab}$+2D), 152587.7 ($M_{Ab}$+3D), 153868.1 ($M_{Ab}$+4D), 155484.4 ($M_{Ab}$+5D).

n=1.9.

Example 3

Preparation of Antibody Drug Conjugate Compound 22

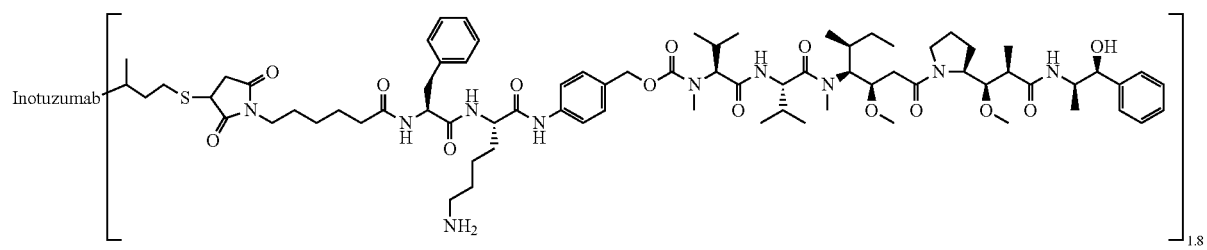

The synthetic route is as follows: (consistent with those described above)

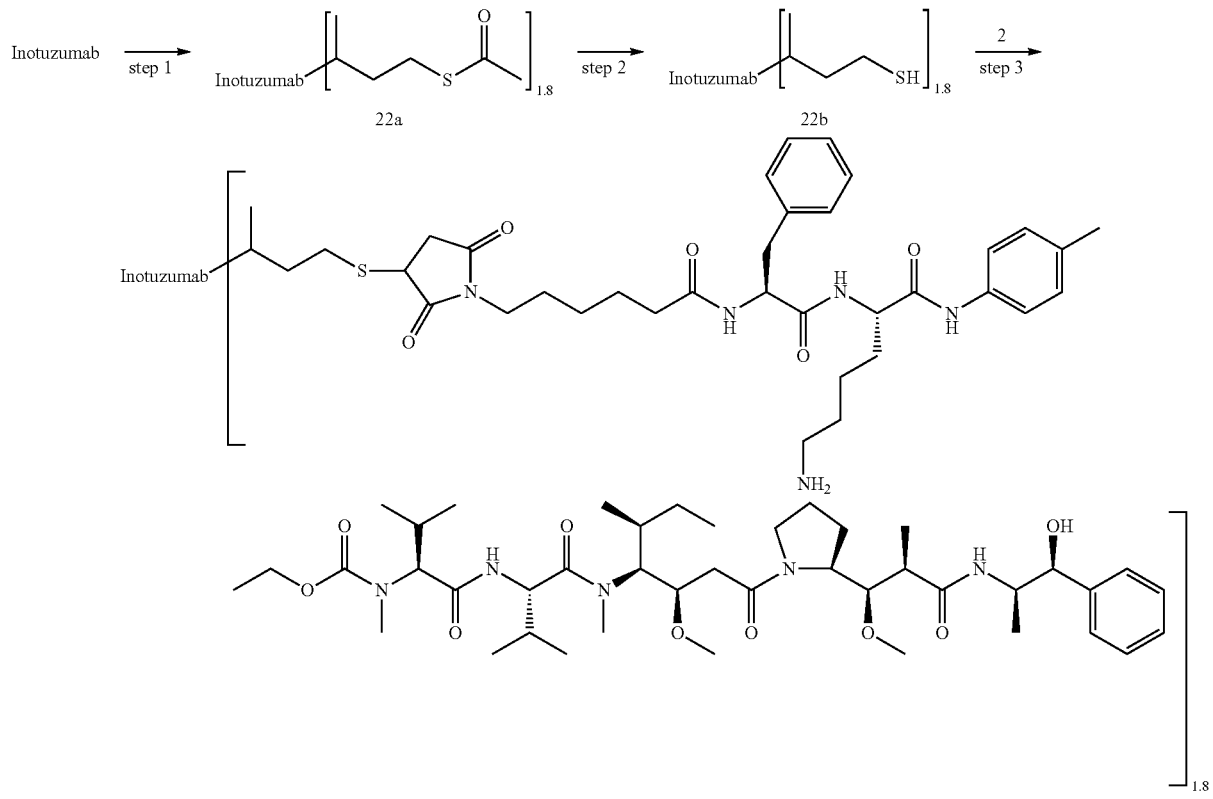

Step 1

Inotuzumab-1-methyl propanethiol ethyl ester

S-(3-oxobutyl) thio-ethyl acetate (0.70 mg, 4.32 μmol) was dissolved in 3.0 mL of acetonitrile, then dropwise titrated into 20.0 mL (1.08 μmol) of Inotuzumab stock solution (8.1 mg/mL, pH=6.0 in PBS solution). Trimethoxy sodium borohydride (2.29 mg, 10.8 μmol) was dissolved in 2.0 mL of water and dropwise titrated into the above reaction solution, and stirred for 48 hours at 30° C. After that, the reaction solution was desalted and purified by Sephadex G25 gel column (eluting phase: 0.05 M PBS solution containing 2 mM EDTA, pH 6.2) to obtain 29.2 mL of Inotuzumab-1-methyl propanethiol ethyl ester (22a) solution at a concentration of 5.4 mg/mL.

Compound 22 was prepared according to the procedure of steps 2 and 3 in Example 2, and in addition, compound 2 was used in step 3.

Q-TOF LC/MS: 149611.1 ($M_{Ab}$+0D), 151039.9 ($M_{Ab}$+1D), 152470.6 ($M_{Ab}$+2D), 153904.4 ($M_{Ab}$+3D), 155317.0 ($M_{Ab}$+4D), 156757.9 ($M_{Ab}$+5D).

n=1.8.

Referring to the preparation procedures of the antibody drug conjugate 16 described in Example 2 as a reference, the antibody drug conjugates 17-21, 24-27, 29, and 30 were prepared by using the corresponding antibodies (Trastuzumab, Inotuzumab, Brentuximab) and cytotoxic drugs.

| antibody drug conjugate | Interval Unit-cytotoxic drug | Q-TOF LC/MS |
|---|---|---|
| 16 | Compound 1 | 148381.5($M_{Ab}$ + 0D), 149613.2($M_{Ab}$ + 1D), 151169.8($M_{Ab}$ + 2D), 152587.7($M_{Ab}$ + 3D), 153868.1($M_{Ab}$ + 4D), 155484.4($M_{Ab}$ + 5D) |
| 17 | Compound 12 | 148220.4($M_{Ab}$ + 0D), 149212.0($M_{Ab}$ + 1D), 150212.8($M_{Ab}$ + 2D), 151272.8($M_{Ab}$ + 3D), 152205.0($M_{Ab}$ + 4D), 153236.5($M_{Ab}$ + 5D) |
| 18 | Compound 11 | 148223.9($M_{Ab}$ + 0D), 149227.6($M_{Ab}$ + 1D), 150264.5($M_{Ab}$ + 2D), 151302.8($M_{Ab}$ + 3D), 152363.8($M_{Ab}$ + 4D), 153412.8($M_{Ab}$ + 5D) |

-continued

| antibody drug conjugate | Interval Unit-cytotoxic drug | Q-TOF LC/MS |
|---|---|---|
| [Structure 19: Trastuzumab-linker-drug conjugate, subscript 2.2] | Compound 7 | 148229.9($M_{Ab}$ + 0D), 149639.7($M_{Ab}$ + 1D), 151050.5($M_{Ab}$ + 2D), 152449.3($M_{Ab}$ + 3D), 153900.1($M_{Ab}$ + 4D), 155317.2($M_{Ab}$ + 5D). |
| [Structure 20: Trastuzumab-linker-maytansinoid conjugate, subscript 2.0] | Compound 15 | 148233.1($M_{Ab}$ + 0D), 149248.5($M_{Ab}$ + 1D), 150271.9($M_{Ab}$ + 2D), 151286.2($M_{Ab}$ + 3D), 152294.1($M_{Ab}$ + 4D), 153294.3($M_{Ab}$ + 5D) |

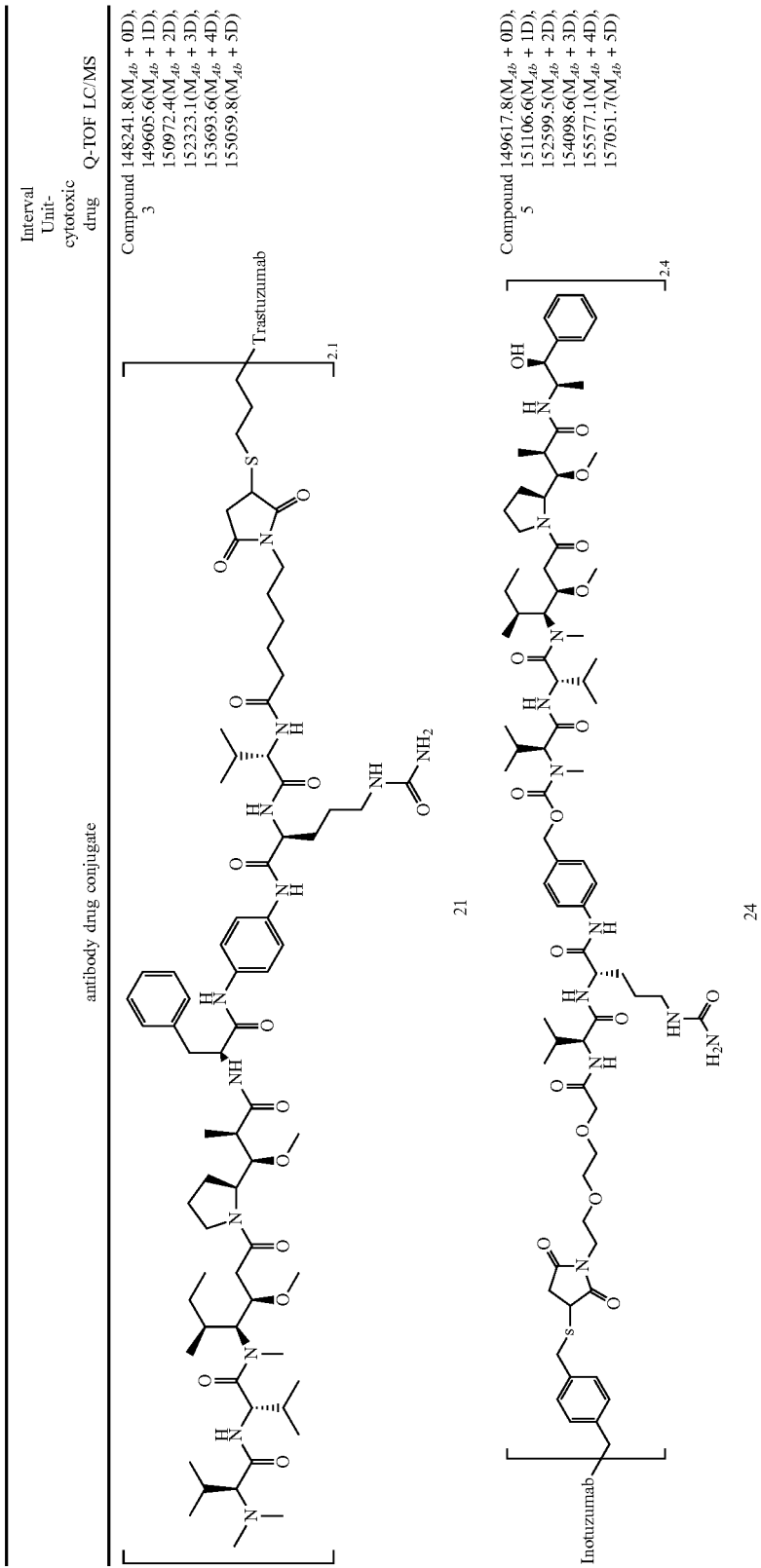

-continued

| antibody drug conjugate | Interval Unit-cytotoxic drug | Q-TOF LC/MS |
|---|---|---|
| 25 | Compound 8 | 149623.1(M$_{Ab}$ + 0D), 151056.9(M$_{Ab}$ + 1D), 152479.8(M$_{Ab}$ + 2D), 153901.1(M$_{Ab}$ + 3D), 155343.2(M$_{Ab}$ + 4D), 156787.4(M$_{Ab}$ + 5D) |
| 26 | Compound 6 | 148268.0(M$_{Ab}$ + 0D), 149718.1(M$_{Ab}$ + 1D), 151151.3(M$_{Ab}$ + 2D), 152595.5(M$_{Ab}$ + 3D), 154042.4(M$_{Ab}$ + 4D), 155501.0(M$_{Ab}$ + 5D) |

| antibody drug conjugate | Interval Unit-cytotoxic drug | Q-TOF LC/MS |
|---|---|---|
| 27 (Brentuximab conjugate, ratio 2.0) | Compound 9 | 148240.7(M$_{Ab}$ + 0D), 149771.5(M$_{Ab}$ + 1D), 151316.2(M$_{Ab}$ + 2D), 152852.4(M$_{Ab}$ + 3D), 154403.2(M$_{Ab}$ + 4D), 155964.3(M$_{Ab}$ + 5D) |
| 29 (Trastuzumab conjugate, ratio 2.1) | Compound 13 | 148230.2(M$_{Ab}$ + 0D), 149485.9(M$_{Ab}$ + 1D), 150754.2(M$_{Ab}$ + 2D), 152009.5(M$_{Ab}$ + 3D), 153276.2(M$_{Ab}$ + 4D), 154536.9(M$_{Ab}$ + 5D) |
| 30 (Trastuzumab conjugate, ratio 1.9) | Compound 14 | 148210.1(M$_{Ab}$ + 0D), 149360.3(M$_{Ab}$ + 1D), 150515.5(M$_{Ab}$ + 2D), 151677.0(M$_{Ab}$ + 3D), 152821.9(M$_{Ab}$ + 4D), 153980.7(M$_{Ab}$ + 5D) |

Referring to the preparation procedures of antibody drug conjugate 22 described in Example 3, the antibody drug conjugates 23 and 28 were prepared by using the corresponding antibodies (Inotuzumab, Brentuximab) and drugs.

| antibody drug conjugate | Interval Unit-cytotoxic drug | Q-TOF LC/MS |
|---|---|---|
| 22 | Compound 2 | 149611.1($M_{Ab}$ + 0D), 151039.9($M_{Ab}$ + 1D), 152470.6($M_{Ab}$ + 2D), 153904.4($M_{Ab}$ + 3D), 155317.0($M_{Ab}$ + 4D), 156757.9($M_{Ab}$ + 5D) |
| 23 | Compound 4 | 149607.2($M_{Ab}$ + 0D), 150971.0($M_{Ab}$ + 1D), 152340.4($M_{Ab}$ + 2D), 153712.0($M_{Ab}$ + 3D), 155067.2($M_{Ab}$ + 4D), 156414.5($M_{Ab}$ + 5D) |
| 28 | Compound 10 | 148255.2($M_{Ab}$ + 0D), 149786.1($M_{Ab}$ + 1D), 151315.0($M_{Ab}$ + 2D), 152870.4($M_{Ab}$ + 3D), 154431.3($M_{Ab}$ + 4D), 155954.1($M_{Ab}$ + 5D) |

The antibody drug conjugates 31, 32, 33 and 34 were prepared by using the antibody pertuzumab and the corresponding drugs according to Example 4, Example 5, Example 6, and Example 7.

| antibody drug conjugate | Interval-Unit-cytotoxic drug | Q-TOF LC/MS |
|---|---|---|
| 31 | Compound 12 | 148096.2($M_{Ab}$ + 0D), 149096.1($M_{Ab}$ + 1D), 150095.7($M_{Ab}$ + 2D), 151096.5($M_{Ab}$ + 3D), 152097.0($M_{Ab}$ + 4D), 153097.1($M_{Ab}$ + 5D) |
| 32 | Compound 11 | 148094.6($M_{Ab}$ + 0D), 149081.2($M_{Ab}$ + 1D), 150066.9($M_{Ab}$ + 2D), 151053.3($M_{Ab}$ + 3D), 152040.0($M_{Ab}$ + 4D), 153025.7($M_{Ab}$ + 5D) |
| 33 | Compound 7 | 148094.8($M_{Ab}$ + 0D), 149501.3($M_{Ab}$ + 1D), 150908.5($M_{Ab}$ + 2D), 152315.0($M_{Ab}$ + 3D), 153721.4($M_{Ab}$ + 4D), 155128.1($M_{Ab}$ + 5D) |

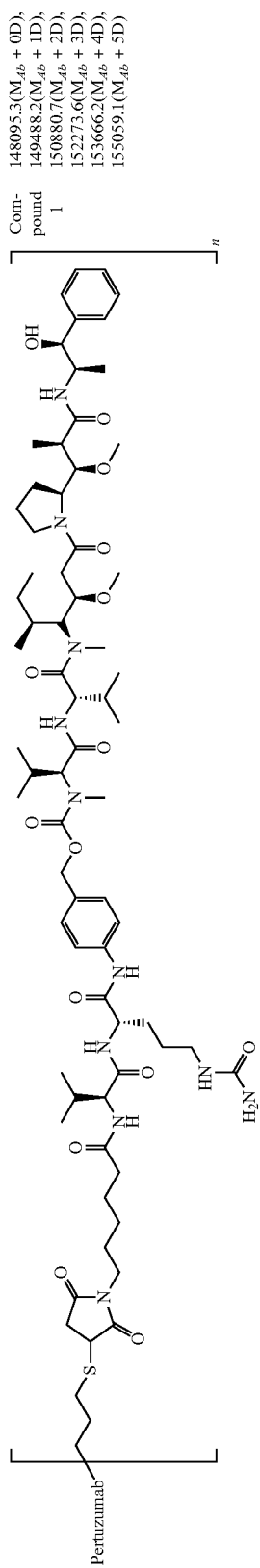
| antibody drug conjugate | Interval Unit-cytotoxic drug | Q-TOF LC/MS |
|---|---|---|
| 34 | Compound 1 | 148095.3($M_{Ab}$ + 0D), 149488.2($M_{Ab}$ + 1D), 150880.7($M_{Ab}$ + 2D), 152273.6($M_{Ab}$ + 3D), 153666.2($M_{Ab}$ + 4D), 155059.1($M_{Ab}$ + 5D) |

Example 4

Preparation of Antibody Drug Conjugate
Compound 31

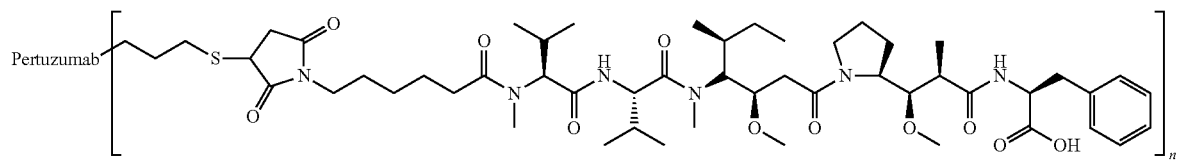

The synthetic route is as follows:

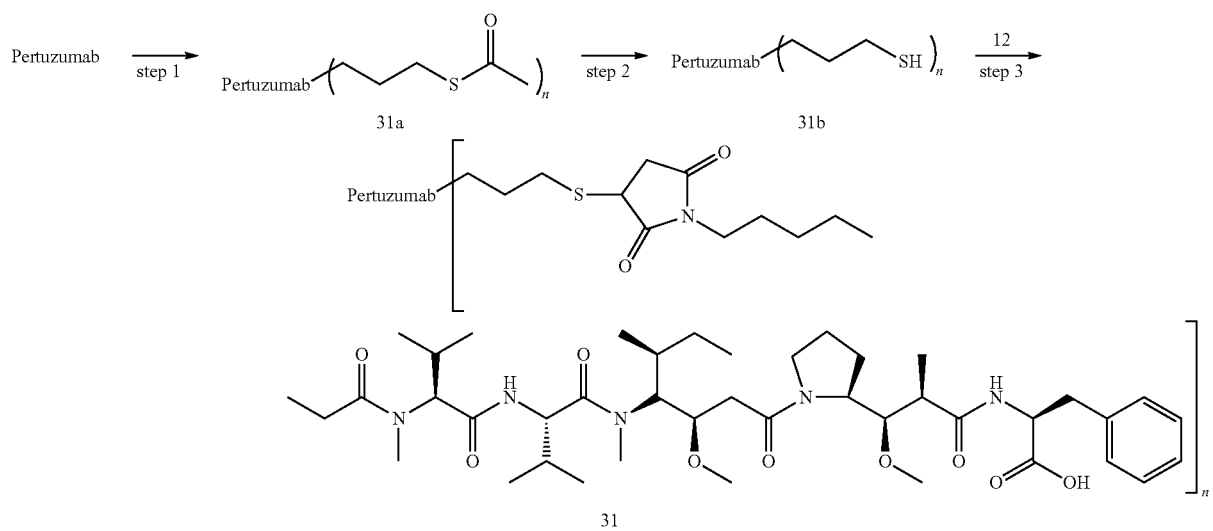

Step 1

Pertuzumab-propanethiol ethyl ester

Pertuzumab stock solution (preserved in buffer system with 20 mM L-histidine acetate, 120 mM sucrose, pH=5.7) was exchanged to 100 mM acetic acid-sodium acetate buffer (pH=4.3-4.5) by using G-25 size exclusion column, and concentrated to a concentration of about 10.0 mg/mL to obtain 200 mL of P-mAb acetic acid-sodium acetate buffer (13.5 mmol). 3-acetyl-mercapto-propionaldehyde (14.3 mg, 0.108 mmol) was dissolved in 20 mL of acetonitrile and then dropwise titrated into the above buffer. Then, sodium cyanoborohydride (173 mg, 2.7 mmol) was dissolved in 10 mL of water and dropwise titrated into the above reaction solution, and stirred at 25° C. for 3 hours. After that, the reaction solution was desalted and purified by Sephadex G25 gel column (eluting phase: 0.05 M PBS solution containing 2 mM EDTA, pH 6.3) to obtain 300 mL of pertuzumab-propanethiol ethyl ester (31a) solution at a concentration of 6.5 mg/mL.

Step 2

Pertuzumab-propanethiol 6.0 mL of 2M hydroxylamine hydrochloride was added into Pertuzumab-propanethiol ethyl ester (31a) solution (prepared in step 1), and stirred at 25° C. for 1 hour. Then, the reaction solution was desalted and purified by Sephadex G25 gel column (eluting phase: 0.05 M PBS solution containing 2 mM EDTA, pH 6.3) to obtain 450 mL of pertuzumab-propanethiol (31b) solution at a concentration of 4.3 mg/mL.

Step 3

Pertuzumab-propyl-1-sulfur-MC-MMAF

Compound 12 (MC-MMAF, 125 mg, 13.5 mmol) was dissolved in 45 mL of acetonitrile and added into pertuzumab-propanethiol (31b) solution (prepared in step 2). After stirring at 25° C. for 4 hours, the reaction solution was desalted and purified by Sephadex G25 gel column (eluting phase: 0.05 M PBS solution containing 2 mM EDTA, pH 6.3), and concentrated and filtrated under a sterile condition through a 0.2 μm filter to obtain 240 mL of pertuzumab-propyl-1-sulfur-MC-MMAF (compound 31) solution at a concentration of 8.02 mg/mL, and then stored at −20° C. frozen storage.

Example 5

Preparation of Antibody Drug Conjugate
Compound 32

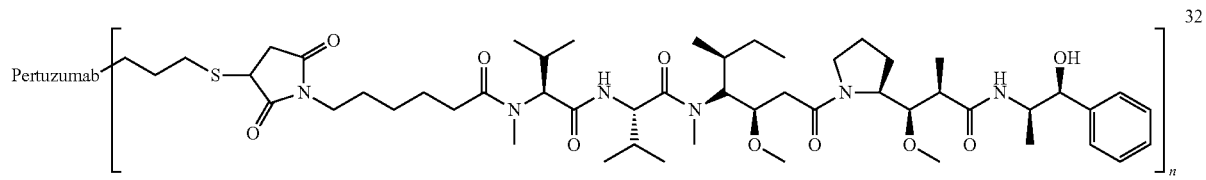

The synthetic route is as follows:

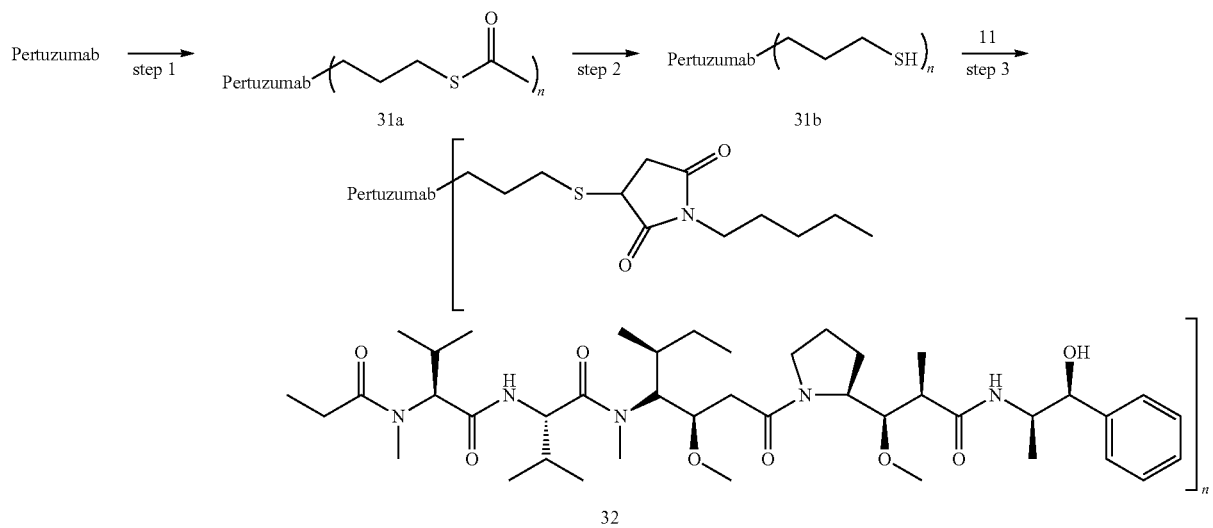

Step 1

Pertuzumab-propanethiol ethyl ester

Pertuzumab stock solution (preserved in buffer system with 20 mM L-histidine acetate, 120 mM sucrose, pH=5.7) was exchanged to 100 mM acetic acid-sodium acetate buffer (pH=4.3-4.5) with G-25 size exclusion column, and concentrated to a concentration of about 10.0 mg/mL to obtain 2.0 mL of P-mAb acetic acid-sodium acetate buffer (0.135 mmol). 3-acetyl-mercapto-propionaldehyde (0.15 mg, 1.1 μmol) was dissolved in 0.2 mL of acetonitrile and then dropwise titrated into the above solution buffer. Sodium cyanoborohydride (173 mg, 2.7 mmol) was dissolved in 0.2 mL of water and dropwise titrated into the above reaction solution, and stirred at 25° C. for 3 hours. After that, the reaction solution was desalted and purified by Sephadex G25 gel column (eluting phase: 0.05 M PBS solution containing 2 mM EDTA, pH 6.3) to obtain 3.0 mL of pertuzumab-propanethiol ethyl ester (31a) solution at a concentration of 6.5 mg/mL.

Step 2

Pertuzumab-propanethiol 0.06 mL of 2 M hydroxylamine hydrochloride was added into Pertuzumab-propanethiol ethyl ester (31a) solution (prepared in step 1), and stirred at 25° C. for 1 hour. Then, the reaction solution was desalted and purified by Sephadex G25 gel column (eluting phase: 0.05 M PBS solution containing 2 mM EDTA, pH 6.3) to obtain 5.0 mL of pertuzumab-propanethiol (31b) solution at a concentration of 3.8 mg/mL.

Step 3

Pertuzumab-propyl-1-sulfur-MC-MMAE

Compound 11 (MC-MMAE, 1.3 mg, 1.4 μmol) was dissolved in 0.55 ml of acetonitrile and was added into pertuzumab-propanethiol (31b) solution (prepared in step 2). After stirring at 25° C. for 4 hours, the reaction solution was desalted and purified by Sephadex G25 gel column (eluting phase: 0.05 M PBS solution containing 2 mM EDTA, pH 6.3), filtrated under a sterile condition through a 0.2 μm filter to obtain 8.0 mL of pertuzumab-propyl-1-sulfur-MC-MMAE (compound 32) solution at a concentration of 2.4 mg/mL, and then stored at −20° C. frozen storage.

Example 6
Preparation of Antibody Drug Conjugate
Compound 33
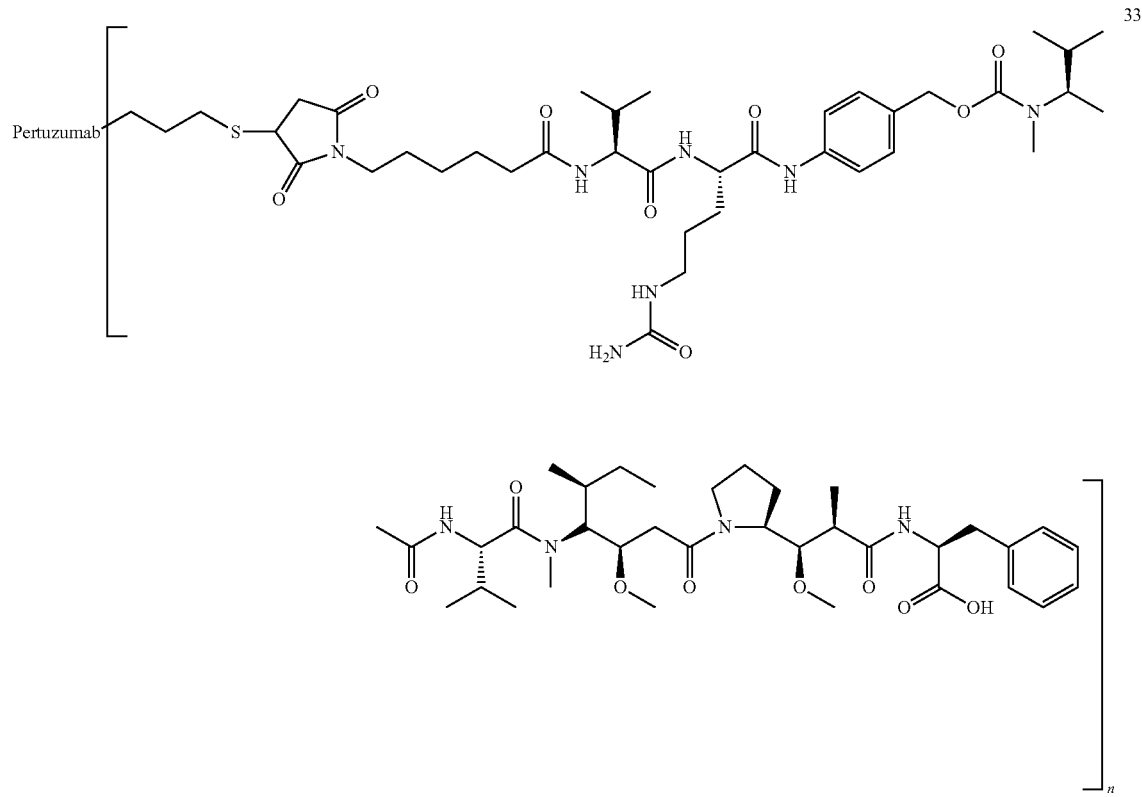
The synthetic route is as follows:
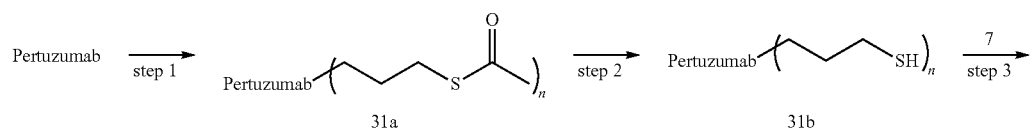
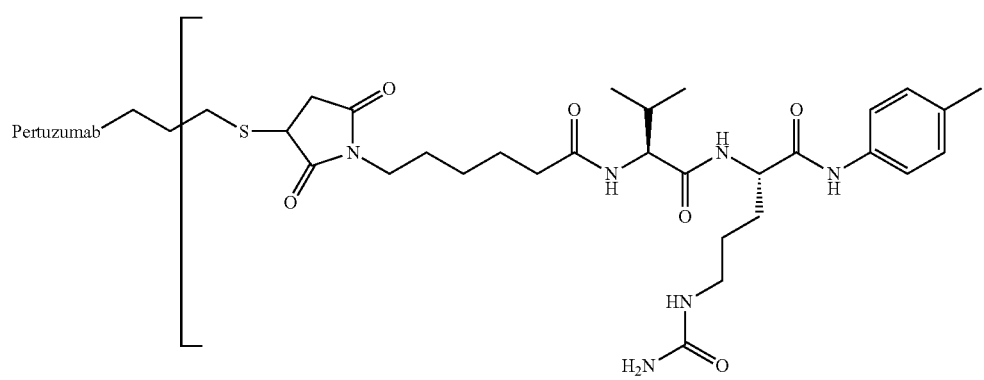

-continued

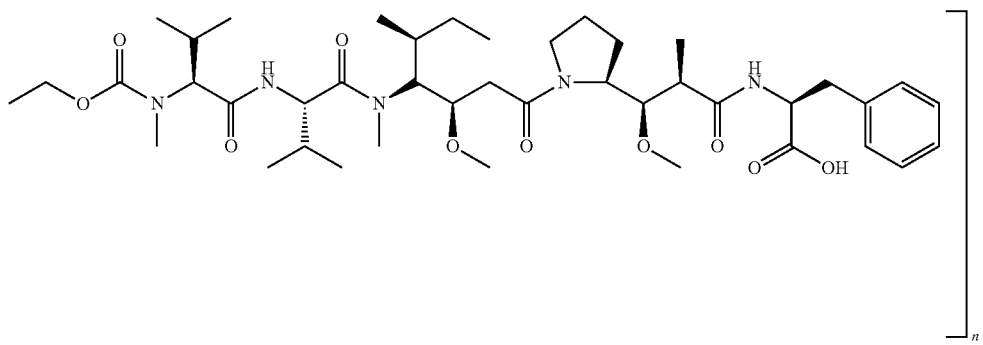

33

Step 1

Pertuzumab-propanethiol ethyl ester

Pertuzumab stock solution (preserved in buffer system with 20 mM L-histidine acetate, 120 mM sucrose, pH=5.7) was exchanged to 100 mM acetic acid-sodium acetate buffer (pH=4.3-4.5) with a G-25 size exclusion column, and concentrated to a concentration of about 10.0 mg/mL to obtain 200 mL of P-mAb acetic acid-sodium acetate buffer (13.5 mmol). 3-acetyl-mercapto-propionaldehyde (14.3 mg, 0.108 mmol) was dissolved in 20 mL of acetonitrile and then dropwise titrated into the above buffer. Sodium cyanoborohydride (173 mg, 2.7 mmol) was dissolved in 10 mL of water and dropwise titrated into the reaction solution, and stirred at 25° C. for 3 hours. After that, the reaction solution was desalted and purified by Sephadex G25 gel column (eluting phase: 0.05 M PBS solution containing 2 mM EDTA, pH 6.3) to obtain 300 mL of pertuzumab-propanethiol ethyl ester (31a) solution at a concentration of 6.5 mg/mL.

Step 2

Pertuzumab-propanethiol 6.0 mL of 2 M hydroxylamine hydrochloride was added into Pertuzumab-propanethiol ethyl ester (31a) solution (prepared in step 1), and stirred at 25° C. for 1 hour. Then, the reaction solution was desalted and purified by Sephadex G25 gel column (eluting phase: 0.05 M PBS solution containing 2 mM EDTA, pH 6.3) to obtain 450 mL of pertuzumab-propanethiol (31b) solution at the concentration of 4.3 mg/mL.

Step 3

Pertuzumab-propyl-1-sulfur-MC-VC-PAB-MMAF

Compound 7 (MC-VC-PAB-MMAF, 180 mg, 13.5 mmol) was dissolved in 45 mL of acetonitrile and added into pertuzumab-propanethiol (31b) solution (prepared in step 2). After stirring at 25° C. for 4 hours, the reaction solution was desalted and purified by Sephadex G25 gel column (eluting phase: 0.05 M PBS solution containing 2 mM EDTA, pH 6.3), concentrated and filtrated under a sterile condition through a 0.2 μm filter to obtain 240 mL of pertuzumab-propyl-1-sulfur-MC-VC-PAB-MMAF (compound 33) solution at a concentration of 8.0 mg/mL, and then stored at −20° C. frozen storage.

Example 7

Preparation of Antibody Drug Conjugate Compound 34

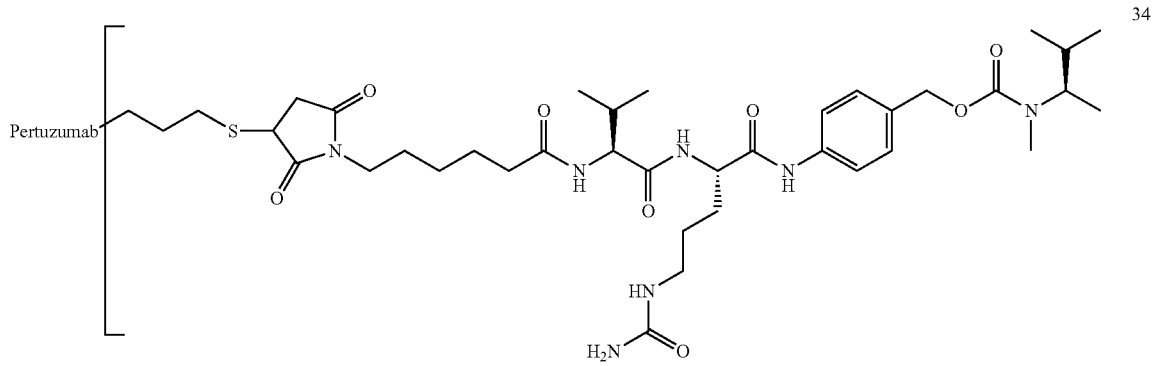

34

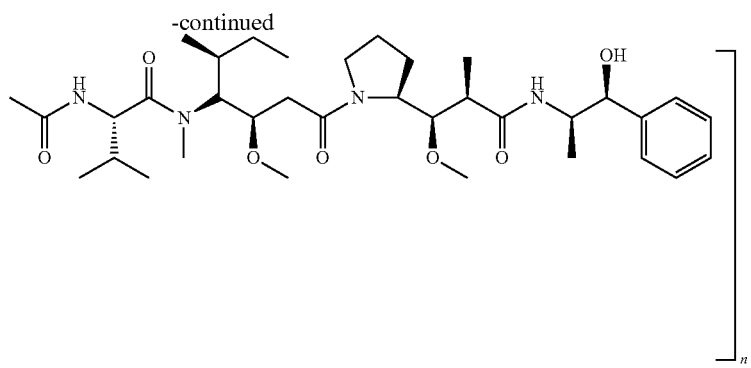

The synthetic route is as follows:

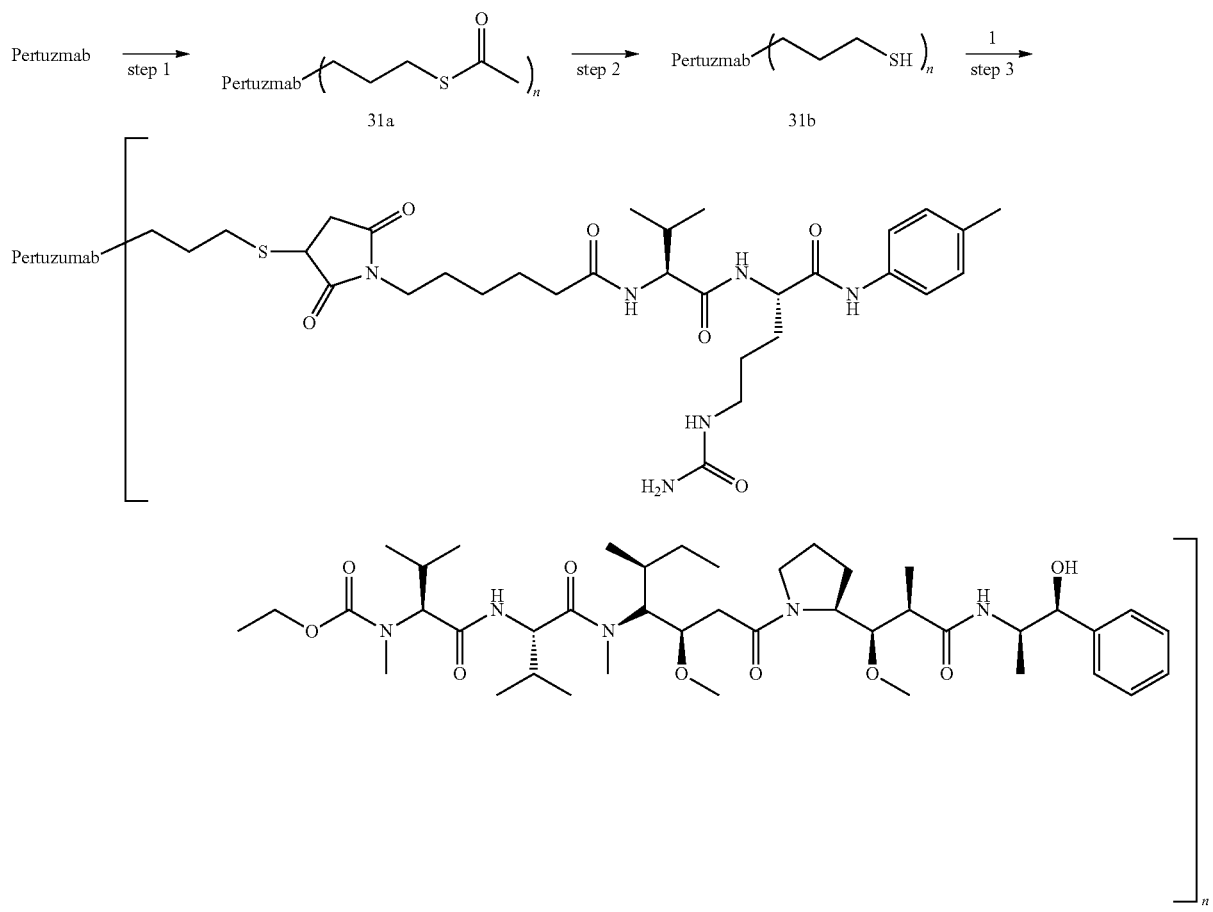

Step 1

Pertuzumab-propanethiol ethyl ester

Pertuzumab stock solution (preserved in buffer system with 20 mM L-histidine acetate, 120 mM sucrose, pH=5.7) was exchanged to 100 mM acetic acid-sodium acetate buffer (pH=4.3-4.5) with a G-25 size exclusion column, and concentrated to a concentration of about 10.0 mg/mL to obtain 2.0 mL of P-mAb acetic acid-sodium acetate buffer (0.135 mmol). 3-acetyl-mercapto-propionaldehyde (0.15 mg, 1.1 μmol) was dissolved in 0.2 mL of acetonitrile and then dropwise titrated into the above buffer solution. Sodium cyanoborohydride (173 mg, 2.7 mmol) was dissolved in 0.2 mL of water and was dropwise titrated into the above reaction solution, and then stirred at 25° C. for 3 hours. After that, the reaction solution was desalted and purified by Sephadex G25 gel column (eluting phase: 0.05 M PBS solution containing 2 mM EDTA, pH 6.3) to obtain 3.0 mL of pertuzumab-propanethiol ethyl ester (31a) solution at a concentration of 6.5 mg/mL.

Step 2

Pertuzumab-propanethiol 0.06 mL of 2 M hydroxylamine hydrochloride was added into the Pertuzumab-propanethiol ethyl ester (31a) solution (prepared in step 1), and stirred at 25° C. for 1 hour. Then, the reaction solution was desalted and purified by Sephadex G25 gel column (eluting phase: 0.05 M PBS solution containing 2 mM EDTA, pH 6.3) to obtain 5.0 mL of pertuzumab-propanethiol (31b) solution at a concentration of 3.8 mg/mL.

Step 3

Pertuzumab-propyl-1-sulfur-MC-VC-PAB-MMAE

Compound 1 (MC-VC-PAB-MMAE, 1.7 mg, 1.4 μmol) was dissolved in 0.55 mL of acetonitrile and was added into pertuzumab-propanethiol (31b) solution (prepared in step 2). After stirring at 25° C. for 4 hours, the reaction solution was desalted and purified by a Sephadex G25 gel column (eluting phase: 0.05 M PBS solution containing 2 mM EDTA, pH 6.3), concentrated and filtrated under a sterile condition through a 0.2 μm filter to obtain 8.0 mL of pertuzumab-propyl-1-sulfur-MC-VC-PAB-MMAE (compound 34) at a concentration of 2.4 mg/mL, and then stored at −20° C. frozen storage.

Example 8

Preparation of Antibody Drug Conjugate Compound 35 as Positive Control

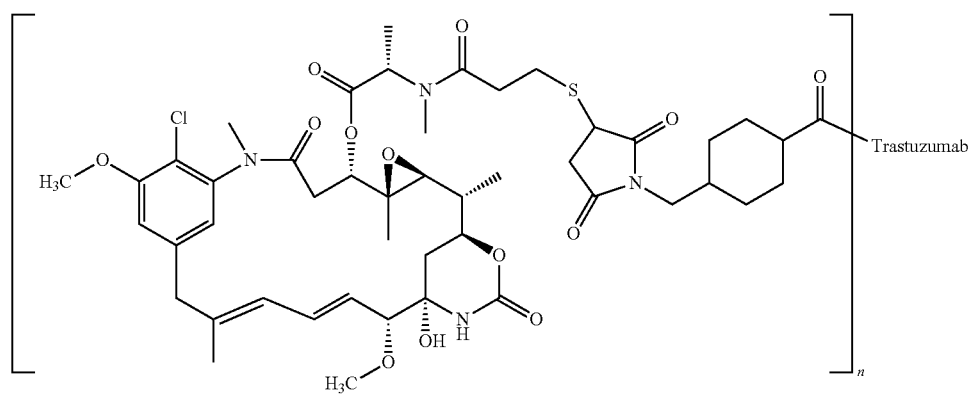

The synthetic route is as follows:

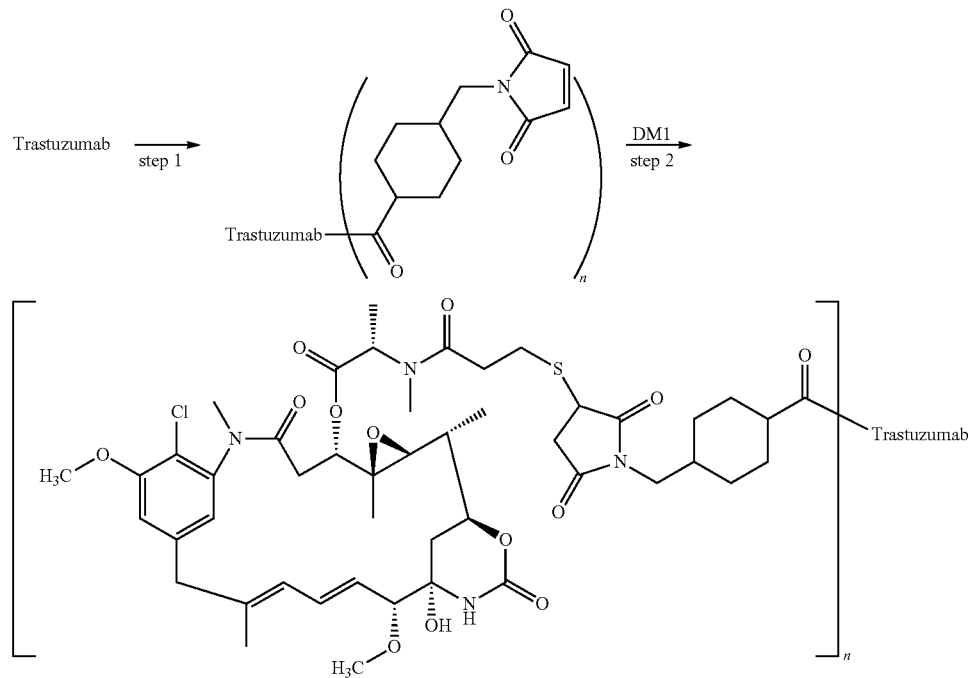

The antibody drug conjugate compound 35 was prepared by a method disclosed in U.S. Patent Application Publication No. 20050169933.

The following test examples serve to illustrate the invention, but the examples should not be considered as limiting the scope of the invention.

TEST EXAMPLES

Biological Evaluation

Test Example 1

BT474 Cell Proliferation Assay

Purpose

To test the inhibitory effects of the samples of the present invention on the proliferation of BT474 cells.

Materials:

Samples of the present invention: antibody drug conjugate compound 16 (hereinafter referred to as "compound"), compound 17, compound 18, and compounds 31-34;

Positive control drug: compound 35;

BT474 cell: purchased from Chinese Academy of Sciences Cell Bank, Catalog No: TCHu 143;

CCK-8: Cell Counting Kit-8, available from Dojindo, Catalog No: CK04;

FBS: Fetal Bovine Serum, available from Gibco, Catalog No: 10099-141;

RPMI1640: available from Hyclone, Catalog No: SH30809.01B;

NOVOSTAR Multifunctional Microplate Reader (BMG).

Process:

1. 100 μL of RPMI1640 medium containing 10% FBS and 15,000 BT474 cells were added into each well of a 96-well plate, and cultured in the incubator at 37° C., 5% $CO_2$.

2. The sample was two-fold gradient diluted with RPMI1640 medium-containing 10% FBS, 9 dilutions total, and the initial concentration was 5 μg/mL.

3. The diluted drugs were transferred to a 96-well plate, which was pre-plated with BT474 cells, 50 μL/well. Each concentration was added in triplicate. Meanwhile, wells without any drug were set as control in triplicate. Thereafter, the cells were continuously cultured under conditions of 37° C., 5% $CO_2$.

4. 96 hours later, each well was added with 10 μL of CCK-8 solution for color development, and placed in the incubator at 37° C., 5% $CO_2$. After 4 hours of color development, the $OD_{450}$ value was read on an ELISA microplate reader, and the $IC_{50}$ value was obtained using Graphpad Prism 5 software.

Results:

Biological activity of the compounds of the present invention was obtained by the above procedures; the calculated $IC_{50}$ values are listed in Table 1 below:

TABLE 1

$IC_{50}$ of the compounds of the present invention for inhibiting BT474 cell proliferation

| No. of compound | $IC_{50}$ (BT474)/nM |
| --- | --- |
| 35 | 1.867 |
| 16 | 0.358 |
| 17 | 3.38 |
| 18 | 0.152 |
| 19 | 0.124 |

Conclusion: All of the preferred compounds of the present invention have significant inhibitory activity on BT474 cell proliferation.

Test Example 2

Daudi Cell Proliferation Assay

Purpose:

To test the inhibitory effects of the samples of the present invention on the proliferation of Daudi cells.

Materials and Equipment:

Samples of the present invention: Compound 22, Compound 23, Compound 24, Compound 25;

RPMI1640: available from Hyclone, Catalog No.: SH30809.01B;

Pen Strep (P/S), purchased from Gibco, Catalog No. 15140;

CCK-8: Cell Counting Kit-8, available from Dojindo, Catalog No.: CK04;

75 cm TC-Treated Culture Flask, available from Corning Incorporated, Item: 430641;

PBS: purchased from Gibco, Catalog No.: 20012-027;

Daudi human Burkitt's lymphoma cells, purchased from Chinese Academy of Sciences Cell Bank, Catalog No.: TcHu140;

NOVOSTAR Multifunctional Microplate Reader (BMG);

Antibody Inotuzumab: positive control.

Process:

1. Daudi human Burkitt's lymphoma cells were incubated in RPMI-1640 medium containing 10% FBS and 1% P/S. On the day of the experiment, the cell density was adjusted to $5 \times 10^4$ cells/mL, and 90 μl of medium was added into each well of a 96-well plate.

2. The sample was four-fold gradient diluted with PBS, 9 dilutions total; and the initial concentration was 2.5 μg/ml.

3. The diluted drugs were transferred to a 96-well plate which was pre-plated with Daudi human Burkitt's lymphoma cells, 10 μL/well. Control wells were added with 10 μl of PBS. Thereafter, the cells were continuously cultured in an incubator at 37° C., 5% $CO_2$.

4. 72 hours later, each well was added with 10 μL of CCK-8 developing solution, and placed in the incubator at 37° C., 5% $CO_2$. After 4 hours of development, the $OD_{450}$ value was read on an ELISA microplate reader, and the $IC_{50}$ value was obtained using Graphpad Prism 5 software.

TABLE 2

$IC_{50}$ of the compounds of the present invention for inhibiting proliferation of Daudi human Burkitt's lymphoma cells

| Compound No. | $IC_{50}$ (Daudi)/nM |
| --- | --- |
| Inotuzumab | 95.6 |
| 22 | 1.43 |
| 23 | 22.71 |
| 24 | 0.511 |
| 25 | 5.94 |

Conclusion: All the preferred compounds of the present invention have a significant effect in inhibiting proliferation of the Daudi human Burkitt's lymphoma cells.

Test Example 3

Test of Inhibition Rate of NCI-N87

Purpose

To evaluate and compare the efficacy of antibody cytotoxic conjugates of the present invention on inhibiting the growth of human gastric cancer NCI-N87 cell (ATCC, CRL-5822) xenografts in nude mice.

Test Drugs

Samples of the present invention: Compound 16; Compound 17; Compound 18; and Compound 31;

Positive control drug: Compound 35;

Preparation method: formulated with saline.

Animals

BALB/cA-nude mice, 6-7 weeks, female, purchased from Shanghai SLAC laboratory Animal Co., Ltd. Certificate No.: SCXK (Shanghai) 2012-0002. Housing environment: SPF level.

Process:

Nude mice were inoculated subcutaneously with NCI-N87 human gastric cancer cells. When the tumor volume reached 100-200 mm³, the animals were grouped randomly (D0). The dosage and schedule are shown in Table 1. The tumor volume and weight were measured 2-3 times per week, and the data was recorded. Tumor volume (V) was calculated as follows:

$$V = \tfrac{1}{2} \times a \times b^2$$

Wherein: a and b represent length and width, respectively.
$T/C\ (\%) = (T - T_0)/(C - C_0) \times 100\%$, wherein T and C were measured at the end of the experiment; $T_0$ and $C_0$ were measured at the beginning of the experiment.

TABLE 3

Efficacy of compounds (16, 17, 18, 35) on NCI-N87 human gastric cancer xenografts in nude mice

| Compound group | Dosing dosing | Dosing route | Mean tumor volume (mm³) D0 | SD | Mean tumor volume (mm³) D17 | SD | % T/C D17 | % Inhibition rate D17 | P value D17 | Partial regression | Animals per group |
|---|---|---|---|---|---|---|---|---|---|---|---|
| solvent | D0,7,14 | IV | 135.4 | ±11.5 | 1054.8 | ±170.9 | — | — | — | 0 | 10 |
| 16 (3 mg/kg) | D0,7,14 | IV | 136.1 | ±9.8 | 273.3 | ±183.5 | 15 | 85 | 0.000 | 1 | 6 |
| 16 (10 mg/kg) | D0,7,14 | IV | 134.3 | ±9.8 | 59.7 | ±8.7 | −56 | 156 | 0.000 | 6 | 6 |
| 17 (3 mg/kg) | D0,7,14 | IV | 128.4 | ±9.5 | 888.3 | ±169.3 | 83 | 17 | 0.085 | 0 | 6 |
| 17 (10 mg/kg) | D0,7,14 | IV | 139.6 | ±12.4 | 602.7 | ±130.3 | 50 | 50 | 0.000 | 0 | 6 |
| 18 (3 mg/kg) | D0,7,14 | IV | 131.6 | ±13.5 | 366.7 | ±100.3 | 26 | 74 | 0.000 | 0 | 6 |
| 18 (10 mg/kg) | D0,7,14 | IV | 133.4 | ±17.2 | 66.3 | ±8.3 | −50 | 150 | 0.000 | 6 | 6 |
| 35 (3 mg/kg) | D0,7,14 | IV | 137.1 | ±10.5 | 446.9 | ±69.6 | 34 | 66 | 0.000 | 0 | 6 |
| 35 (10 mg/kg) | D0,7,14 | IV | 136.2 | ±5.2 | 74.5 | ±18.2 | −45 | 145 | 0.000 | 6 | 6 |

D0: time of first administration.
P value, versus control group; the number of mice at the beginning of the experiment: control group, n = 10, treatment group, n = 6.

TABLE 4

Efficacy of compound (31, 35) on NCI-N87 human gastric cancer xenografts in nude mice

| Compound group | Dosing dosing | Dosing approach | Mean tumor volume (mm³) D0 | SEM | Mean tumor volume (mm³) D21 | SEM | % T/C D21 | % Inhibition rate D21 | P value D21 | Partial regression | Complete regression | Animals per group at the end |
|---|---|---|---|---|---|---|---|---|---|---|---|---|
| solvent | D0,7 | IV | 117.3 | ±3.2 | 1247.9 | ±144.8 | — | — | — | 0 | 0 | 10 |
| 31 (1 mg/kg) | D0,7 | IV | 116.0 | ±5.4 | 708.2 | ±77.3 | 52 | 48 | 0.017 | 0 | 0 | 6 |
| 31 (3 mg/kg) | D0,7 | IV | 120.3 | ±6.1 | 99.3 | ±11.4 | −18 | 118 | 0.000** | 4 | 0 | 6 |
| 31 (10 mg/kg) | D0,7 | IV | 116.4 | ±3.3 | 0.0 | ±0.0 | −100 | 200 | 0.000 | 0 | 6 | 6 |
| 35 (3 mg/kg) | D0,7 | IV | 115.3 | ±5.5 | 277.1 | ±45.2 | 14 | 86 | 0.000 | 0 | 0 | 6 |

TABLE 4-continued

Efficacy of compound (31, 35) on NCI-N87 human gastric cancer xenografts in nude mice

| Compound group | Dosing dosing | Dosing approach | Mean tumor volume (mm³) D0 | SEM | Mean tumor volume (mm³) D21 | SEM | % T/C D21 | % Inhibition rate D21 | P value D21 | Partial regression | Complete regression | Animals per group at the end |
|---|---|---|---|---|---|---|---|---|---|---|---|---|
| 35 (10 mg/kg) | D0,7 | IV | 109.8 | ±4.3 | 23.9 | ±15.1 | −78 | 178 | 0.000 | 2 | 4 | 6 |

D0: Time of first administration;
P value versus solvent group,
**p < 0.01, versus group of 3 mg/kg of compound 35;
For all, Student's t test was used.
Number of Mice at the beginning of the experiment: control group n = 10, treatment group n = 6.

Results

Figure 2:
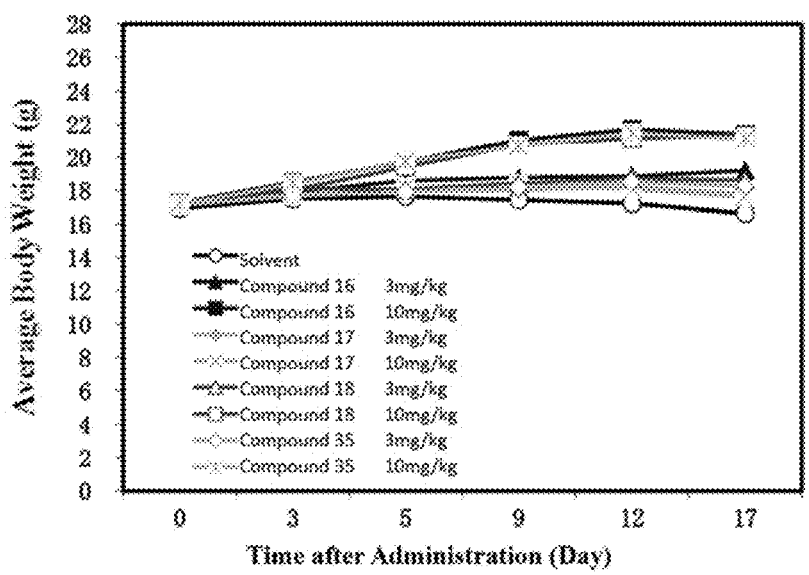

In the first experimental group, the compound 16 (3, 10 mg/kg, IV, D0, 7, 14) significantly inhibited the growth of HER2-highly-expressing gastric cancer NCI-N87 subcutaneously transplanted into nude mice, the inhibition rate was 85% and 156% respectively, and partial tumor regression was caused in 1/6 and 6/6 mice. For the same dosage and schedule of compound 18, the inhibition rate on NCI-N87 was 74% and 150%, respectively, wherein the higher dose caused partial tumor regression in 6/6 mice; The inhibition rate of the control compound 35 on NCI-N87 was 66% and 145%, respectively, wherein the higher dose caused partial tumor regression in 6/6 mice. The inhibition rate of the control compound 17 on NCI-N87 was 17% and 50%, respectively. The tumor-bearing mice were well tolerated to the drugs indicated above. The inhibitory effects of test drugs on tumor growth are shown in Table 1 and FIG. 1. No deaths occurred during the administration, and the body weight of each group of mice was not significantly decreased during the administration, as shown in FIG. 2, suggesting that the current dose had no significant side effects.

In the second experimental group, compound 31 (1, 3, 10 mg/kg, IV, once per week, totally twice) dose-dependently inhibited the growth of HER2-highly-expressing gastric cancer NCI-N87 subcutaneously transplanted into nude mice, and the inhibition rate was 48%, 118% and 200%, respectively. For the 3 mg/kg group, partial tumor regression was shown in 4/6, and for the 10 mg/kg group, complete tumor regression was shown in 6/6. For control compound 35 (3, 10 mg/kg, IV, once per week, total twice), the inhibition rate on NCI-N87 was 86% and 178%, respectively. For the 10 mg/kg group, partial tumor regression was displayed in 2/6, and complete tumor regression was seen in 4/6. Tumor bearing mice tolerated these drugs well. The efficacy of compound 31 on NCI-N87 was stronger than that of positive control compound 35 (P<0.01, compared with 3 mg/kg group) (Table 4).

Test Example 4

SK-BR-3 Cell Proliferation Assay

Purpose:

Test the inhibitory effect of samples on the proliferation of Daudi cells by using CCK method, and evaluate in vitro activity of samples according to $IC_{50}$.

Materials:

SK-BR-3 cells: ATCC, Catalog No: HTB-30;

McCoy's 5A medium: purchased from Gibco, Catalog No: 16600-108;

CCK-8: Cell Counting Kit-8, available from Dojindo, Catalog No: CK04;

PBS: purchased from Gibco, Catalog No: 20012-027;

Process:

1. SK-BR-3 cells were cultured in McCoy's 5A medium containing 10% FBS, passaged twice to three times per week at a passage ratio of 1:3 or 1:6. For cell passage, the medium was aspirated, the cell adherence layer was washed with 5 mL of 0.25% trypsin, then the trypsin was aspirated, the cells were digested for 3 to 5 minutes in the incubator, and then resuspended with the addition of fresh medium.

2. 100 μL cell suspension was added into each well of a 96-well plate at a cell density of $5×10^4$ cells/mL with culture medium of McCoy's 5A medium containing 10% FBS, and the periphery of 96-well plate was only added with 100 μL of McCoy's 5A medium containing 10% FBS.

3. After 24 hours of cell adherence, the medium was removed, and 90 μL of McCoy's 5A medium containing 2% FBS was added into each well.

4. The sample was gradient diluted to different concentrations with PBS, and 10 μL of sample with different concentrations was added into each well of a 96-well plate. Each concentration was repeated in duplicate.

5. The plate was incubated for 3 days in the incubator (37° C., 5% $CO_2$).

6. 10 μL of CCK-8 solution was added into each well (being careful not to create bubbles in the wells, since it may affect the reading of OD values)

7. After 3 hours of incubation in the incubator, the absorbance value was read on an ELISA microplate reader at 450 nm.

Results:

| Compound No | SK-BR-3 IC50 (ng/mL) |
|---|---|
| 31 | 5.94 |
| 35 | 54.75 |

Conclusion: the preferred compounds of the present invention have a significant inhibitory effect on the proliferation of SK-BR-3 cells.

We claim:

1. A ligand-cytotoxic drug conjugate of formula (I), or a pharmaceutically acceptable salt or solvate thereof:

Pc―(―X―Y-D)$_n$  (I)

wherein Pc is an antibody;
Y is an interval unit;
D is a cytotoxic drug;
n is selected from 1 to 8;
X is a connecting unit linked to at least one of an N-terminal amino group of the antibody of the ligand Pc and an ε-amino group of a lysine residue of the antibody of the ligand Pc, wherein the connecting unit X has the following structure:

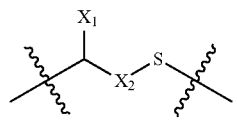

X wherein $X_1$ is selected from the group consisting of H, alkyl, cycloalkyl, heterocyclyl, aryl and heteroaryl, wherein the alkyl, cycloalkyl, heterocyclyl, aryl and heteroaryl are each independently and optionally substituted with one or more groups selected from the group consisting of halogen, hydroxy, cyano, alkyl, alkoxy, cycloalkyl, heterocyclyl, aryl and heteroaryl, $X_2$ is selected from the group consisting of alkyl, cycloalkyl, alkyl-cycloalkyl, cycloalkyl-alkyl, alkyl-cycloalkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, $(CH_2)_p(OCH_2CH_2)_p$, and $(CH_2CH_2O)_p(CH_2)_p$, each p is an integer independently selected from 1 to 10, wherein the alkyl, cycloalkyl, heterocyclyl, aryl and heteroaryl are each independently and optionally substituted with one or more groups selected from the group consisting of halo, hydroxy, cyano, alkyl, alkoxy, cycloalkyl, heterocyclyl, aryl and heteroaryl, or when $X_1$ is not H, $X_1$ and $X_2$ with the carbon atom joining $X_1$ and $X_2$ are taken together to form a cycloalkyl group, wherein the cycloalkyl is independently and optionally substituted with one or more groups selected from the group consisting of halo, hydroxy, cyano, alkyl, alkoxy, cycloalkyl, heterocyclyl, aryl and heteroaryl; and S is a sulfur atom.

2. The ligand-cytotoxic drug conjugate or the pharmaceutically acceptable salt or solvate thereof according to claim 1, wherein $X_1$ is H or alkyl.

3. The ligand-cytotoxic drug conjugate or the pharmaceutically acceptable salt or solvate thereof according to claim 1, wherein $X_2$ is alkyl or aryl.

4. The ligand-cytotoxic drug conjugate or the pharmaceutically acceptable salt or solvate thereof according to claim 1, wherein the antibody is specific for a cell surface antigen expressed on at least one of a target cell and tissue of a proliferative disease.

5. The ligand-cytotoxic drug conjugate or the pharmaceutically acceptable salt or solvate thereof according to claim 4, wherein the cell surface antigen is selected from the group consisting of: HER2 (ErbB2), HER3 (ErbB3), HER4 (ErbB4), CD20, CD22, CD30, CD33, CD44, Lewis Y, CD56, CD105, VEGFR, and GPNMB.

6. The ligand-cytotoxic drug conjugate or the pharmaceutically acceptable salt or solvate thereof according to claim 5, wherein the cell surface antigen is selected from the group consisting of: HER2 (ErbB2), CD22, CD30, CD33, CD44, CD56, Lewis Y, and GPNMB.

7. The ligand-conjugate or the pharmaceutically acceptable salt or solvate thereof according to claim 1, wherein the antibody is selected from the group consisting of: Trastuzumab, Inotuzumab, Pinatuzumab, Brentuximab, Gemtuzumab, Bivatuzumab, Lorvotuzumab, cBR96, Glematumamab and Pertuzumab.

8. The ligand-cytotoxic drug conjugate or the pharmaceutically acceptable salt or solvate thereof according to claim 7, wherein the antibody is capable of binding to a HER2 protein, wherein the antibody comprises:
1) a light chain comprising CDR-L1, CDR-L2 and CDR-L3 sequences defined according to Kabat numbering system, wherein:
i) CDR-L1 is a CDR of SEQ ID NO: 7;
ii) CDR-L2 is a CDR of SEQ ID NO: 8;
iii) CDR-L3 is a CDR of SEQ ID NO: 9; and
2) a heavy chain comprising CDR-H1, CDR-H2 and CDR-H3 sequences defined according to Kabat numbering system, wherein:
iv) CDR-H1 is a CDR of SEQ ID NO: 10;
v) CDR-H2 is a CDR of SEQ ID NO: 11;
vi) CDR-H3 is a CDR of SEQ ID NO: 12.

9. The ligand-cytotoxic drug conjugate or the pharmaceutically acceptable salt or solvate thereof according to claim 8, wherein the antibody capable of binding to the HER2 protein comprises a light chain and a heavy chain, wherein the light chain comprises the amino acid sequence of SEQ ID NO: 13, and the heavy chain comprises the amino acid sequence of SEQ ID NO: 14.

10. The ligand-cytotoxic drug conjugate or the pharmaceutically acceptable salt or solvate thereof according to claim 1, wherein the cytotoxic drug is selected from the group consisting of tubulin inhibitors, topoisomerase inhibitors, DNA alkylating agents, tyrosine kinase inhibitors, and DNA synthesis inhibitors.

11. The ligand-cytotoxic drug conjugate or the pharmaceutically acceptable salt or solvate thereof according to claim 10, wherein the cytotoxic drug is a tubulin inhibitor selected from the group consisting of maytansinoids, calicheamicin, taxanes, vincristine, colchicine, and Dolastatins/Auristatins.

12. The ligand-cytotoxic drug conjugate or the pharmaceutically acceptable salt or solvate thereof according to claim 1, wherein D is selected from the group consisting of Dolastatins/Auristatins having a structure of formula ($D_1$):

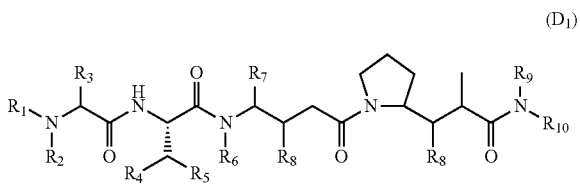

wherein:
$R_1$ is a bond, H, alkyl or cycloalkyl;
$R_2$ is H or alkyl;
or $R_1$ and $R_2$ with the joined N atom are taken together to form a heterocyclyl, wherein the heterocyclyl is independently and optionally substituted with one or more groups selected from the group consisting of halo, hydroxy, cyano, alkyl, alkoxy, cycloalkyl, heterocyclyl, aryl, and heteroaryl; or form a structure of —$(CR_aR_b)_e$—, wherein $R_a$ and $R_b$ are independently selected from the group consisting of H, alkyl, and heterocyclyl, and e is an integer selected from 2 to 6;
$R_3$ is selected from the group consisting of H, alkyl, cycloalkyl, aryl, alkyl-aryl, alkyl-cycloalkyl, heterocyclyl and alkyl-heterocyclyl;
$R_4$ is selected from the group consisting of H, alkyl, cycloalkyl, aryl, alkyl-aryl, alkyl-cycloalkyl, heterocyclyl and alkyl-heterocyclyl;
$R_5$ is H or methyl;
$R_6$ is H or alkyl;
$R_7$ is selected from the group consisting of H, alkyl, cycloalkyl, aryl, alkyl-aryl, alkyl-cycloalkyl, heterocyclyl and alkyl-heterocyclyl;
$R_8$ is selected from the group consisting of H, hydroxy, alkyl, cycloalkyl, and alkoxy;
$R_9$ is H or alkyl;
when $R_1$ is alkyl or cycloalkyl, or $R_1$ and $R_2$ with the joined N atom are taken together to form a heterocyclyl, wherein the heterocyclyl is independently and optionally substituted with one or more groups selected from the group consisting of halo, hydroxy, cyano, alkyl, alkoxy, cycloalkyl, heterocyclyl, aryl, and heteroaryl, $R_{10}$ is selected from the following structures:

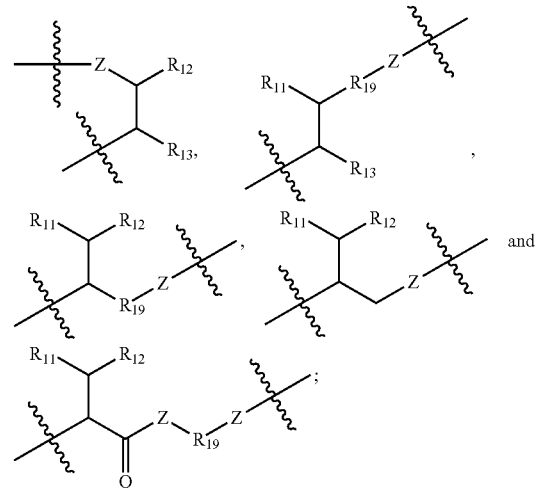

when $R_1$ is H, $R_{10}$ is selected from the following structures:

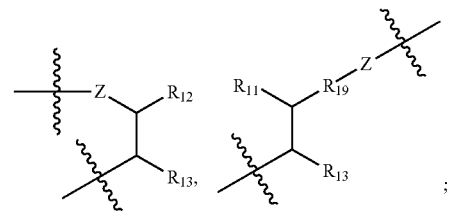

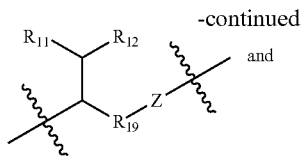

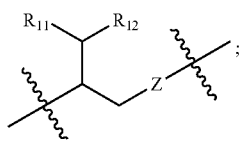

when R₁ is a bond, R₁ is connected to the interval unit Y, wherein $R_{10}$ is selected from the following structures:

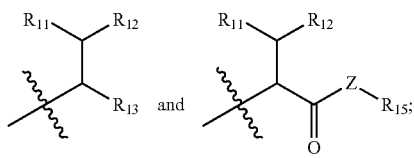

Z is selected from the group consisting of O, S, NH and $N(R_{14})$;

$R_{11}$ is selected from the group consisting of H, hydroxy, amino, $NHR_{14}$, $N(R_{14})_2$ alkoxy, alkyl, cycloalkyl, aryl, heterocyclyl, alkyl-aryl, alkyl-cycloalkyl, and alkyl-heterocyclyl; or when $R_{11}$ is O, it can replace H attached on the joined carbon atom, and form a carbonyl group (C=O) with this carbon atom;

$R_{12}$ is selected from the group consisting of aryl and heterocyclyl, the aryl or heterocyclyl is optionally substituted by one or more groups selected from the group consisting of hydroxy, alkoxy, alkyl, and halogen;

$R_{13}$ is selected from the group consisting of H, hydroxy, amino, $NHR_{14}$, $N(R_{14})_2$, $COOR_{14}$, alkoxy, alkyl, cycloalkyl, aryl, heterocyclyl, alkyl-aryl, alkyl-cycloalkyl, alkyl-heterocyclyl and alkoxy-alkoxy-alkoxy;

$R_{14}$ is H or alkyl;

$R_{15}$ is selected from the group consisting of H, alkyl, aryl, heterocyclic, $(R_{16}O)_m$—$R_{14}$ and $(R_{16}O)_m$—$CH(R_{17})_2$;

m is an integer selected from 1 to 1000;

$R_{16}$ is $C_2$-$C_8$ alkyl;

$R_{17}$ is selected from the group consisting of H, carboxyl, —$(CH_2)_t$—$N(R_{18})_2$ and —$(CH_2)_t$—$SO_3R_{14}$;

$R_{18}$ is selected from the group consisting of H, alkyl, and —$(CH_2)_t$—$COOH$;

t is an integer selected from 0 to 6; and $R_{19}$ is selected from the group consisting of aryl, cycloalkyl and heterocyclyl.

13. The ligand-cytotoxic drug conjugate or the pharmaceutically acceptable salt or solvate thereof according to claim 1, wherein D is maytansine having a structure of formula ($D_M$):

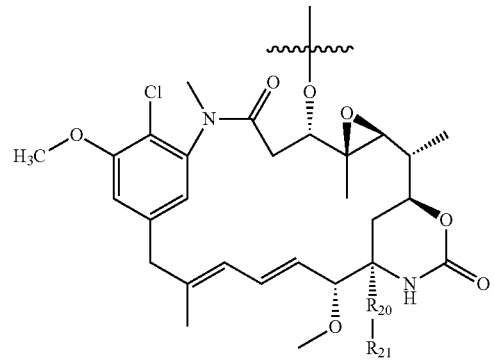

wherein:

$R_{20}$ is O or S; and $R_{21}$ is selected from the group consisting of H, alkyl, cycloalkyl, heterocyclyl, aryl, and heteroaryl, wherein the alkyl, cycloalkyl, heterocyclyl, aryl and heteroaryl are independently and optionally substituted by one or more groups selected from the group consisting of halogen, hydroxy, cyano, nitro, alkyl, alkoxy, cycloalkyl, heterocyclyl, aryl and heteroaryl.

14. The ligand-cytotoxic drug conjugate or pharmaceutically acceptable salt or solvate thereof according to claim 1, wherein the interval unit —Y— has a structure of the following formula:

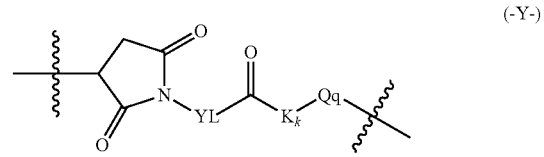

wherein:

YL is selected from the group consisting of alkyl, cycloalkyl, O-alkyl, O-alkoxy, aryl, alkyl-cycloalkyl, cycloalkyl-alkyl, alkyl-aryl, alkyl-cycloalkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, $CH_2(OCH_2CH_2)_t$, $(CH_2CH_2O)_tCH_2$, and $(CH_2CH_2O)_t$, and t is an integer selected from 1 to 10;

$K_k$ is an amino acid unit, wherein K is an amino acid, and k is an integer selected from 0 to 10; and Qq is an extended unit, wherein q is 0, 1 or 2.

15. A compound of formula (II):

$$Pc\text{-}(X\text{-}T)_n \qquad (II)$$

wherein:

Pc is an antibody;

T is selected from the group consisting of H, t-butyl, acetyl, n-propionyl, isopropionyl, triphenylmethyl, methoxymethyl, and 2-(trimethylsilyl)ethoxymethyl;

n is selected from 1 to 8; and

X is a connecting unit linked to at least one of an N-terminal amino group of the antibody Pc and an ε-amino group of a lysine residue of the antibody Pc, wherein the connecting unit X has the following structure:

X

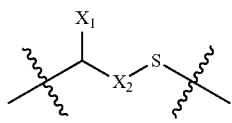

wherein $X_1$ is selected from the group consisting of H, alkyl, cycloalkyl, heterocyclyl, aryl and heteroaryl, wherein the alkyl, cycloalkyl, heterocyclyl, aryl and heteroaryl are each independently and optionally substituted with one or more groups selected from the group consisting of halogen, hydroxy, cyano, alkyl, alkoxy, cycloalkyl, heterocyclyl, aryl and heteroaryl, $X_2$ is selected from the group consisting of alkyl, cycloalkyl, alkyl-cycloalkyl, cycloalkyl-alkyl, alkyl-cycloalkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, $(CH_2)_p(OCH_2CH_2)_p$, and $(CH_2CH_2O)_p(CH_2)_p$, each p is an integer independently selected from 1 to 10, wherein the alkyl, cycloalkyl, heterocyclyl, aryl and heteroaryl are each independently and optionally substituted with one or more groups selected from the group consisting of halo, hydroxy, cyano, alkyl, alkoxy, cycloalkyl, heterocyclyl, aryl and heteroaryl, or when $X_1$ is not H, $X_1$ and $X_2$ with the carbon atom joining $X_1$ and $X_2$ are taken together to form a cycloalkyl group, wherein the cycloalkyl is independently and optionally substituted with one or more groups selected from the group consisting of halo, hydroxy, cyano, alkyl, alkoxy, cycloalkyl, heterocyclyl, aryl and heteroaryl; and S is a sulfur atom.

16. The ligand-cytotoxic drug conjugate or the pharmaceutically acceptable salt or solvate thereof according to claim 1, having a structure of formula (III):

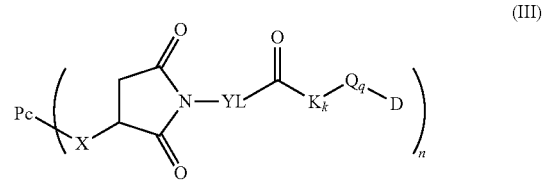

wherein:

Pc is an antibody;

X is as defined in claim 1;

YL is selected from the group consisting of alkyl, cycloalkyl, O-alkyl, O-alkoxy, aryl, alkyl-cycloalkyl, cycloalkyl-alkyl, alkyl-aryl, alkyl-cycloalkyl-alkyl, heterocyclyl, alkyl-heterocyclyl, heterocyclyl-alkyl, alkyl-heterocyclyl-alkyl, aryl, alkyl-aryl, aryl-alkyl, alkyl-aryl-alkyl, heteroaryl, alkyl-heteroaryl, heteroaryl-alkyl, alkyl-heteroaryl-alkyl, $CH_2(OCH_2CH_2)_t$, $(CH_2CH_2O)_tCH_2$, and $(CH_2CH_2O)_t$, and t is an integer selected from 1 to 10;

$K_k$ is an amino acid unit, wherein K is an amino acid, and k is an integer selected from 0 to 10;

$Q_q$ is an extended unit, wherein q is 0, 1 or 2;

n is selected from 1 to 4; and

D is a cytotoxic drug.

17. A ligand-cytotoxic drug conjugate or a pharmaceutically acceptable salt or solvate thereof selected from the group consisting of:

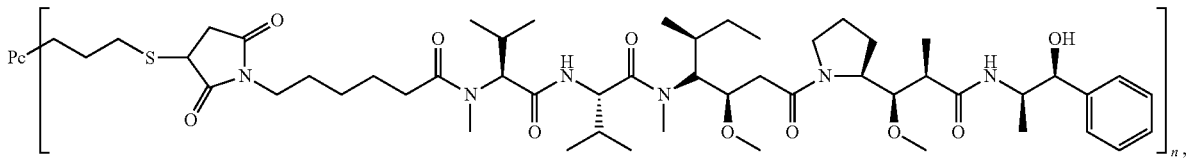

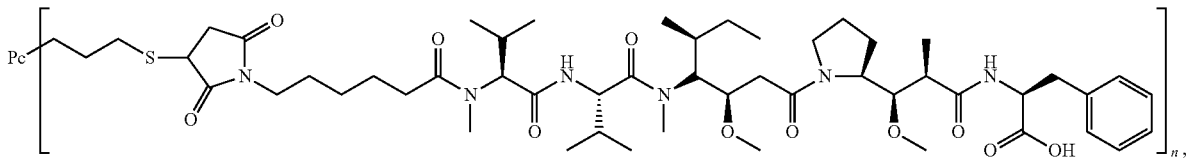

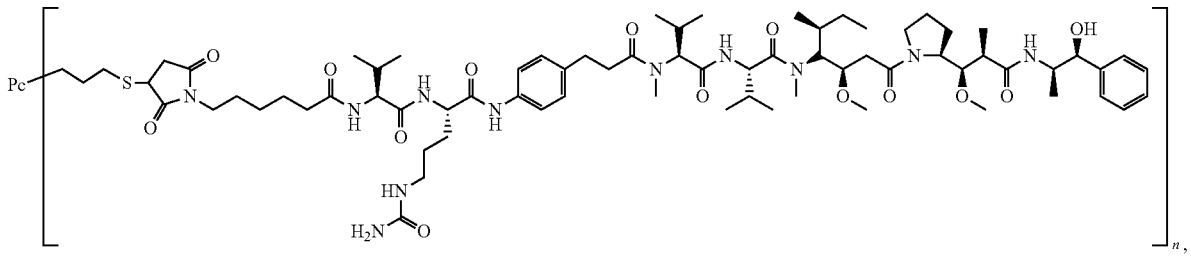

-continued
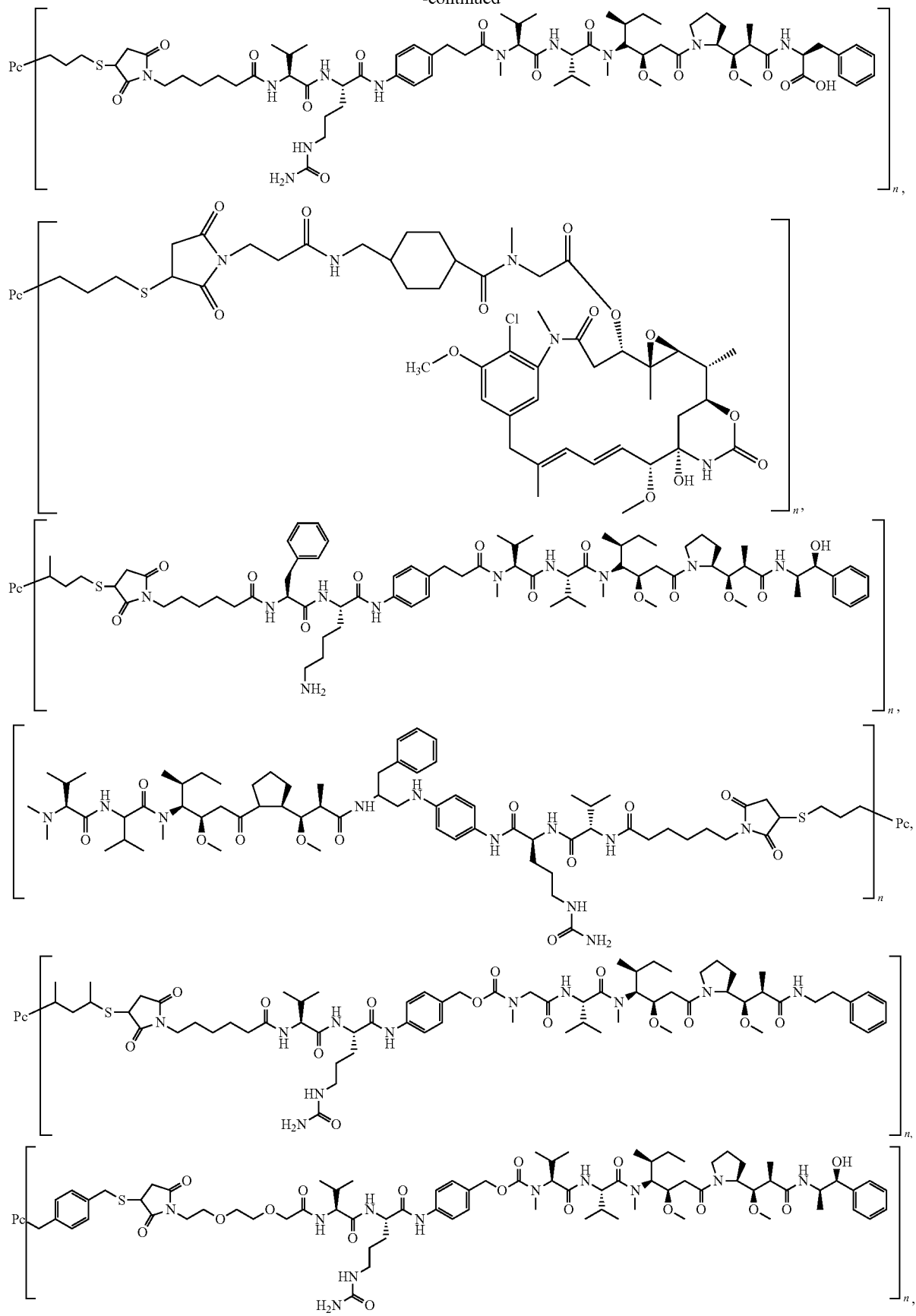

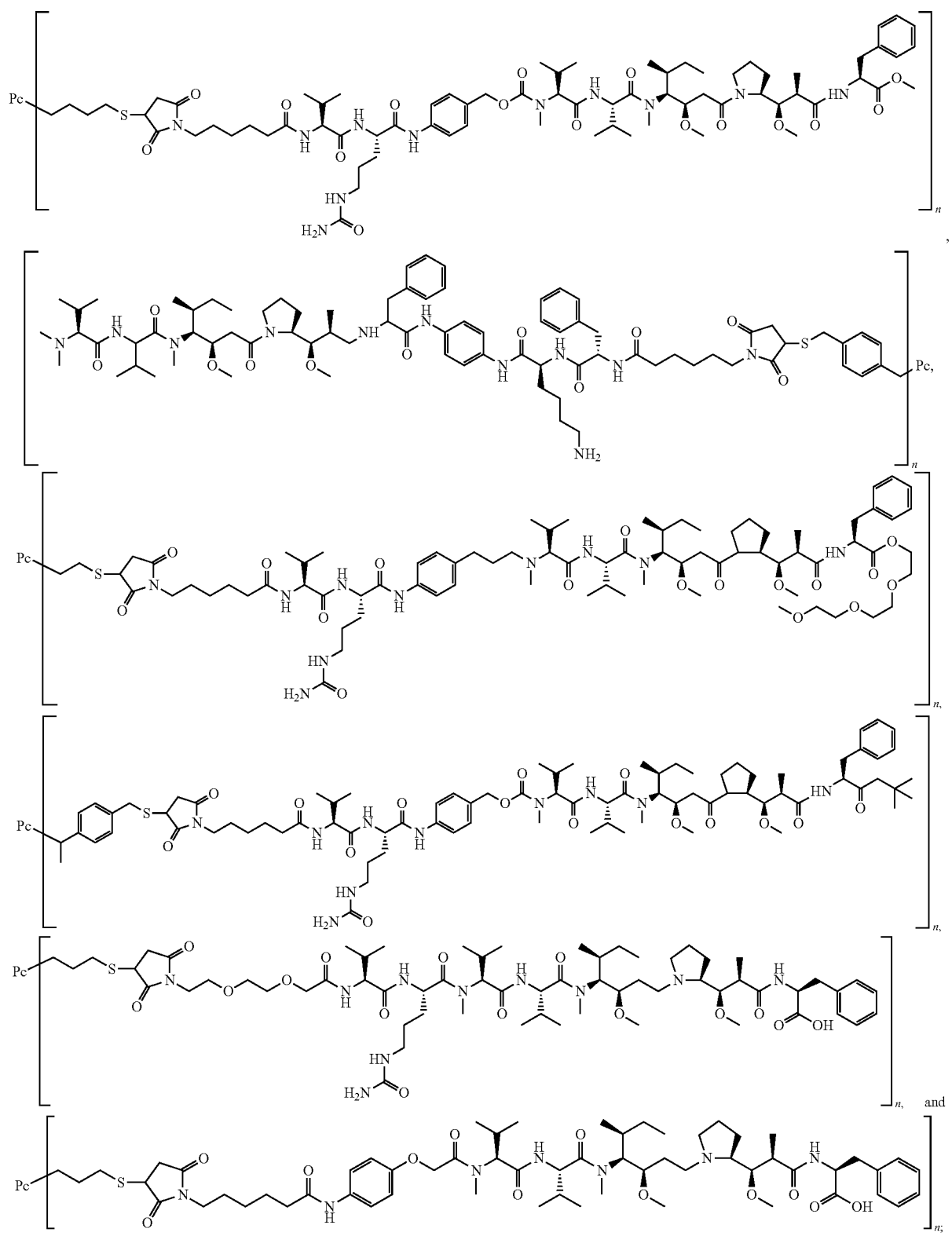

wherein Pc is an antibody, and the antibody is bonded via at least one of a N-terminal amino group of the antibody and an ε-amino group of a lysine reside of the antibody, and n is 1 to 8.

18. The ligand-cytotoxic drug conjugate or the pharmaceutically acceptable salt or solvate thereof according to claim 17, wherein Pc is selected from the group consisting of Trastuzumab, Inotuzumab and Brentuximab.

19. The ligand-cytotoxic drug conjugate or the pharmaceutically acceptable salt or solvate thereof according to claim 17, selected from the group consisting of:
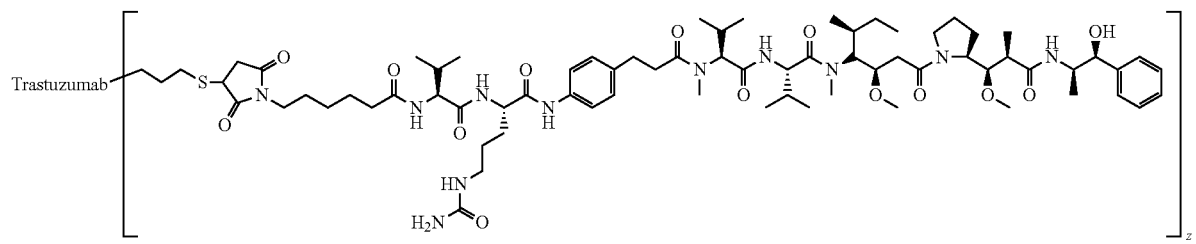
16
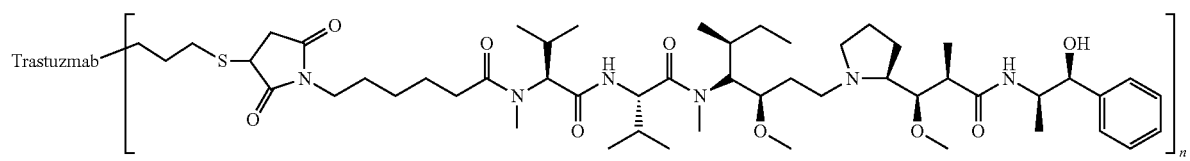
17
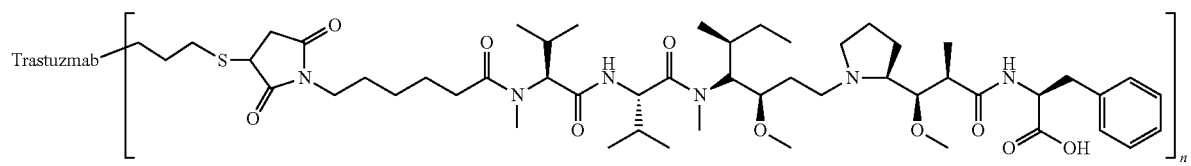
18
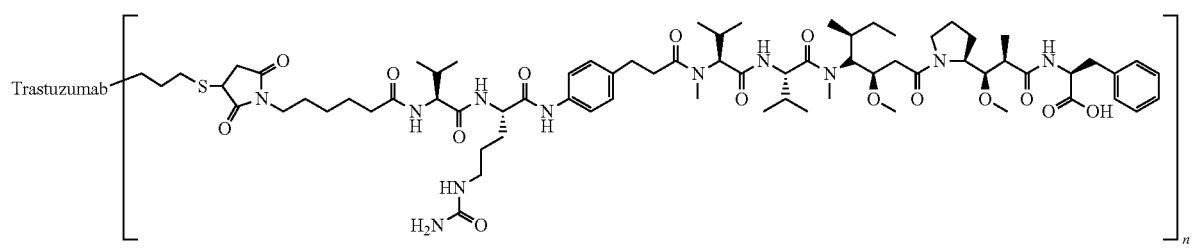
19
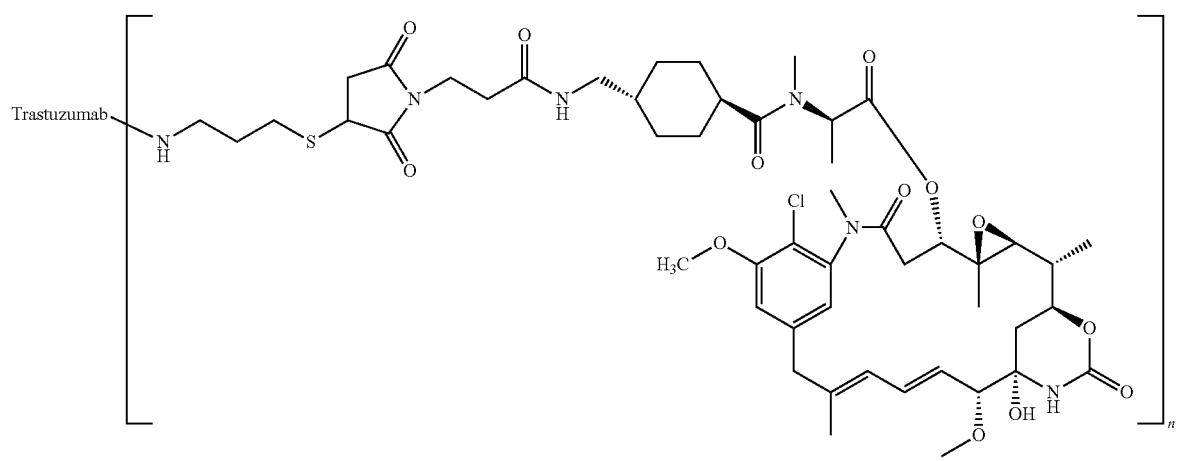
20

-continued
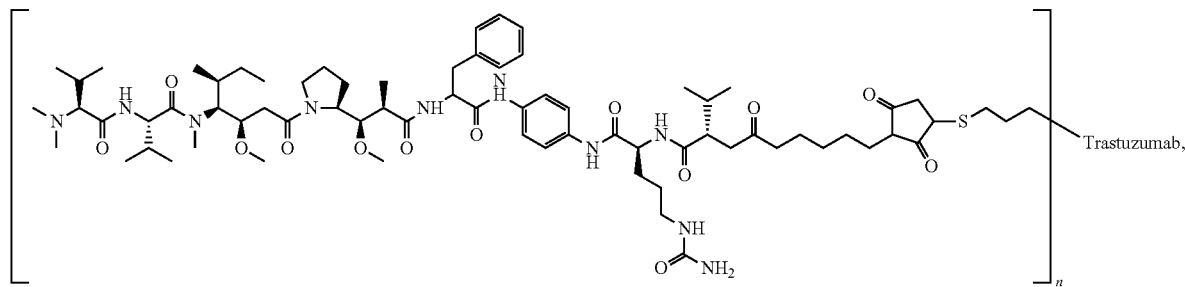
21
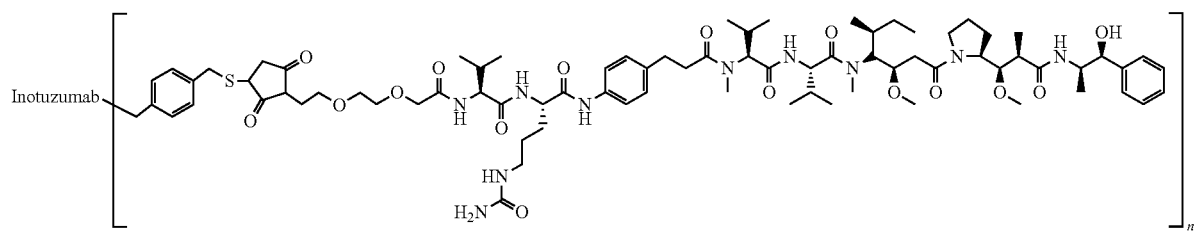
24
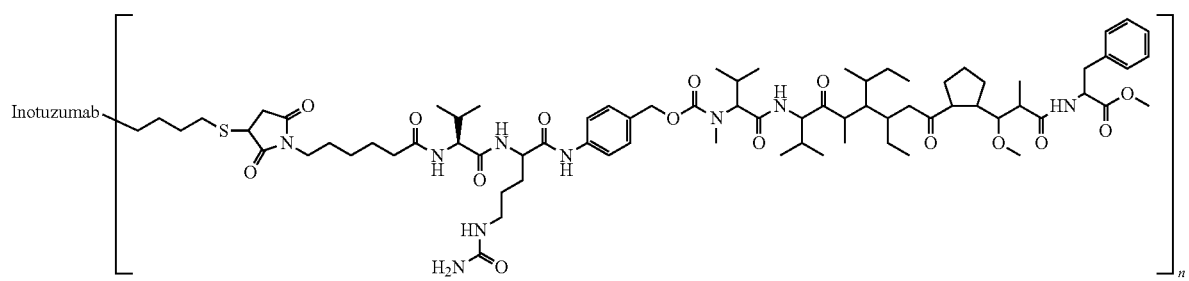
25
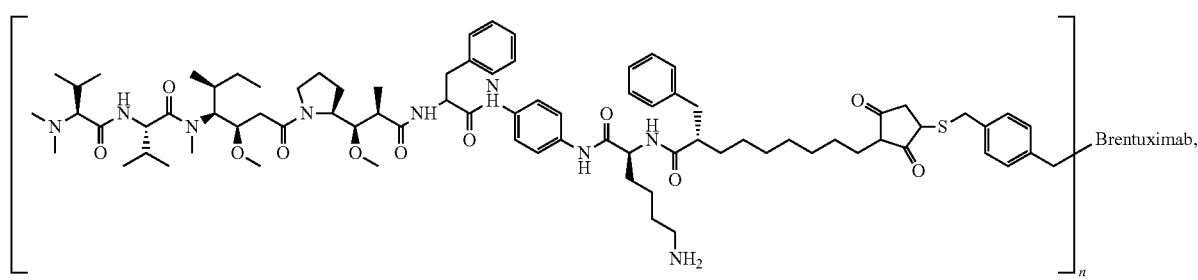
26
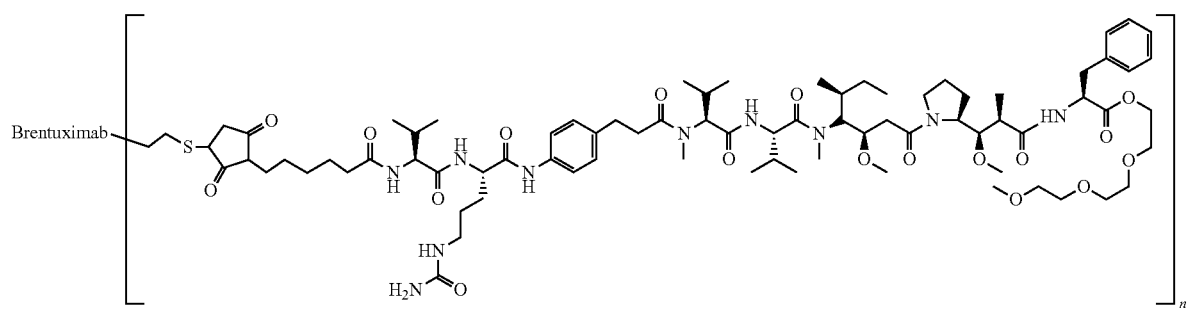
27

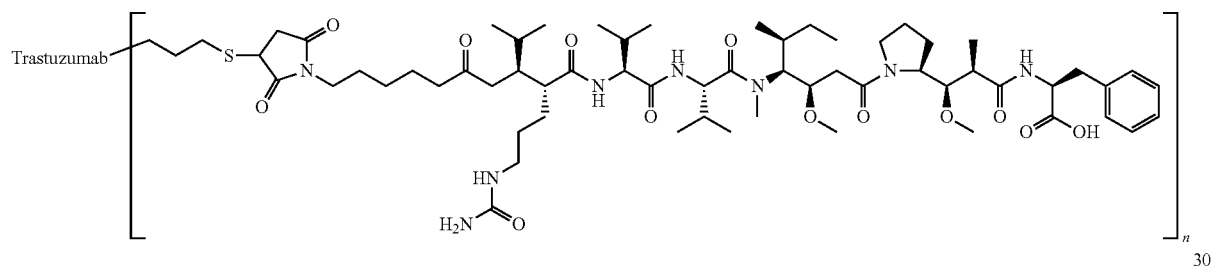

29

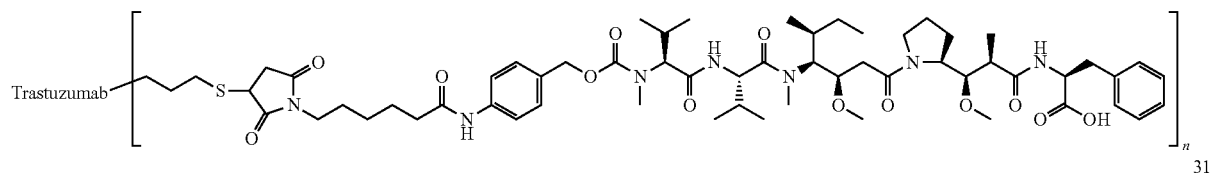

30

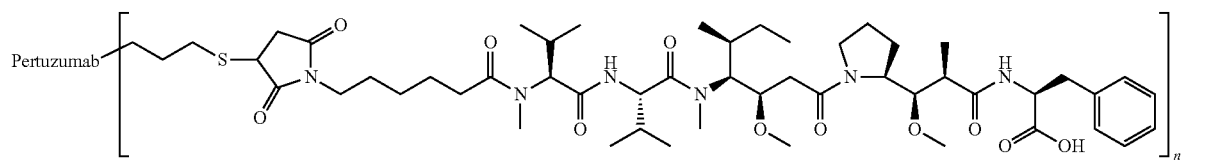

31

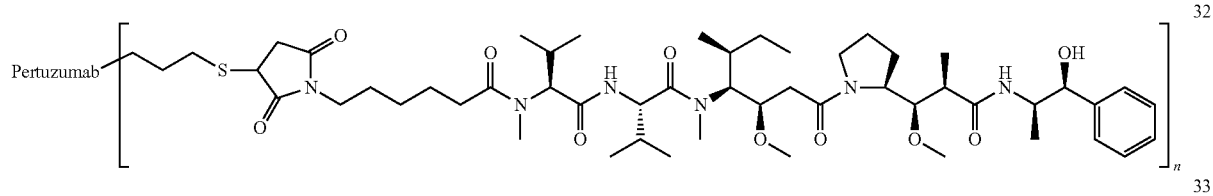

32

33

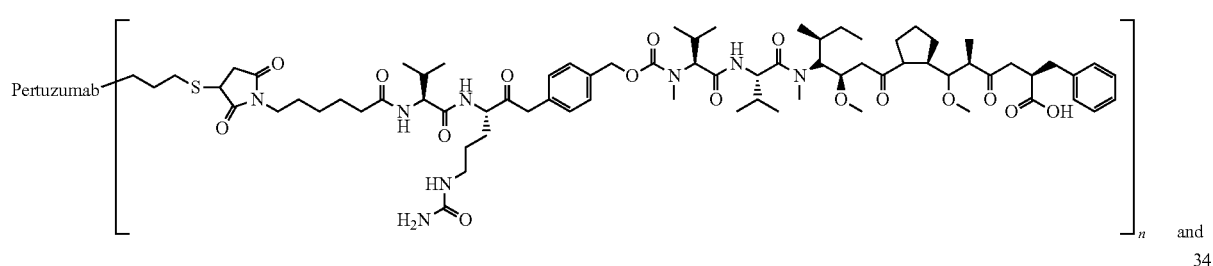

and

34

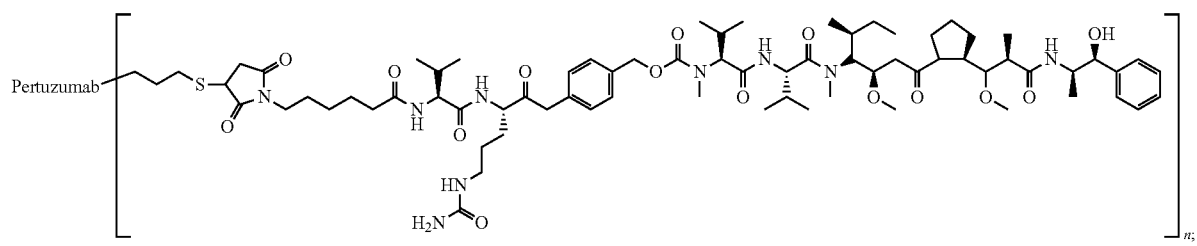

wherein n is selected from 1 to 8.

20. A process of preparing an antibody-cytotoxic drug conjugate of formula (III) according to claim 16:

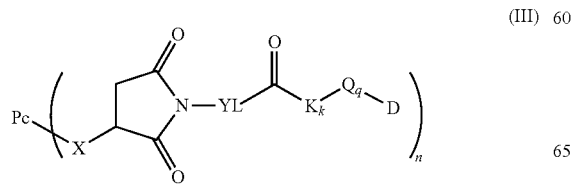

(III)

wherein the process comprises the steps of:

1) adding a reducing agent RA to a compound of formula IA and a compound of formula IB, and reacting the reducing agent RA, the compound of formula IA and the compound of formula IB at a pH of 3 to 6 and a temperature of 0° C. to 40° C., thereby obtaining a compound of formula IC;

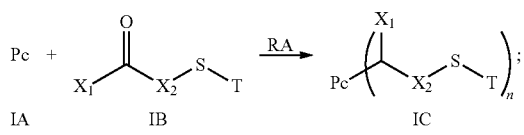

2) adding a deprotecting agent to the compound of formula IC and reacting at a temperature of 0° C. to 40° C. to remove the protective group T of the thiol group to obtain a compound of formula ID;

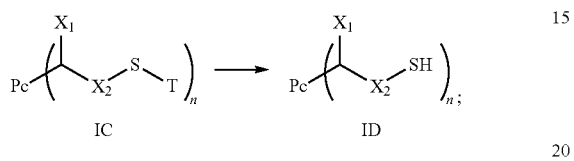

and 3) performing a Michael addition reaction between the compound of formula ID and a compound of formula IE at a temperature of 0° C. to 40° C., thereby obtaining the compound of formula (III);

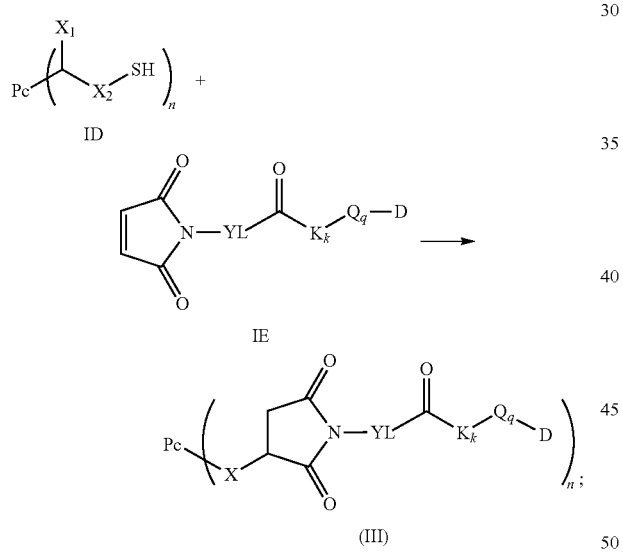

wherein $X_1$ and $X_2$ are as defined in claim 1;

Pc is an antibody;

T is selected from the group consisting of H, t-butyl, acetyl, n-propionyl, isopropionyl, triphenylmethyl, methoxymethyl, and 2-(trimethylsilyl)ethoxymethyl;

n is 1 to 8;

$K_k$ is an amino acid unit, wherein K is an amino acid, and k is an integer selected from 0 to 10;

$Q_q$ is an extended unit, wherein q is 0, 1 or 2; and

D is a cytotoxic drug selected from the group consisting of Dolstatins/Auristatins having a structure of formula ($D_1$) and maytansine having a structure of formula ($D_M$):

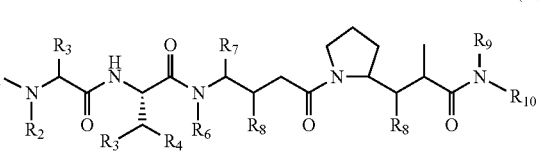

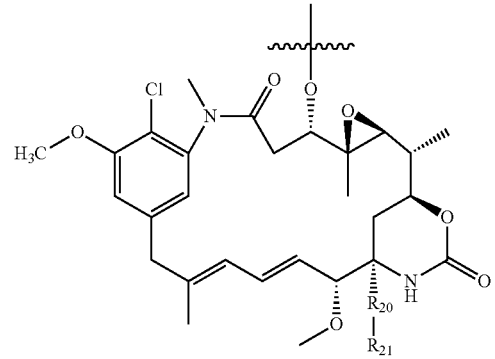

wherein:

$R_1$ is a bond, H, alkyl or cycloalkyl;

$R_2$ is H or alkyl;

or $R_1$ and $R_2$ with the joined N atom are taken together to form a heterocyclyl, wherein the heterocyclyl is independently and optionally substituted with one or more groups selected from the group consisting of halo, hydroxy, cyano, alkyl, alkoxy, cycloalkyl, heterocyclyl, aryl, and heteroaryl; or form a structure of —($CR_aR_b)_e$—, $R_a$ and $R_b$ are independently selected from the group consisting of H, alkyl, and heterocyclyl, e is an integer selected from 2 to 6;

$R_3$ is selected from the group consisting of H, alkyl, cycloalkyl, aryl, alkyl-aryl, alkyl-cycloalkyl, heterocyclyl and alkyl-heterocyclyl;

$R_4$ is selected from the group consisting of H, alkyl, cycloalkyl, aryl, alkyl-aryl, alkyl-cycloalkyl, heterocyclyl and alkyl-heterocyclyl;

$R_5$ is H or methyl;

$R_6$ is H or alkyl;

$R_7$ is selected from the group consisting of H, alkyl, cycloalkyl, aryl, alkyl-aryl, alkyl-cycloalkyl, heterocyclyl and alkyl-heterocyclyl;

$R_8$ is selected from the group consisting of H, hydroxy, alkyl, cycloalkyl, and alkoxy;

$R_9$ is H or alkyl;

when $R_1$ is alkyl or cycloalkyl, or $R_1$ and $R_2$ with the joined N atom are taken together to form a heterocyclyl, wherein the heterocyclyl is independently and optionally substituted with one or more groups selected from the group consisting of halo, hydroxy, cyano, alkyl, alkoxy, cycloalkyl, heterocyclyl, aryl, and heteroaryl, $R_{10}$ is selected from the following structures:

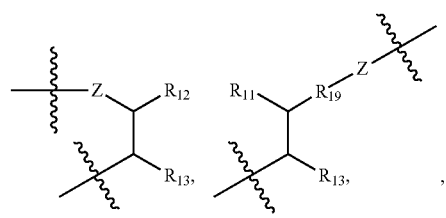

-continued

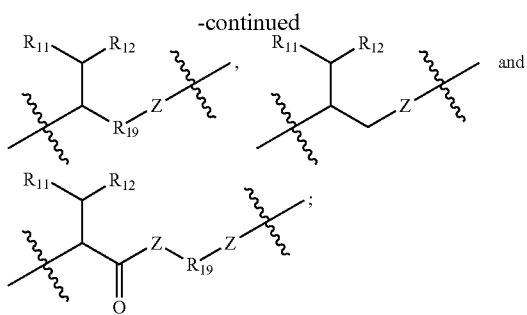

when R₁ is H, R₁₀ is selected from the following structures:

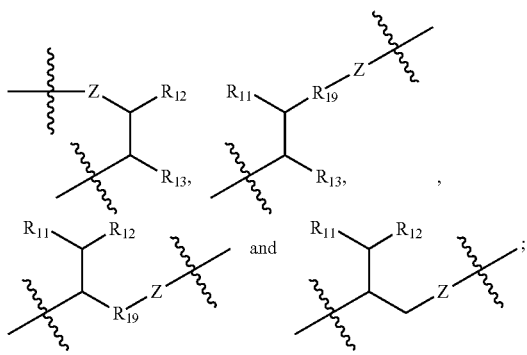

when R₁ is a bond, R₁ is connected to the interval unit Y, wherein R₁₀ is selected from the following structures:

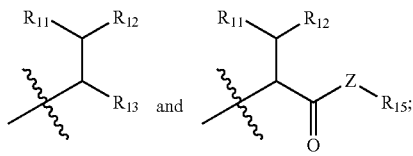

Z is selected from the group consisting of O, S, NH and N(R₁₄);

R₁₁ is selected from the group consisting of H, hydroxy, amino, NHR₁₄, N(R₁₄)₂ alkoxy, alkyl, cycloalkyl, aryl, heterocyclyl, alkyl-aryl, alkyl-cycloalkyl, and alkyl-heterocyclyl; or when R₁₁ is O, it can replace H attached on the joined carbon atom, and form a carbonyl group (C=O) with this carbon atom;

R₁₂ is selected from the group consisting of aryl and heterocyclyl, the aryl or heterocyclyl is optionally substituted by one or more groups selected from the group consisting of hydroxy, alkoxy, alkyl, and halogen;

R₁₃ is selected from the group consisting of H, hydroxy, amino, NHR₁₄, N(R₁₄)₂, COOR₁₄, alkoxy, alkyl, cycloalkyl, aryl, heterocyclyl, alkyl-aryl, alkyl-cycloalkyl, alkyl-heterocyclyl and alkoxy-alkoxy-alkoxy;

R₁₄ is H or alkyl;

R₁₅ is selected from the group consisting of H, alkyl, aryl, heterocyclic, (R₁₆O)ₘ—R₁₄ and (R₁₆O)ₘ—CH(R₁₇)₂;

m is an integer selected from 1 to 1000;

R₁₆ is C₂-C₈ alkyl;

R₁₇ is selected from the group consisting of H, carboxyl, —(CH₂)ₜ—N(R₁₈)₂ and —(CH₂)ₜ—SO₃R₁₄;

R₁₈ is selected from the group consisting of H, alkyl, and —(CH₂)ₜ—COOH;

t is an integer selected from 0 to 6;

R₁₉ is selected from the group consisting of aryl, cycloalkyl and heterocyclyl;

R₂₀ is O or S; and

R₂₁ is selected from the group consisting of H, alkyl, cycloalkyl, heterocyclyl, aryl, and heteroaryl, wherein the alkyl, cycloalkyl, heterocyclyl, aryl and heteroaryl are independently and optionally substituted by one or more groups selected from the group consisting of halogen, hydroxy, cyano, nitro, alkyl, alkoxy, cycloalkyl, heterocyclyl, aryl and heteroaryl.

21. A pharmaceutical composition comprising the ligand-cytotoxic drug conjugate or the pharmaceutically acceptable salt or solvate thereof according to claim 1, and one or more pharmaceutically acceptable carriers, diluents or excipients.

22. A method for modulating a receptor in vitro, the method comprising contacting the receptor with an effective amount of the pharmaceutical composition according to claim 21, wherein the receptor is selected from the group consisting of: HER2 (ErbB2), CD22, CD30, CD33, CD44, CD56, Lewis Y, and GPNMB.

23. A method of treating cancer in a human subject in need thereof, the method comprising administering to the subject an effective amount of the pharmaceutical composition according to claim 21, wherein the cancer is selected from the group consisting of breast cancer, ovarian cancer, stomach cancer, endometrial cancer, salivary gland cancer, lung cancer, colon cancer, renal cancer, rectal cancer, thyroid cancer, pancreatic cancer, prostate cancer, bladder cancer, acute lymphocytic leukemia, acute myeloid leukemia, acute promyelocytic leukemia, chronic myelogenous leukemia, chronic lymphocytic leukemia, Hodgkin's lymphoma, non-Hodgkin's lymphoma and relapsed anaplastic large cell lymphoma.

24. A method of treating cancer in a subject in the need thereof, the method comprising administering to the subject an effective amount of the pharmaceutical composition according to claim 21, wherein the cancer is a tumor-associated receptor overexpressed cancer, wherein the tumor-associated receptor is one or more selected from the group consisting of: HER2 (ErbB2), CD22, CD30, CD33, CD44, CD56, Lewis Y, and GPNMB.

25. The process according to claim 20, wherein the compound of formula (IE) is a compound of formula (IV):

(IV)

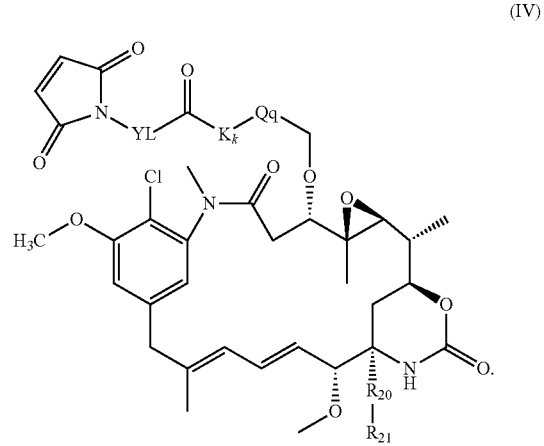

26. A pharmaceutical composition comprising the ligand-cytotoxic drug conjugate or the pharmaceutically acceptable salt or solvate thereof according to claim 19, and one or more pharmaceutically acceptable carriers, diluents or excipients.

27. A method of treating cancer in a human subject in need thereof, the method comprising administering to the subject an effective amount of the pharmaceutical composition according to claim 26, wherein the cancer is selected from the group consisting of breast cancer, ovarian cancer, stomach cancer, endometrial cancer, salivary gland cancer, lung cancer, colon cancer, renal cancer, rectal cancer, thyroid cancer, pancreatic cancer, prostate cancer, bladder cancer, acute lymphocytic leukemia, acute myeloid leukemia, acute promyelocytic leukemia, chronic myelogenous leukemia, chronic lymphocytic leukemia, Hodgkin's lymphoma, non-Hodgkin's lymphoma and relapsed anaplastic large cell lymphoma.

28. The method according to claim 27, wherein the cancer is selected from the group consisting of breast cancer, Hodgkin's lymphoma, and relapsed anaplastic large cell lymphoma.

\* \* \* \* \*